US012782729B2

(12) United States Patent
Huh et al.

(10) Patent No.: US 12,782,729 B2
(45) Date of Patent: Nov. 3, 2026

(54) WELDING INFORMATION PROVIDING DEVICE

(71) Applicant: OTOS WING CO., LTD., Seoul (KR)

(72) Inventors: Moon Young Huh, Seoul (KR); Sung Won Huh, Seoul (KR)

(73) Assignee: OTOS WING CO., LTD., Seoul (KR)

( * ) Notice: Subject to any disclaimer, the term of this patent is extended or adjusted under 35 U.S.C. 154(b) by 988 days.

(21) Appl. No.: 18/084,817

(22) Filed: Dec. 20, 2022

(65) Prior Publication Data

US 2023/0117584 A1 Apr. 20, 2023

Related U.S. Application Data

(63) Continuation of application No. PCT/KR2021/006945, filed on Jun. 3, 2021.

(30) Foreign Application Priority Data

Aug. 20, 2020 (KR) ........................ 10-2020-0104955
Apr. 23, 2021 (KR) ........................ 10-2021-0053111
(Continued)

(51) Int. Cl.
*G02B 27/01* (2006.01)
*A61F 9/06* (2006.01)
(Continued)

(52) U.S. Cl.
CPC .......... *G02B 27/0172* (2013.01); *A61F 9/067* (2013.01); *B23K 9/322* (2013.01);
(Continued)

(58) Field of Classification Search
None
See application file for complete search history.

(56) References Cited

U.S. PATENT DOCUMENTS 7,970,172 B1 6/2011 Hendrickson
10,426,667 B2 10/2019 Magnusson et al.
(Continued)

FOREIGN PATENT DOCUMENTS

CN 109870814 A * 6/2019
JP 11277231 A 10/1999
(Continued)

OTHER PUBLICATIONS

CN 109870814 A (Xu, Xin-lei et al.) Jun. 11, 2019 [retrieved on Feb. 6, 2026]. Retrieved from Espacenet.com, machine translation by EPO. (Year: 2019).*
(Continued)

*Primary Examiner* — John J Norton
(74) *Attorney, Agent, or Firm* — Dinsmore & Shohl LLP

(57) ABSTRACT

Provided is a welding information providing apparatus including a main body provided to be worn by a user, a display unit arranged on the main body and including a display for displaying a welding image to the user, at least one camera unit attached to an outer side of the main body and obtaining welding image frames with respect to a welding operation, and a processor configured to control the display to display the welding image generated based on the welding image frames, wherein the camera unit includes a darkening filter blocking welding light generated due to the welding operation.

5 Claims, 36 Drawing Sheets

(30) Foreign Application Priority Data

| | | | |
|---|---|---|---|
| Apr. 26, 2021 | (KR) | ........................ | 10-2021-0053899 |
| Apr. 26, 2021 | (KR) | ........................ | 10-2021-0053900 |
| Apr. 26, 2021 | (KR) | ........................ | 10-2021-0053901 |

(51) Int. Cl.
*B23K 9/32* (2006.01)
*G02B 5/20* (2006.01)

(52) U.S. Cl.
CPC ...... *G02B 5/205* (2013.01); *G02B 2027/0118* (2013.01); *G02B 2027/0138* (2013.01); *G02B 2027/014* (2013.01)

(56) References Cited

U.S. PATENT DOCUMENTS

| | | | | |
|---|---|---|---|---|
| 2011/0083241 | A1 | 4/2011 | Cole | |
| 2015/0062327 | A1 | 3/2015 | Suda et al. | |
| 2019/0235623 | A1 | 8/2019 | Pollard et al. | |
| 2019/0290491 | A1 | 9/2019 | Woermann | |
| 2021/0200059 | A1 * | 7/2021 | Iinuma .................. | G02B 5/205 |

FOREIGN PATENT DOCUMENTS

| | | | | | |
|---|---|---|---|---|---|
| JP | 2991424 | B2 | | 12/1999 | |
| JP | 2007272174 | A | | 10/2007 | |
| JP | 2008533524 | A | * | 8/2008 | ......... G02F 1/13471 |
| JP | 2013504437 | A | | 2/2013 | |
| JP | 2013207439 | A | | 10/2013 | |
| KR | 101455714 | B1 | | 11/2014 | |
| KR | 20150145219 | A | | 12/2015 | |
| KR | 101673242 | B1 | | 11/2016 | |
| KR | 1020170115573 | A | | 10/2017 | |
| KR | 101875313 | B1 | | 7/2018 | |
| KR | 1020180101201 | A | | 9/2018 | |
| KR | 1020210034408 | A | | 3/2021 | |
| KR | 1020210094916 | A | | 7/2021 | |

OTHER PUBLICATIONS

CN 109870814 A (Xu, Xin-lei et al.) Jun. 11, 2019 [retrieved on Feb. 6, 2026]. Retrieved from Foreign Image and Text database, translation by Clarivate Analytics. (Year: 2019).*
JP 2008-533524 A (Magnusson, Christina M. et al.) Aug. 21, 2008 [retrieved on Feb. 7, 2026]. Retrieved from Foreign Image and Text database, translation by Clarivate Analytics. (Year: 2008).*

* cited by examiner

WELDING INFORMATION PROVIDING DEVICE

TECHNICAL FIELD

One or more embodiments of the disclosure relate to a welding information providing apparatus.

RELATED ART

An operator wears a protector for protection from light and high temperature heat generated during a welding process. While the operator wears the protector, the operator may only check processing of the welding through the protector, and thus, the operator has to remove the protector and check with the naked eye in order to identify various information for the welding operation, such as conditions set in a welding apparatus.

When a skill level of an operator is not high, especially when an automatic welding mask and a manual welding mask are worn, the operator may see only a portion adjacent to welding light, and it is difficult for the operator to recognize a specific welding situation such as the surroundings of the welding. Accordingly, it is necessary to provide the operator with a high-definition image that allows the operator to visually check the welding surroundings, and provide the operator with specific information about welding status information.

Moreover, illuminance/luminance of a welding light spot are very high during the welding operation, a darkening filter is used to protect eyes of the worker from the welding light spot and to allow the welding operation to be performed effectively. In this case, other region than the welding light spot is not visible at all, which makes the welding operation difficult and degrades accuracy in the welding.

The above issue may identically occur for medical staff during skin treatment and/or diagnosis performed by using high-luminance/high-illuminance light such as laser light, as well as the welding operation, and becomes problematic in other operations performed using the high-luminance/high-illuminance light.

DETAILED DESCRIPTION OF THE DISCLOSURE

Technical Problem

According to an embodiment of the present disclosure, provided are a camera unit and a welding information providing apparatus including the camera unit which shows an operator welding surrounding environment, as well as a welding spot, so as to improve welding accuracy of the operator.

According to an embodiment of the present disclosure, provided is a welding information providing apparatus which shows a user welding surrounding environment, as well as a welding spot, so as to improve welding accuracy of the user.

According to an embodiment of the present invention, provided is a welding information providing apparatus capable of improving a welding accuracy of the user by dividing a screen of a display according to a distance of a field of view.

Also, provided is a welding information apparatus capable of securing an accurate field of view during welding by preventing foreign substances from infiltrating into a space in which welding information is provided.

However, the above technical features are exemplary, and the scope of the disclosure is not limited thereto.

Technical Solution

According to an embodiment of the present disclosure, provided is a welding information providing apparatus including a main body provided to be worn by a user, a display unit arranged on the main body and including a display for displaying a welding image to the user, at least one camera unit attached to an outer side of the main body and obtaining welding image frames with respect to a welding operation, and a processor configured to control the display to display the welding image generated based on the welding image frames, wherein the camera unit includes a darkening filter blocking welding light generated due to the welding operation.

Advantageous Effects of Disclosure

A welding information providing apparatus according to one or more embodiments of the present disclosure may obtain a welding image, in which a certain amount of welding light is shielded, without separately processing a captured image by arranging a filter unit that may shield the welding light in front of a camera.

Also, the welding information providing apparatus may effectively control a shielding degree by including a darkening filter and a neutral density filter and controlling a darkening density or a neutral density according to whether there is welding light or an intensity of the welding light.

The welding information providing apparatus according to one or more embodiments of the present invention may form a compact-sized main body while providing clear welding images, by providing a user with a welding image after changing a path of the welding image via a path change unit.

Also, the welding information providing apparatus according to one or more embodiments of the present invention may provide a user with a welding image after minimizing sense of difference or sense of incongruity with an actual working site by obtaining an image through a camera unit arranged at a similar height to the view of the user.

The welding information providing apparatus according to one or more embodiments may include an outer cover plate to protect a camera unit.

Also, the welding information providing apparatus according to one or more embodiments of the present disclosure may provide a high-image quality welding image by minimizing a refractive index of an outer cover plate.

Also, the welding information providing apparatus according to one or more embodiments of the present disclosure may provide a user with a welding image after minimizing sense of difference or sense of incongruity with an actual working site by obtaining an image through a camera unit arranged at a similar height to the view of the user.

The present disclosure may provide a welding information providing apparatus capable of improving an accuracy of the user in welding by dividing a screen of a display according to a distance of a field of view.

Also, the present disclosure may provide a welding information providing apparatus capable of allowing a user to perform a precise and accurate welding operation by adjusting a distance between lenses or adjusting a distance of a field of view.

Also, a clear welding image may be provided during welding by preventing foreign substances from infiltrating onto a path of the welding image from outside by using an inner cover unit installed in the main body.

However, the present disclosure is not limited to the above effects.

BEST MODE

Figure 1:
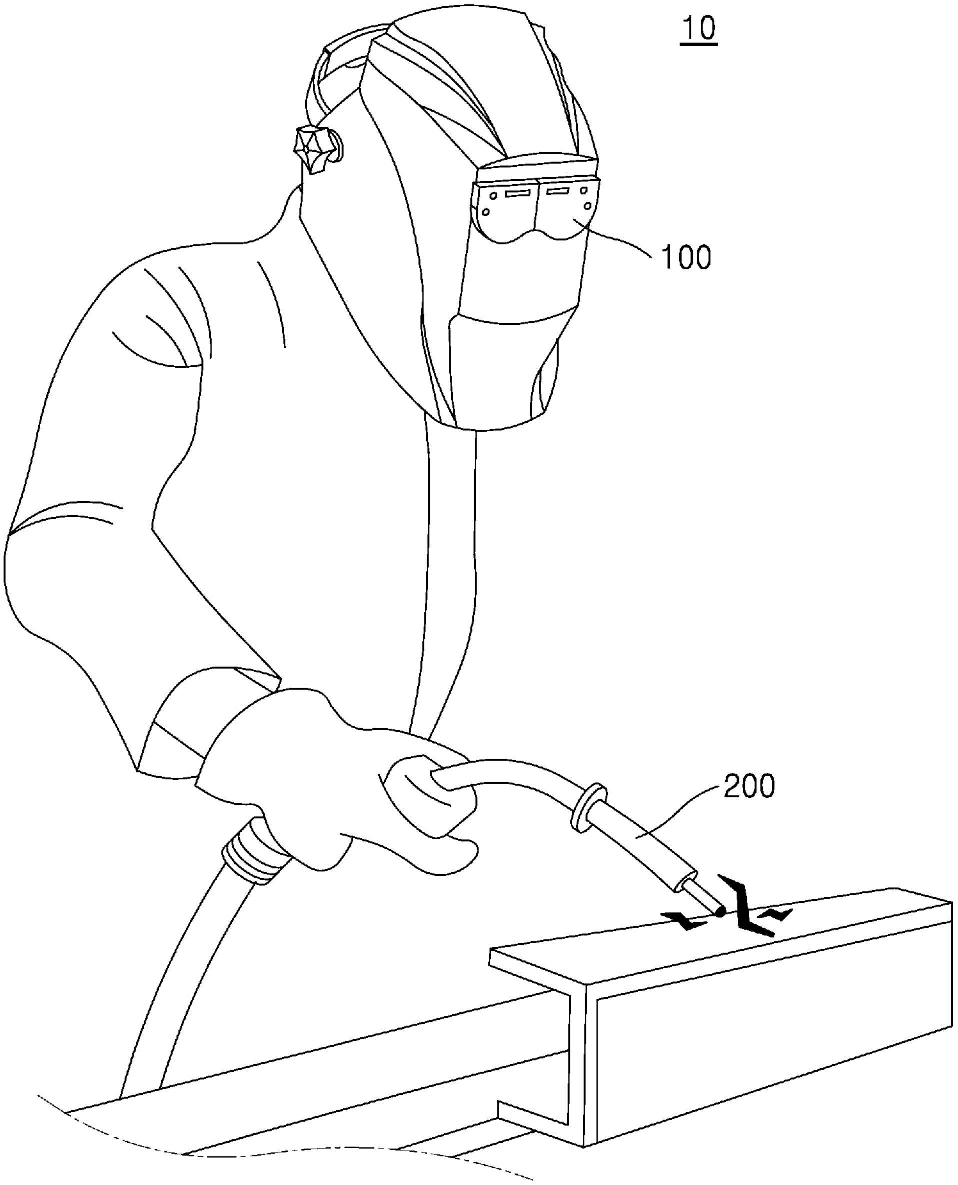
FIG. 1 is a diagram for describing a structure of a welding system according to an embodiment of the present disclosure.

According to an embodiment of the present disclosure, provided is a welding information providing apparatus including a main body provided to be worn by a user, a display unit arranged on the main body and including a display for displaying a welding image to the user, at least one camera unit attached to an outer side of the main body and obtaining welding image frames of a welding operation, and a processor configured to control the display to display the welding image generated based on the welding image frames, wherein the camera unit includes a darkening filter blocking welding light generated due to the welding operation.

In an embodiment of the present disclosure, the darkening filter may be arranged in front of a lens receiving light from a subject.

In an embodiment of the present disclosure, the welding information providing apparatus may further include an optical sensor detecting whether there is the welding light and the intensity of the welding light, and the processor may control a darkening density of the darkening filter according to whether there is the welding light or the intensity of the welding light detected by the optical sensor.

In an embodiment of the present disclosure, the camera unit may further include a neutral density filter disposed in front of the darkening filter.

In an embodiment of the present disclosure, the neutral density filter may be a digital filter of which a neutral density is controlled by the processor.

According to an embodiment of the present disclosure, provided is a camera unit including a lens assembly including one or more lenses, a substrate assembly including an image sensor that recognizes light passing through the lens assembly and a printed circuit board coupled to the image sensor, a filter unit arranged on a path through which the light moves and including a darkening filter blocking the light, and a processor configured to control a darkening density of the darkening filter.

In an embodiment of the present disclosure, the camera unit may further include an optical sensor detecting whether there is the light and the intensity of the light, and the processor may control a darkening density of the darkening filter according to whether there is the light or the intensity of the light detected by the optical sensor.

In an embodiment of the present disclosure, the filter unit may be arranged in front of the lens assembly receiving light from a subject.

In an embodiment of the present disclosure, the filter unit may be arranged between the lens assembly and the image sensor.

In an embodiment of the present disclosure, the filter unit may further include a neutral density filter disposed in front of the darkening filter.

In an embodiment of the present disclosure, the neutral density filter may be a digital filter of which a neutral density is controlled by the processor.

According to an embodiment of the present disclosure, provided is a welding information providing apparatus including a main body provided to be worn by a user, a camera unit attached to outside of the main body and including at least one camera obtaining welding image frames from a welding operation, a display unit arranged in the main body and providing the welding image, a path change unit changing a path of the welding image provided from the display unit and guiding the path to eyes of the user, and a processor configured to control the display to display the welding image generated based on the welding image frames, wherein a virtual extension line extending from an optical axis of the camera passes through the path change unit.

In an embodiment of the present disclosure, the display unit may be arranged in the main body, and a direction of providing the welding image may be arranged to be parallel to the virtual extension line.

In an embodiment of the present disclosure, the path change unit may include a first mirror changing a path of the welding image provided from the display unit, and a second mirror changing the path of the welding image changed by the first mirror and guiding the path to the eyes of the user.

In an embodiment of the present disclosure, the virtual extension line may pass through the second mirror.

In an embodiment of the present disclosure, the camera unit may be located within a range of ±30 mm in a vertical direction based on a virtual first surface that is in parallel to the path of the welding image from the second mirror and passes through the center of the second mirror.

In an embodiment of the present disclosure, the display unit may be arranged in the main body, and a direction of providing the welding image may be arranged to intersect with the virtual extension line.

In an embodiment of the present disclosure, the path change unit may include a mirror that guides the path of the welding image provided from the display unit to the eyes of the user.

In an embodiment of the present disclosure, the virtual extension line may pass through the mirror.

In an embodiment of the present disclosure, the camera unit may be located within a range of ±30 mm in a vertical direction based on a virtual first surface that is in parallel to the path of the welding image from the mirror and passes through the center of the mirror.

In an embodiment of the present disclosure, a distance of the path through which the welding image passes from the display unit to the eyes of the user via the path change unit may be determined within a range of 200 mm to 700 mm.

According to an aspect of the present disclosure, a welding information providing apparatus may include a main body provided to be worn by a user, a camera unit attached to an outer side of the main body and including at least a camera obtaining welding image frames from a welding operation, an outer cover unit including an outer cover frame coupled to the main body, and an outer cover plate provided in the outer cover frame and arranged in front of the camera so as to protect the camera, a display unit arranged in the main body and providing a welding image generated based on the welding image frames, and a path change unit changing a path of the welding image provided from the display unit and guiding the path to the eyes of the user.

The outer cover plate may be attachable to/detachable from the outer cover frame.

Also, the outer cover plate may be formed of a material through which light generated from a welding operation may transmit.

Also, the outer cover plate may include an inner surface facing the face of the user and an outer surface located opposite to the inner surface, and a first radius of curvature of the inner surface and a second radius of curvature of the outer surface may be different from each other.

Also, a center of the first radius of curvature and a center of the second radius of curvature may be spaced apart from each other.

Also, the outer cover plate may include a center portion and an outer portion spaced apart from the center portion and formed along the periphery of the outer cover plate, and a first thickness of the center portion and a second thickness of the outer portion may be different from each other.

In addition, the outer cover unit may further include a light blocking cartridge disposed behind the outer cover plate and blocks at least a part of the transmitting welding light.

Also, a virtual extension line extending from an optical axis of the camera may pass through the path change unit.

Also, a distance of a path through which the welding image passes to the eyes of the user via the path change unit may be determined within a range from 200 mm to 700 mm.

According to an aspect of the present disclosure, a welding information providing apparatus may include a main body provided to be worn by a user, a camera unit attached to an outer side of the main body and including at least a camera obtaining welding image frames from a welding operation, a display unit arranged in the main body and including a display panel providing the welding image, a processor configured to control the display unit to display the welding image generated based on the welding image frames, and a lens unit including a pair of first lenses corresponding to left and right eyes of the user and guiding the image displayed by the display unit to the eyes of the user through the first lenses.

Also, the first lens may be a convex lens or a Fresnel lens.

In addition, the welding information providing apparatus may include a lens adjustment module for adjusting a distance between centers of the first lenses.

Also, a viewing distance from the center of the field of view of the user to the display panel may be about 60 mm to 100 mm.

In addition, the welding information providing apparatus may include a display adjustment module for moving the display panel back and forth.

In addition, the welding information providing apparatus may include a lens position adjustment module for moving the lens unit back and forth.

In addition, when the viewing distance is 60 mm to 80 mm, a pair of second lenses may be inserted between the first lens and the display panel to correspond to the first lenses.

Also, the second lens may be a concave lens.

In addition, when the viewing distance is 60 mm to 80 mm, the display unit may display the welding image after dividing the welding image into two screens to correspond to the eyes of the user.

Also, the processor may adjust a distance between centers of the two screens displayed on the display unit based on the distance between the centers of the first lenses.

According to an embodiment of the present disclosure, provided is a welding information providing apparatus including a main body provided to be worn by a user, a camera unit attached to the main body and including at least a camera obtaining welding image frames from a welding operation, a display unit arranged in the main body and providing a welding image generated based on the welding image frames, a path change unit changing a path of the welding image provided from the display unit and guiding the path to eyes of the user, and an inner cover unit arranged on a path of the welding image and opening/closing a space formed by the display unit and the path change unit.

In an embodiment of the present disclosure, the inner cover unit may be arranged between the path change unit and the eyes of the user.

In an embodiment of the present disclosure, the inner cover unit may include a cover frame unit installed on the main body and having a central portion that is opened, and an inner cover plate covering the central portion and connected to the cover frame unit.

In an embodiment of the present disclosure, the inner cover unit may further include a cover holder unit having one end connected to the cover frame unit and covering the inner cover plate.

In an embodiment of the present disclosure, the inner cover unit may further include a lens unit that may be installed on the cover holder unit and arranged so as to face the inner cover plate.

In an embodiment of the present disclosure, the inner cover unit may further include a sealing unit that is arranged between the cover frame unit and the inner cover plate and has both sides coming into contact respectively with the cover frame unit and the inner cover plate.

In an embodiment of the present disclosure, the sealing unit may be formed of an elastically deformable material.

In an embodiment of the present disclosure, the path change unit may include a mirror that guides the path of the welding image provided from the display unit to the eyes of the user.

In an embodiment of the present disclosure, the welding information providing apparatus may further include a processor controlling the display unit to display the welding image generated based on the welding image frames.

In an embodiment of the present disclosure, a virtual extension line extending from an optical axis of the camera may pass through the path change unit.

Other aspects, features and advantages other than those described above will become apparent from the following detailed description of the drawings, claims and disclosure.

MODE OF DISCLOSURE

The embodiments will be described below in more detail with reference to the accompanying drawings. Those components that are the same or are in correspondence are rendered the same reference numeral regardless of the figure number, and redundant explanations are omitted.

As the present disclosure allows for various changes and numerous embodiments, particular embodiments will be illustrated in the drawings and described in detail in the written description. The attached drawings for illustrating one or more embodiments are referred to in order to gain a sufficient understanding, the merits thereof, and the objectives accomplished by the implementation. However, the embodiments may have different forms and should not be construed as being limited to the descriptions set forth herein.

While such terms as "first," "second," etc., may be used to describe various components, such components must not be limited to the above terms. The above terms are used only to distinguish one component from another.

An expression used in the singular encompasses the expression of the plural, unless it has a clearly different meaning in the context.

In the present specification, it is to be understood that the terms such as "including," "having," and "comprising" are intended to indicate the existence of the features or components disclosed in the specification, and are not intended to preclude the possibility that one or more other features or components may exist or may be added.

It will be understood that when a unit, region, or component is referred to as being "formed on" another layer, region, or component, it can be directly or indirectly formed on the other layer, region, or component. That is, for example, intervening units, regions, or components may be present.

It will be understood that when an element is referred to as being "connected" or "coupled" to another element, it can be directly connected or coupled to the other element or intervening elements may be present.

It will be further understood that the terms "connected" or "coupled" specify the presence of stated features or components, but do not preclude the presence or addition of one or more other features or components.

Sizes of components in the drawings may be exaggerated for convenience of explanation. In other words, since sizes and thicknesses of components in the drawings are arbitrarily illustrated for convenience of explanation, the following embodiments are not limited thereto.

FIG. 1 is a diagram for describing a structure of a welding system according to an embodiment of the present disclosure.

Referring to FIG. 1, a welding system 10 according to the present disclosure may include a welding information providing apparatus 100 and a welding torch 200. The welding information providing apparatus 100 and the welding torch 200 may be connected to each other through a communication network to transmit and receive data. The welding information providing apparatus 100 and the welding torch 200 may be operated while matching in one-to-one correspondence, but one or more embodiments are not limited thereto, and a one-to-n relationship is possible. That is, n welding torches 200 may be connected to one welding information providing apparatus, or one welding torch 200 may be connected to n welding information providing apparatuses 100. In addition, the welding information providing apparatus 100 and the welding torch 200 may exchange data by communicating with an additional server (not shown).

The welding information providing apparatus 100 may provide information about a welding situation to an operator. In detail, the welding information providing apparatus 100 obtains a welding image that is obtained by using at least one camera mounted on the welding information providing apparatus 100, and may generate a composite image based on the welding image and display the image to the operator. Here, the welding information providing apparatus 100 may generate the composite image by using a high dynamic range (HDR) technology, and may display a high-definition composite image to the operator. Here, the operator may visually check information about a shape of welding beads and a surrounding environment other than a portion adjacent to the welding light through the high-definition composite image.

The welding information providing apparatus 100 according to an embodiment of the present disclosure may obtain the welding image by arranging a camera unit at a position equal to the user's field of view. As such, the welding information providing apparatus 100 according to an embodiment of the present disclosure may obtain the welding image that is similar to the view that the user may obtain when directly seeing the working site.

The welding information providing apparatus 100 according to an embodiment of the present disclosure may obtain images from two or more cameras and display the respective images through at least one display in order to provide high-definition composite welding image. For example, the camera unit may include two cameras which may be arranged at positions respectively corresponding to left and right eyes of the user.

Here, the welding information providing apparatus 100 may synthesize images by repeatedly capturing images while varying a shutter speed, an ISO sensitivity, and a gain value of each camera. The welding information providing apparatus 100 according to an embodiment of the present disclosure may improve the image quality through a contrast ratio treatment on the obtained composite image.

Also, the welding information providing apparatus 100 of the present disclosure may provide a function of displaying welding information in preferred color (e.g., green and blue) by using RGB. In addition, the welding information providing apparatus 100 of the present disclosure may provide a function of correcting power of a magnifying glass (e.g., screen enlargement and reduction). Also, the welding information providing apparatus 100 of the present disclosure may provide a temperature composite image by using an additional thermal imaging camera. Here, the welding information providing apparatus 100 may indicate a welding temperature in a color. The welding information providing apparatus 100 of the present disclosure may support a function of providing sound (e.g., notification alarm) or guidance voice with respect to the above-described functions.

The welding torch 200 according to an embodiment of the present disclosure may sense a welding situation including a welding temperature, a welding direction, a welding inclination, a welding speed, a distance between a base material and the welding torch, etc. of a real-time welding operation, through at least one sensor. The welding torch 200 may monitor a state of the torch and may change a setting value of a welding torch operation according to the welding situation.

The welding information providing apparatus 100 of the present disclosure may receive information about an operation setting and an operation state from the welding torch 200 through a communication network connected to the welding torch 200, and may provide the operator with operation information based on the received welding information through visual feedback.

For example, when receiving sensing information about the welding temperature value, the welding information providing apparatus 100 may output a notification corresponding to the temperature value in various methods, e.g., light, vibration, message, etc. Here, the notification may be visual feedback provided on the display unit or the display, or may be audible feedback provided through sound (e.g., notification alarm) or guiding voice.

In addition, the sensing information about the temperature value may include information about whether the temperature value exceeds a temperature range set in advance, etc. Also, the sensing information about the temperature value may include a numerical value, a grade, a level, etc. corresponding to the temperature value on a welding surface.

When it is determined that the temperature values of the torch and the welding surface exceed the temperature range set in advance, the welding information providing apparatus 100 according to an embodiment of the present disclosure may guide the operator to stop the operation. The welding performed at the temperature exceeding the temperature range set in advance has a risk of quality degradation, and the operator may be guided to adjust the temperature value of the torch.

When it is sensed that a current or voltage status of the welding torch 200 is abnormal, the welding information providing apparatus 100 according to an embodiment of the present disclosure may provide the visual feedback for warning.

Here, the visual feedback may denote providing of an icon indicating danger on a part of the display unit of the welding information providing apparatus 100, which is displaying the working site. In another example, the welding information providing apparatus 100 may provide an operation suspending guidance through the visual feedback by repeatedly increasing and decreasing a saturation of a certain color (e.g., red) on the entire screen of the display unit.

According to an embodiment of the present disclosure, the welding information providing apparatus 100 may sense the welding information via a sensor (e.g., first sensor) included in the welding information providing apparatus 100, in addition to at least one sensor (e.g., second sensor) included in the welding torch 200. Here, the welding information including the welding situation, e.g., a degree of light related to the real-time welding operation, a welding temperature, a welding direction, a welding inclination, a welding speed, a distance between the base material and the welding torch, etc. may be sensed via at least one sensor.

Likewise, the welding information providing apparatus 100 may provide guidance corresponding to the welding information based on the welding information sensed by the sensor (e.g., first sensor) included in the welding information providing apparatus 100.

According to an embodiment of the present disclosure, the welding information providing apparatus 100 may change a movement of the welding torch by sensing a preset user movement or a preset user voice after the operation suspension guidance is provided.

In another embodiment, when communication between the welding information providing apparatus 100 and the welding torch 200 is not sufficiently performed, the welding information providing apparatus 100 may obtain temperature values of the torch and the welding surface through an image sensing provided therein. For example, the welding information providing apparatus 100 may obtain temperature values of the torch and the welding surface based on image data obtained through a thermal imaging camera.

Although the above example illustrates that information received from the welding torch 200 only includes welding temperature information, the welding information providing apparatus 100 may provide various guidance for various welding information.

Figure 2:
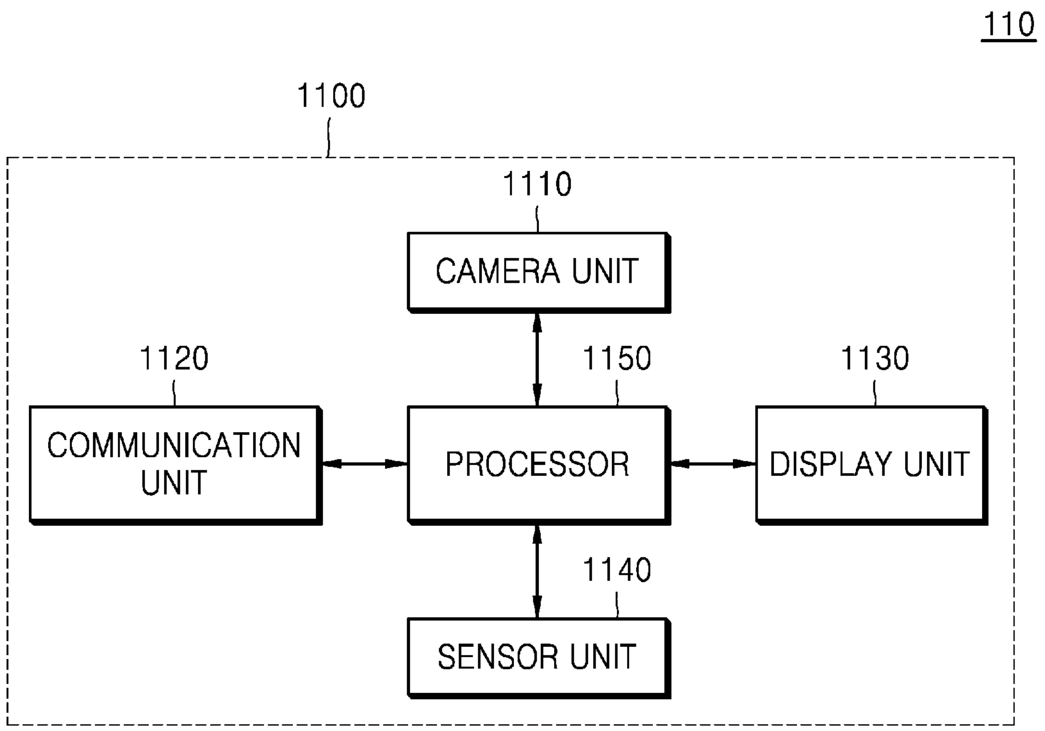
FIG. 2 is a schematic block diagram for describing elements of a welding system according to an embodiment of the present disclosure.

FIG. 2 is a schematic block diagram for describing elements of a welding system 110 according to an embodiment of the present disclosure.

Referring to FIG. 2, the welding system 110 may include a welding information providing apparatus 1100 and a welding torch 1200. The welding information providing apparatus 1100 may include a main body 1160, a camera unit 1110, a communication unit 1120, a display unit 1130, a processor 1150, and a sensor unit 1140.

The camera unit 1110 may include at least one camera device, and may include a camera for capturing images of a welding operation site. The camera unit 1110 according to an embodiment of the present disclosure may be a camera located adjacent to the display unit 1130 of the welding information providing apparatus 1100. For example, a first camera and a second camera of the camera unit 1110 may be symmetrically mounted on one area of a front portion of the welding information providing apparatus 1100, respectively. In another embodiment, the camera unit 1110 may be formed to be attachable and detachable, and may be mounted while changing its position as necessary. As described above, the camera unit 1110 may be mounted to be adjacent to the display unit 1130, but may be mounted by changing the position to the side portion of the main body 1160 as necessary. Alternatively, the camera unit 1110 may be mounted on the upper portion of the main body 1160, that is, on the head of the user. The camera unit 1110 may receive a control command from the processor 1150, and may capture images of the welding operation site by changing the settings such as a shutter speed, an ISO sensitivity, gain value, etc. in response to the control command. The camera unit 1110 may include the first camera and the second camera which may capture images of the welding operation site under different photographing settings respectively.

The camera unit 1110 according to an embodiment of the present disclosure may include a thermal imaging camera. The welding information providing apparatus 1100 may obtain a temperature image by synthesizing a thermal image obtained by thermal imaging camera with an image of a welding site.

According to an embodiment of the present disclosure, a lighting unit (not shown) electrically connected to the processor 1150 may be further provided. The lighting unit (not shown) is located outside the welding information providing apparatus 1100 and is configured to irradiate light toward at least a welding operation area. The lighting unit (not shown) may include a plurality of LED modules, and an output degree of light irradiated through the lighting unit (not shown) may be adjusted by the control of the processor 1150. According to an embodiment, the lighting unit (not shown) may operate while interlocking with the operation of the camera unit 1110 according to the control of the processor 1150.

The communication unit 1120 is an element for receiving welding information from the welding torch 1200 and transmitting a command for controlling the welding torch 1200. According to an embodiment of the present disclosure, the communication unit 1120 may transmit a composite image to an external device other than the welding torch 1200. Here, the external device may include various devices including a communication module, such as a smart phone of an operator/third party, a computer, etc.

The communication unit 1120 may be an element performing communication with various types of external devices according to various types of communication methods. The communication unit 1120 may include at least one of a Wi-Fi™ (wireless communication technology) chip, a Bluetooth™ (wireless communication protocol) chip, a wireless communication chip, and a near field communication (NFC) chip. In particular, when a Wi-Fi™ chip or a Bluetooth™ chip is used, various connection information such as an SSID, a session key, etc. is transmitted/received first, and then, communication is connected using the above connection information and various information may be transmitted/received. The wireless communication chip refers to a chip that performs communication according to various communication standards such as IEEE, Zigbee™ (standard-based communication), 3rd Generation (3G) (mobile communication technology), 3rd Generation Partnership Project (3GPP) (standard), Long Term Evolution (LTE) (communication technology), etc. The NFC chip refers to a chip operating in an NFC type using a frequency band of 13.56 MHz from among various RF-ID frequency bands such as 135 kHz, 13.56 MHz, 433 MHz, 860 to 960 MHz, 2.45 GHZ, etc.

The display unit 1130 is an element for providing the operator with high-definition composite images. In detail, the display unit 1130 may include a display 1131 (see FIG. 4) for displaying a composite image obtained by synthesizing images obtained through the camera 1110 to the operator.

According to an embodiment of the present disclosure, the rear portion of the display unit 1130, that is, the portion facing the user, may include the display 1131 (refer to FIG. 4) for displaying a high-definition image to the user and a main lens member 1135 (see FIG. 4) for seeing the display 1131.

The display included in the display unit 1130 may display a high-definition composite image so that the operator may visually check the surrounding environment (e.g., a shape of a previously worked welding bead, etc.) other than a portion adjacent to the welding light. Also, the display unit 1130 may guide visual feedback (e.g., welding processing direction) given to the operator with respect to the welding processing status.

The display 1131 included in the display unit 1130 may be implemented as various display techniques such as a liquid crystal display (LCD), an organic light emitting diode (OLED), light-emitting diode (LED), liquid crystal on silicon (LcoS), or digital light processing (DLP), etc. Here, the display according to an embodiment of the present disclosure is implemented as a panel of an opaque material and the operator may not be directly exposed to harmful light. However, one or more embodiments are not limited thereto, and the display may be implemented as a transparent display.

The sensor unit 1140 may include a plurality of sensor modules that are formed to sense various information about the welding site and obtain welding information. Here, the welding information may include a welding temperature, a welding direction, a welding inclination, a welding speed, a distance between the base material and the welding torch from the real-time welding operation. Moreover, the sensor unit 1140 may include an optical sensor that is formed to detect a degree of light at least in the welding operation area.

According to an embodiment of the present disclosure, the sensor unit 1140 may include an illuminance sensor. Here, the sensor unit 1140 may obtain information about an intensity of the welding light on the welding site. The sensor unit 1140 may further include various kinds of sensors, such as a proximity sensor, a noise sensor, a video sensor, an ultrasonic sensor, and an RF sensor, in addition to the illuminance sensor, and may sense various changes related to the welding operation environment.

The processor 1150 may generate a high-definition composite image by synthesizing the welding image frames received through the camera unit 1110. The processor 1150 may obtain the composite image by synthesizing in parallel the frames that are obtained by the camera unit 1110 in a time-serial order by setting different photographing conditions for each frame. In detail, the processor 1150 may control the camera unit 1110 to capture images by changing the shutter speed, the ISO sensitivity, gain value, etc. of the camera unit 1110 may working.

Here, the processor 1150 may set photographing condition differently according to conditions, e.g., the welding light of the sensed welding site, the ambient light, a movement degree of the welding torch 1200, etc. In detail, the processor 1150 may set the photographing condition so that the ISO sensitivity and the gain are reduced as the welding light of the welding site and/or the ambient light increase. Also, when it is sensed that the movement and/or the working speed of the welding torch 1200 are fast, the photographing condition may be set to increase the shutter speed.

The processor 1150 may synthesize images of a preset number of frames in parallel. According to an embodiment of the present disclosure, each image in the preset frame may be captured under different photographing conditions.

When there are two or more camera units 1110, the processor 1150 according to an embodiment of the present disclosure may control each camera unit to capture images under different photographing conditions. In this case, the processor 1150 may also synthesize images of a preset number of frames in parallel.

The processor 1150 may control the overall operations of the welding information providing apparatus 1100 using various programs stored in a memory (not shown). For example, the processor 1150 may include a central processing unit (CPU), a random-access memory (RAM), a read-only memory (ROM), and a system bus. Here, the ROM is an element in which a set of instructions for system booting are stored, and the CPU copies an operating system (OS) stored in the memory of the welding information providing apparatus 1100 to the RAM according to the instructions stored in the ROM and executes the O/S to boot the system. When booting is finished, the CPU may copy various applications stored in the memory to the RAM and execute the applications to perform various operations. In the above description, the processor 1150 includes only one CPU, but the processor may be implemented with a plurality of CPUs (or DSP, SoCs, etc.).

According to an embodiment of the present disclosure, the processor 1150 may be implemented as a digital signal processor (DSP) processing digital signals, a microprocessor, and/or a time controller (TCON). However, one or more embodiments are not limited thereto, and the processor may include one or more from a CPU, a micro controller unit (MCU), a micro processing unit (MPU), a controller, an application processor (AP), a communication processor (CP), and an advanced RISC machine (ARM) processor, or may be defined by a corresponding term. In addition, the processor 1150 may be implemented as a system on chip (SoC) or large scale integration (LSI) having a processing algorithm built therein, or in the form of a field programmable gate array (FPGA).

Although not shown in the drawings, the welding torch 1200 may include a communication unit, a sensor unit, and a second processor.

The communication unit transmits and receives data to/from the welding information providing apparatus 1100. The communication unit includes a module capable of short-range wireless communication (e.g., Bluetooth™, Wi-Fi, Wi-Fi-Direct) or long-distance wireless communication (3G, High-Speed Downlink Packet Access (HSDPA) or LTE).

The sensor unit or the second sensor is included in the welding torch and is configured to sense welding conditions such as a welding temperature, a welding speed, a welding inclination, a welding direction, and a distance between the base material and the welding torch.

The sensor unit detects at least one of various changes such as a change in posture of a user holding the welding torch 1200, a change in illuminance of the welding surface, a change in an acceleration of the welding torch 1200, etc., and may transmit an electrical signal corresponding to the change to the second processor. That is, the sensor unit may sense a state change made based on the welding torch, generate a sensing signal corresponding thereto, and transmit the sensing signal to the second processor.

In the present disclosure, the sensor unit may include various sensors, and when the welding torch 1200 is driven (or based on a user setting), power is supplied to at least one sensor that is preset according to control to sense a change in the status of the welding torch 1200.

In this case, the sensor unit may be configured to include at least one of all types of sensing devices capable of detecting a change in the status of the welding torch 1200. For example, the sensor unit may include at least one of various sensing devices such as an acceleration sensor, a gyro sensor, an illuminance sensor, a proximity sensor, a pressure sensor, a noise sensor, a video sensor, a gravity sensor, etc. The degree of light within the welding operation area sensed by the illuminance sensor of the welding torch 1200 may be transferred to the processor 1150 via the communication unit, and the processor 1150 may control the lighting unit (not shown) and/or the camera 1110 based on the degree of light transferred through the illuminance sensor of the welding torch 1200, not via the sensor unit 1140 of the welding information providing apparatus 1100.

In addition, the acceleration sensor is an element for sensing the movement of the welding torch 1200. In detail, the acceleration sensor may measure a dynamic force such as an acceleration, vibration, or impact of the welding torch 1200, and may measure the movement of the welding torch 1200.

The gravity sensor is an element for sensing a direction of gravity. That is, the sensing result of the gravity sensor may be used to determine the movement of the welding torch 1200 along with the acceleration sensor. In addition, the direction in which the welding torch 1200 is gripped may be determined via the gravity sensor.

In addition to the above-described types of sensors, the welding torch 1200 may further include various types of sensors such as a gyroscope sensor, a geomagnetic sensor, an ultrasonic sensor, and a radio frequency (RF) sensor, and may detect various changes regarding the welding work environment.

FIGS. 3 to 6 are diagrams for describing the welding information providing apparatus 1100 according to an embodiment of the present disclosure.

Figure 3:
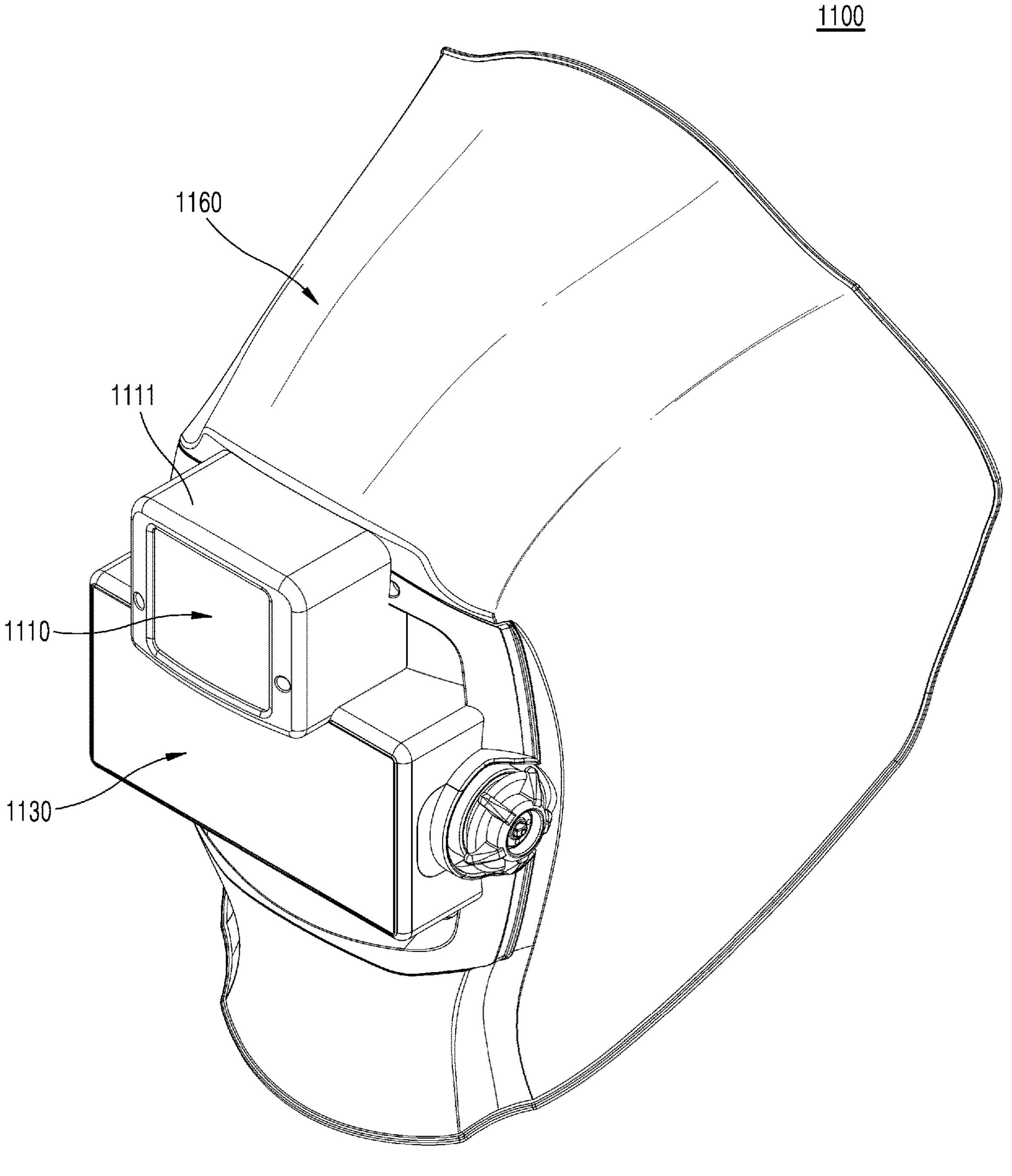
FIG. 3 is a perspective view of a welding information providing apparatus according to an embodiment of the present disclosure.
Figure 4:
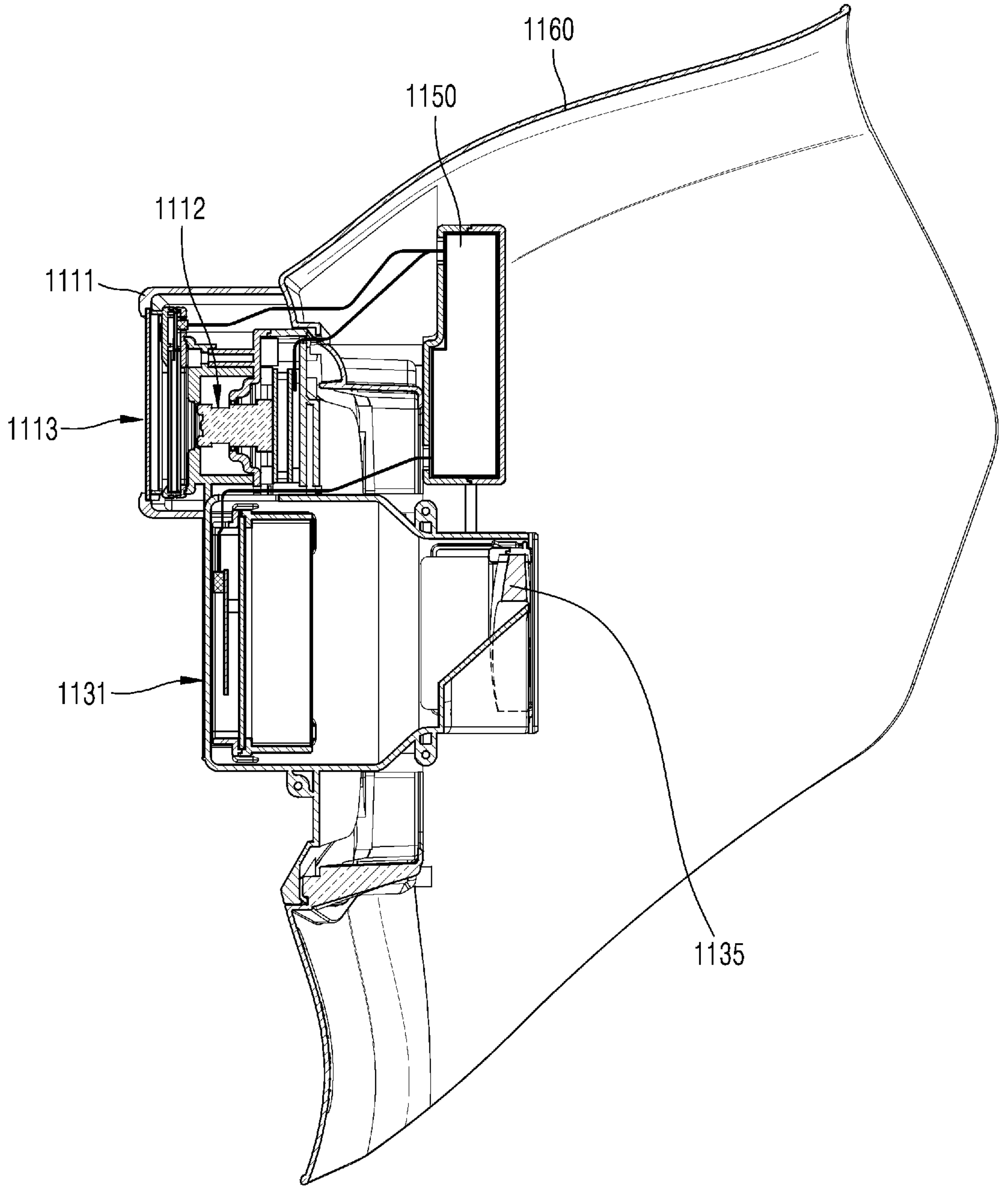
FIG. 4 is a cross-sectional view for describing inside of the welding information providing apparatus of FIG. 3.
Figure 5:
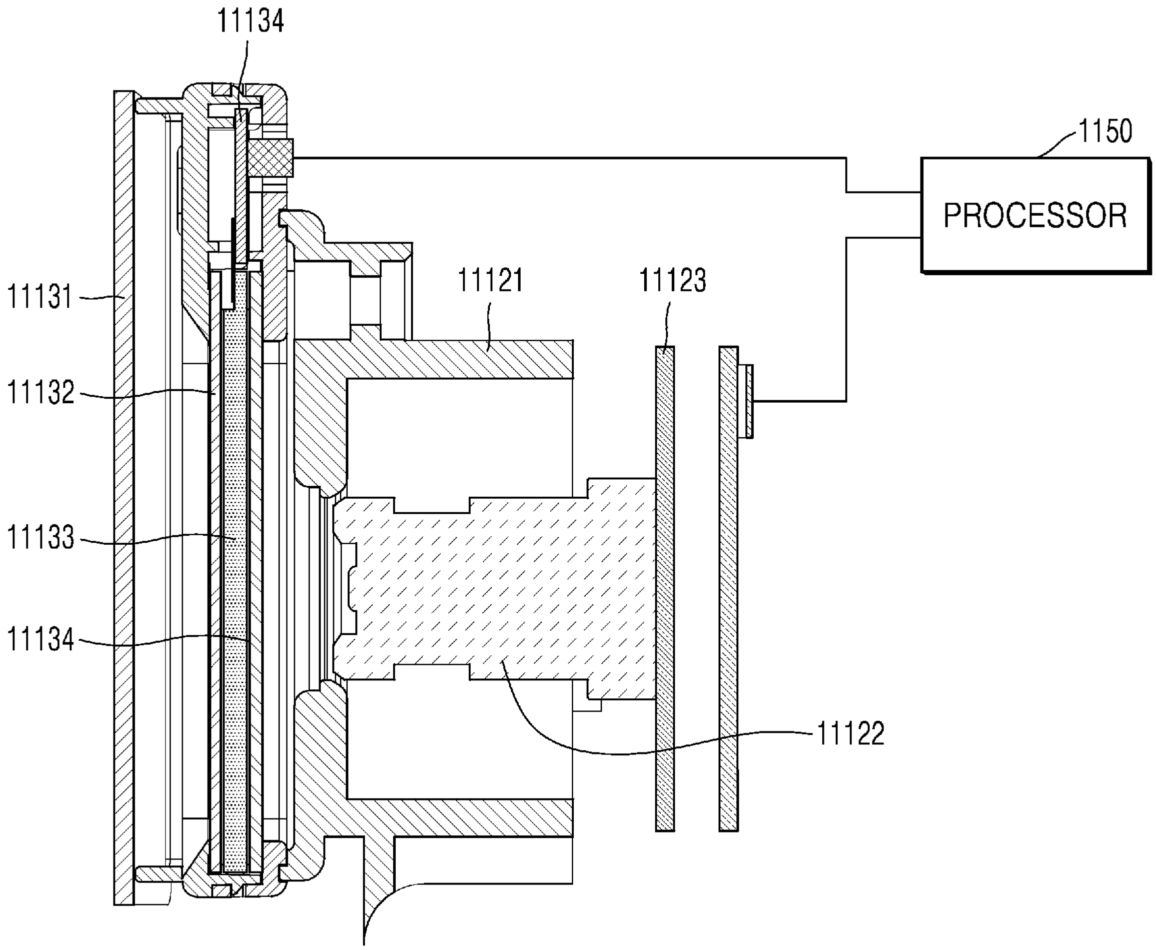
FIG. 5 is a diagram only showing elements of a camera unit of FIG. 4.
Figure 6:
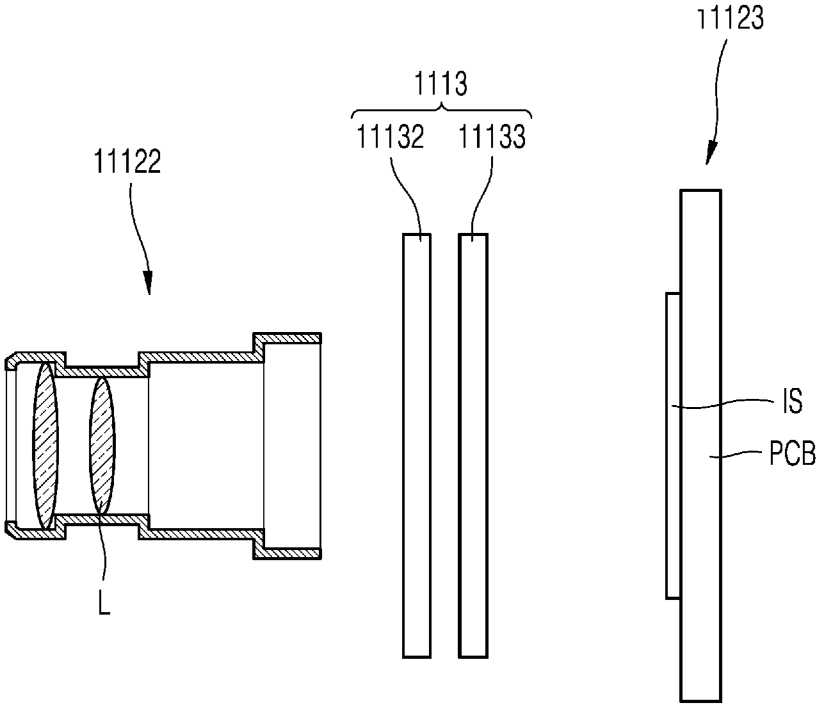
FIG. 6 is a diagram showing a camera unit 1110 according to another embodiment.
Figure 7:
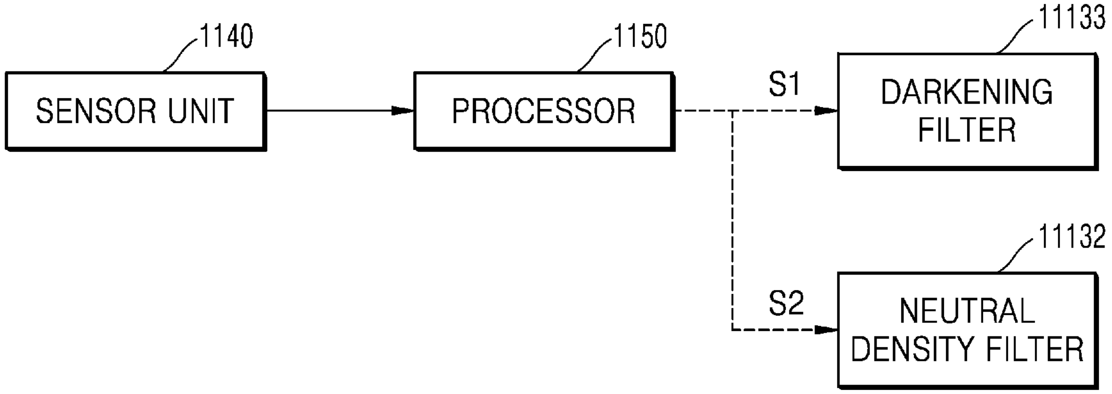
FIG. 7 is a block diagram for describing a method for a processor to control filters.

FIG. 3 is a perspective view of the welding information providing apparatus 1100 according to an embodiment of the present disclosure, and FIG. 4 is a cross-sectional view for describing inside of the welding information providing apparatus 1100 of FIG. 3. FIG. 5 is a diagram illustrating only the configuration of the camera unit 1110 of FIG. 4, and FIG. 6 is a diagram of the camera unit 1110 according to another embodiment. FIG. 7 is a block diagram for describing a method of, by a processor, controlling filters.

Referring to FIGS. 3 and 4, the welding information providing apparatus 1100 of the present disclosure may include the main body 1160, the display unit 1130 installed on the front surface of the main body 1160, the camera unit 1110 installed on the outside of the main body, and the processor 1150. In addition, the welding information providing apparatus 1100 may include at least one sensor unit 1140 (see FIG. 2) and a fixing unit (not shown) that is arranged on a rear surface of the main body 1160 to fix the welding information providing apparatus 1100 on the head of the operator.

According to an embodiment, one or more camera units 1110 may be implemented. When there is one camera unit 1110, the camera unit 1110 may be mounted on the upper end at the center of the main body 1160. In another embodiment, when there are two camera units 1110, the camera units 1110 may be symmetrically mounted on one area of the front portion of the display unit 1130. Here, the front portion of the display unit 1130 may be an external area (the area as shown in FIG. 3) corresponding to the direction in which the welding operation is performed. On the contrary, the rear portion of the display unit 1130 may be an inner area corresponding to a direction toward the face of the operator. However, the present disclosure is not limited thereto, and the camera unit 1110 may be arranged on an external area of the main body 1160, the external area corresponding to the direction in which the welding operation is performed. Also, the camera unit 1110 may be formed to be attachable/detachable so as to change its position as necessary.

In addition, the welding information providing apparatus 1100 of the present disclosure may include a main lens member 1135 for transferring the welding image provided by the display 1132 to both eyes of the user at a short distance.

The welding information providing apparatus 1100 according to an embodiment of the present disclosure provides the welding image via the display 1132 that is spaced a certain distance apart from the user in order to ensure a viewing area of the user. As such, the user may be provided with the welding image from one display, instead of the displays corresponding respectively to both eyes, and thus, a wide field of view may be secured even in a sealed space in the welding information providing apparatus 1100. However, in this case, the welding information providing apparatus 1100 may include the main lens member 1135 in order to clearly provide the user with the welding image provided from the display 1131.

When there is one display 1131 according to the present disclosure, a virtual center line passing a center O1 of the display unit 1130 may be located between both eyes of the user. However, the present disclosure is not limited thereto, and a plurality of displays 1131 may be also arranged at positions that are spaced certain distances from both eyes of the user.

The main lens member 1135 is arranged on a path through which the welding image provided from the display 1131 passes, and may have a convex surface so as to adjust a size of the welding image and guide the welding image to both eyes of the user. The main lens member 1135 may be a convex lens including a convex surface for enlarging the welding image.

The main lens member 1135 may be formed of a glass material, a plastic material, etc. When the main lens member 1135 is formed of the plastic material, a styrene resin including (meth)acrylic resin, allyl carbonate resin such as polycarbonate resin, allyl resin, diethylene glycol bisallyl carbonate resin (CR-39), etc., vinyl resin, polyester resin, polyether resin, urethane resin obtained by reaction of an isocyanate compound with a hydroxy compound such as diethylene glycol, etc., thiourethane resin obtained by reacting an isocyanate compound with a polythiol compound, a transparent resin obtained by curing a polymerizable composition containing a (thio) epoxy compound having at least one disulfide bond in the molecule, etc. may be used. In addition, the main lens member 1135 may be coated with a filter that blocks light of a certain wavelength band. For example, the main lens member 1135 may be a lens coated with a blue light blocking filter.

The main lens member 1135 may be moved back and forth based on an initial position. As described above, the power of the main lens member 1135 is determined in consideration of the user's eyesight, but because the eyesight is different for each user, the welding information providing apparatus 1100 of the present disclosure may provide the welding image having the best image quality by adjusting the distance between the main lens member 1135 and the user. To this end, the welding information providing apparatus 1100 of the present disclosure may further include a distance adjusting member (not shown) for adjusting the distance between the main lens member 1135 and the display 1132.

Like the main lens member 1135, the display unit 1130 may include a separate distance adjusting member to adjust the distance to the main lens member 1135 or to adjust the distance between the display 1131 and the user's eyes. For example, the welding information providing apparatus 1100 may further include a barrel support for fixing the display unit 1130 to one side. The distance adjusting member may move the barrel support back and forth according to manual distance adjustment by the user or automatic distance adjustment. As such, the display unit 1130 may be depressed inside the front portion of the main body 1160 or may protrude to outside of the front portion.

At least one sensor 1140 (or the first sensor) may be mounted on one area of the front portion of the display unit 1130. In another embodiment, the sensor unit 1140 may be included in the main body 1160. Here, the sensor unit 1140 may be mounted in the front direction of the main body 1160 to sense the welding situation.

The main body 1160 protecting the face of the operator may be formed of a material having a certain strength, for example, reinforced plastic, but the present disclosure is not limited thereto, that is, may include various materials having resistance against such elements as sparks that may generate during a welding operation.

The fixing unit (not shown) is an element that comes into direct contact with the head of the operation, and thus, a side surface of the fixing unit (not shown), that is, at least a part of an internal surface coming into direct contact with the head of the operator, may include a soft material such as fiber or cushion material.

Hereinafter, the camera unit 1110 will be described in more detail with reference to the drawings.

Referring back to FIGS. 4 and 5, the camera unit 1110 according to an embodiment of the present disclosure may include a camera module 1112, a filter unit 1113, and a housing 1111.

The camera module 1112 may include a camera housing 11121, a lens assembly 11122, and a substrate assembly 11123.

The camera housing 1121 performs a function of fixing the camera module including the lens assembly 11122 and the substrate assembly 11123. The camera housing 1121 has a through hole in a region corresponding to the lens assembly 11122 so that welding light enters the camera.

The lens assembly 11122 may include an actuator and one or more lenses accommodated therein. The actuator may include an actuator for auto-focusing and/or an actuator for stabilization, and the actuator for auto-focusing and the actuator for stabilization may be integrally provided.

The substrate assembly 11123 may have a structure in which an image sensor IS (see FIG. 6) is coupled to a PCB substrate on which a conductive wiring pattern is formed.

The filter unit 1113 may carry out a function of blocking the welding light generated by the welding operation. The camera unit 1110 may capture a welding image in which a certain amount of welding light is shielded by using the filter unit 1113. The filter unit 1113 may be arranged in front of the camera, in detail, may be located in front of the lens receiving light from a subject.

In an embodiment, the filter unit 1113 may include a darkening filter 11133. The darkening filter 11133 may block the welding light generated when the operator performs the welding operation. That is, the darkening filter 11133 may darken based on the welding light information sensed via the sensor unit 1140, e.g., the optical sensor, and increase the darkening degree of the darkening filter 11133. Here, the darkening filter 11133 may include, for example, a liquid crystal display (LCD) protection panel in which the darkening concentration may be adjusted according to an alignment direction of the liquid crystal. However, the present disclosure is not limited thereto, and the darkening filter 11133 may be implemented with various panels such as vertical align (VA) type LCD, twist nematic (TN) type LCD, in plane switching (IPS) type LCD, etc.

The darkening density of the darkening filter 11133 may be automatically adjusted according to whether there is the welding light or according to intensity of the welding light. As described above, when automatically adjusted according to the brightness of the welding light, the sensor unit 1140 may be used. The optical sensor of the sensor unit 1140 may obtain welding light information by sensing whether there is the welding light or the intensity of the welding light, and may convert information about the intensity of the welding light included in the welding light information into a certain electrical signal. The sensor unit 1140 may transfer the electrical signal to the processor 1150, and the processor 1150 may control the darkening density based on the intensity of the welding light.

That is, the darkening filter 11133 may change the light blocking degree of the panel in real-time to correspond to the intensity of light generated from the welding surface at the welding operation site, and the camera unit 1110 may capture the welding image in which a certain amount of welding light is shielded by the darkening filter 11133 installed on the front portion.

In another embodiment, the filter unit 1113 may further include a neutral density filter 11132. The neutral density filter 11132 may transfer the welding light generated when the operator performing the welding operation to the camera module 1112 after reducing the intensity of the welding light. The neutral density filter 11132 may reduce the intensity of the welding light according to a neutral density set in advance. For example, when the neutral density filter 11132 having the neutral density of 50% is applied, the intensity of the welding light may be further reduced as compared with the case in which the neutral density filter 11132 having the neutral density of 15% is applied.

The filter unit 1113 may have a structure in which the neutral density filter 11132 is replaceable. The operator may use the neutral density filter 11132 of a different neutral density after replacing as necessary.

In another embodiment, the neutral density filter 11132 may be a digital filter, of which the neutral density is controlled by the processor 1150. Like the darkening filter 11133, the neutral density filter 11132, that is, the digital filter, may increase the neutral density based on the welding light information sensed by the sensor unit 1140, e.g., the optical sensor, and may increase the light blocking degree of the neutral density filter 11132.

Here, the neutral density filter 11132 may be located in front of the camera module 1112 to be farther from the camera module 1112 than the darkening filter 11133. Because the darkening filter 11133 has a greater degree of blocking the welding light as compared with the neutral density filter 11132, the camera unit 1110 may block the light by using the neutral density filter 11132 according to the intensity of the welding light, and then, when the intensity of the welding light is large, the camera unit 1110 may block the light by using the darkening filter 11133 or by using both the darkening filter 11133 and the neutral density filter 11132.

Although not shown in the drawings, the filter unit 1113 may further include a bandpass filter. The neutral density filter 11132 or the darkening filter 11133 perform the function of reducing the intensity of the welding light regardless of the wavelength of the light, but the bandpass filter may perform a function of blocking light of a certain wavelength band. When the filter unit 1113 further includes the bandpass filter (not shown), the filter unit 1113 may block ultraviolet ray or infrared ray generated during the welding operation. A bandpass filter (not shown) blocks the infrared and ultraviolet rays, and may be disposed to be the farthest from the face of the operator. The bandpass filter (not shown) may have a dielectric multilayer formed on a surface facing the other filters.

When the welding light is incident from the spark generated during the welding operation of the operator, in the welding light, the infrared ray and the ultraviolet ray are reflected and blocked by the dielectric multilayer of the bandpass filter, and visible light only passes through the bandpass filter and may be irradiated toward the camera module 1112.

The filter unit 1113 may have a protective glass 11131 on a frontmost portion thereof facing the welding light, in order to deal with an accident such as splashing of the spark generated during the welding operation. A coating layer that may prevent fogging or moisture generation by using a hydrophilic coating material may be formed on a front portion of the protective glass 11131. As such, the filter unit 1113 may prevent contaminants from attaching to the filter unit 1113.

In detail, the coating layer formed on the front surface of the protective glass 11131 may be formed of a hydrophilic photocatalytic material such as titanium dioxide ($TiO_2$)

having a self-cleaning performance, in order to prevent adsorption of organic materials around the welding operation.

In addition, the filter unit 1113 may further include a glass portion 11134 disposed between the darkening filter 11133 and the face of the operator. The glass portion 11134 may be directly or indirectly coupled to the darkening filter 11133 so as to prevent the darkening filter 11133 from being damaged due to external foreign matters. The glass portion 11134 may include a transparent material.

In another embodiment, referring to FIG. 6, the filter unit 1113 may be coupled to the camera module 1112 (reference numeral not shown in FIG. 6). The filter unit 1113 may be disposed on a path through which light moves inside the camera module 1112, more specifically, the lens assembly 11122. The filter unit 1113 may be disposed on the front portion from which the lens assembly 11122 receives light, or may be disposed between the lens assembly 11122 and an image sensor IS to block the light. In other words, the filter unit 1113 forms the exterior by using an additional housing, but may be formed to be coupled to the camera module 1112. The filter unit 1113 may be coupled to the front portion of the camera module 1112 or may be disposed between the lens assembly 11122 of the camera module 1112 and the image sensor IS and coupled therebetween. In addition, in another embodiment, the filter 1113 may be integrally formed with the lens assembly of the camera module 1112. The darkening filter 11133 of the filter unit 1113 and the variable neutral density filter 11132 are arranged on an optical axis of a lens L and may be coupled via one housing. In this case, the filter unit 1113 may be formed in a circular shape that is similar to the shape of the lens L. However, the present disclosure is not limited thereto, and the filter unit 1113 may be formed in a different shape from the lens L, for example, a rectangular shape. In this case, the lens assembly 11122 may have a housing with an internal structure capable of accommodating both the circular lens L and the rectangular filter 1113.

In this case, as described above, the filter unit 1113 may include the darkening filter 11133 and may further include the variable neutral density filter 11132 that is a digital neutral density filter. Also, although not shown in the drawings, the filter unit 1113 may further include a bandpass filter.

Hereinafter, a method of controlling the filter unit 1113 by the processor 1150 will be described.

Referring to FIG. 7, the welding information providing apparatus 1100 according to an embodiment of the present disclosure may obtain welding light information by the sensor unit 1140. Here, the sensor unit 1140 includes an optical sensor and may sense whether there is the welding light or the intensity of the welding light. The sensor unit 1140 may convert the presence or intensity of the welding light into an electrical signal and transfer the electrical signal to the processor 1150.

When receiving the electrical signal from the sensor unit 1140, the processor 1150 may generate a control signal and transfer the control signal to the filter unit 1113. Here, the filter unit 1113 of the camera unit 1110 may include the darkening filter 11133 and the neutral density filter 11132 that are controllable. When the welding light is sensed via the sensor unit 1140 and is greater than a first intensity set in advance, the processor 1150 generates a first control signal S1 and a second control signal S2 and may control both the darkening filter 11133 and the neutral density filter 11132 to operate. Also, the processor 1150 may adjust both the darkening density of the darkening filter 11133 and the neutral density filter 11132 according to the sensed intensity of the welding light.

When the welding light is sensed via the sensor unit 1140 and is less than the first intensity and greater than a second intensity set in advance, the processor 1150 may generate the second control signal S2 and control the neutral density filter 11132 only or may generate the first control signal S1 and control the darkening filter 11133 only.

In addition, when the welding light is not sensed via the sensor unit 1140 or is less than the second intensity set in advance, the processor 1150 may not separately control the neutral density filter 11132 or the darkening filter 11133, but transfers the welding light as it is to the camera module 1112.

As described above, the welding information providing apparatus according to one or more embodiments of the present disclosure may obtain the welding image, in which a certain amount of welding light is shielded, without separately processing a captured image by arranging a filter unit that may shield the welding light in front of a camera. Also, the welding information providing apparatus may effectively control a shielding degree by including a darkening filter and a neutral density filter and controlling a darkening density or a neutral density according to whether there is welding light or intensity of the welding light.

Also, the welding information providing apparatus according to one or more embodiments of the present disclosure may have advantages of stably providing the welding image even with the movement such as head shaking, as well as providing the user with comfortable view through the main lens member that provides the welding image from the display to both eyes of the user. In addition, the welding information providing apparatus according to one or more embodiments of the present disclosure may provide the best welding image in correspondence with personal eyesight and adjusting capability by moving the main lens member back and forth or adjusting the angle of the main lens member.

Figure 8:
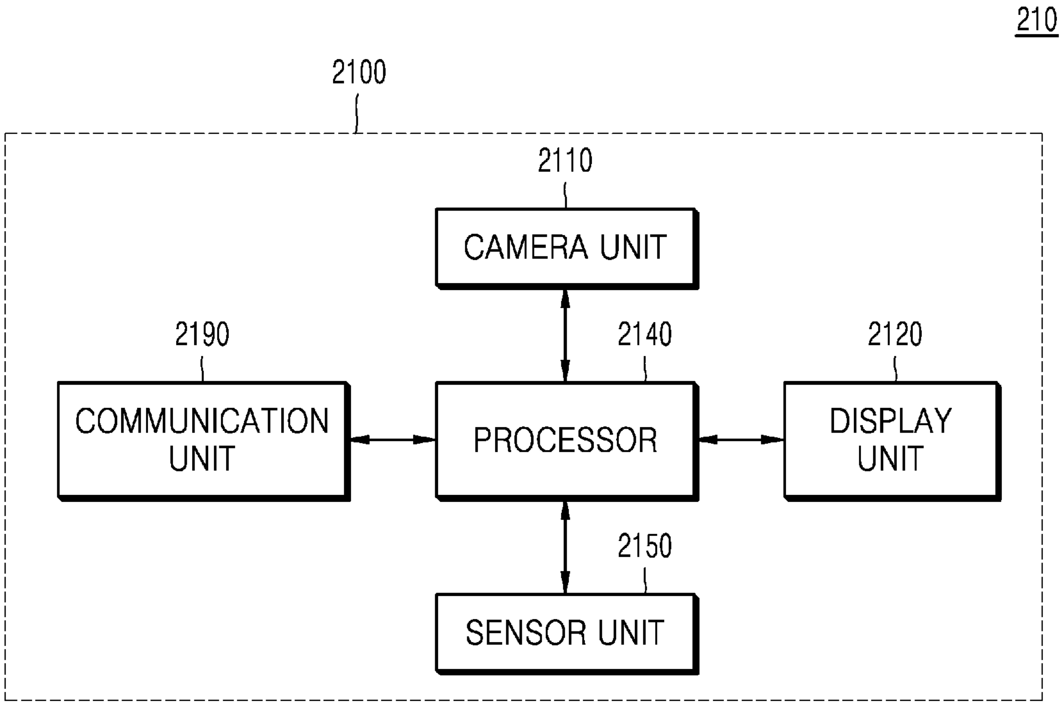
FIG. 8 is a schematic block diagram for describing elements of a welding system according to an embodiment of the present disclosure.
Figure 9:
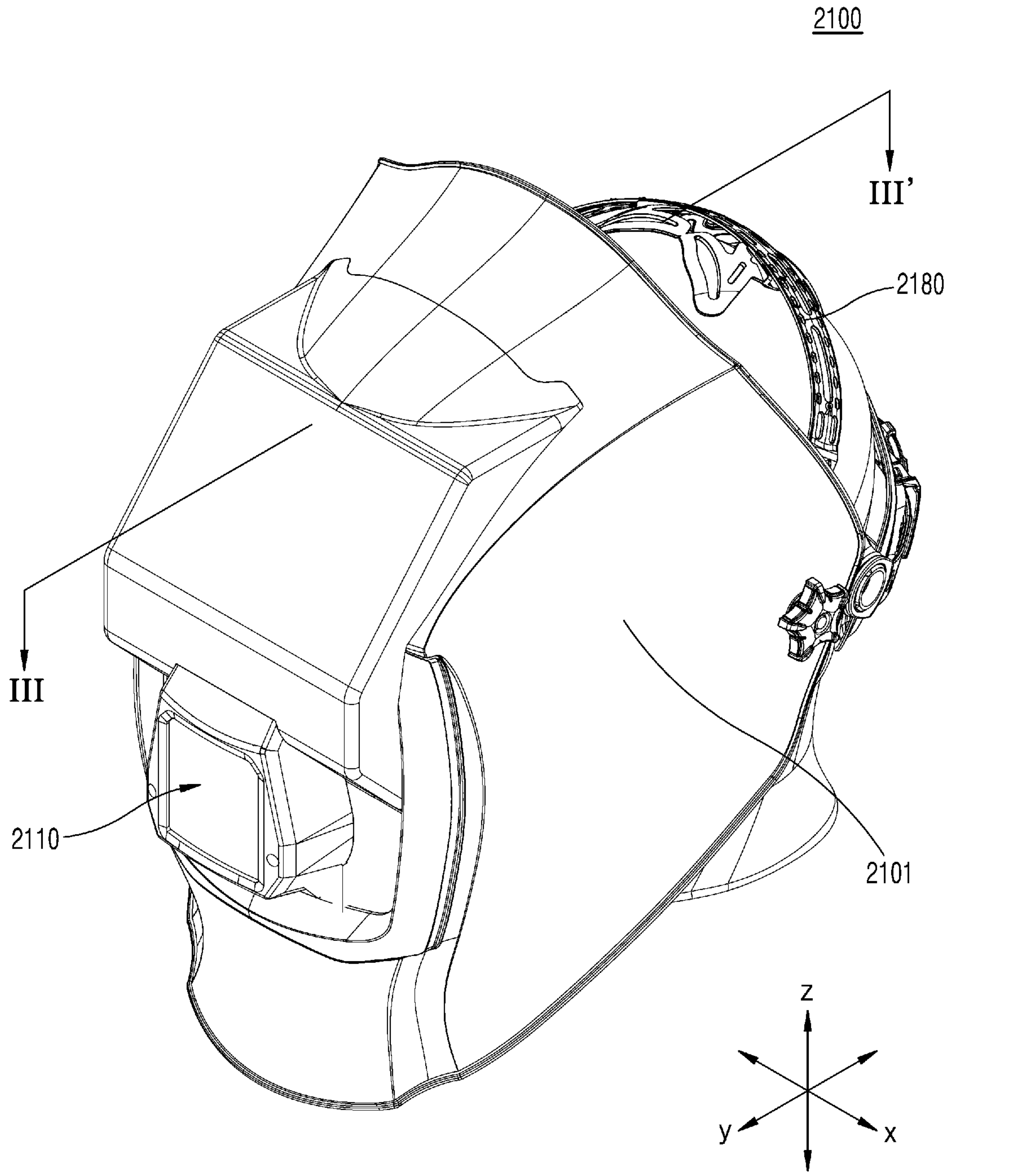
FIG. 9 is a perspective view of a welding information providing apparatus according to an embodiment of the present disclosure.
Figure 10:
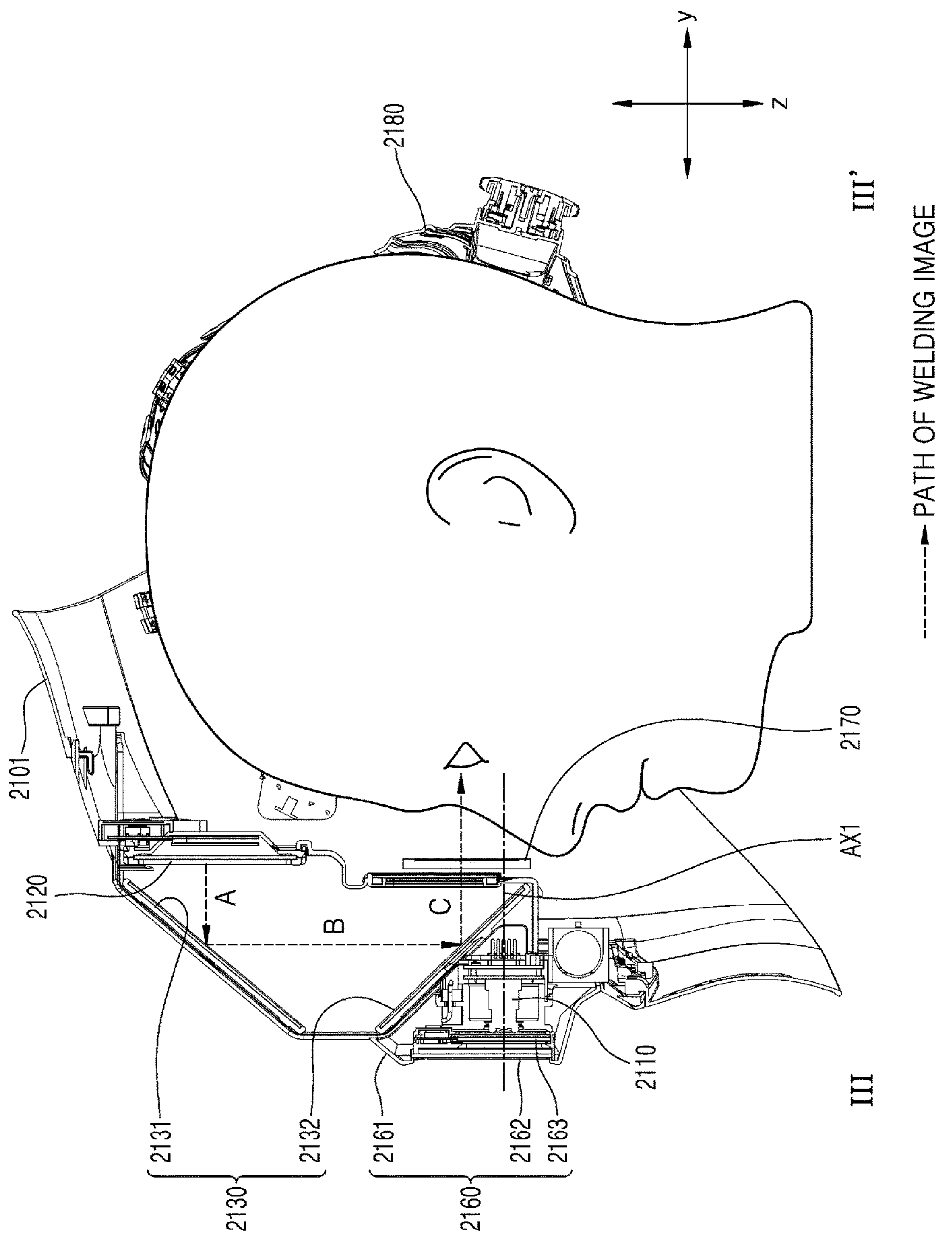
FIG. 10 is a cross-sectional view taken along a line III-III' of FIG. 9.

FIG. 8 is a schematic block diagram for describing elements of a welding system 210 according to an embodiment of the present disclosure, FIG. 9 is a perspective view of a welding information providing apparatus according to an embodiment of the present disclosure, and FIG. 10 is a cross-sectional view taken along line III-III' of FIG. 9.

Referring to FIGS. 8 to 10, the welding system 210 may include a welding information providing apparatus 2100 and a welding torch 2200. The welding information providing apparatus 2100 may include a main body 2101, a camera unit 2110, a display unit 2120, a path change unit 2130, a processor 2140, a sensor unit 2150, and a communication unit 2190.

In addition, the welding information providing apparatus 2100 includes an outer cover unit 2160 for protecting the camera unit 2110, an inner cover unit 2170 arranged between the display unit 2120 and the user, and a fixing unit 2180 arranged on a rear surface of the main body 2101 to fix the welding information providing apparatus 2100 on the head of the user.

The main body 2101 is for protecting the user's face and may be provided to be worn by the user. The main body 2101 may include a material having a predetermined strength, e.g., reinforced plastic, but is not limited thereto, that is, may include various materials having resistance against such elements as sparks that may generate during a welding operation.

The main body 2101 may be fixed to the user's head via the fixing unit 2180 provided inside the main body 2101.

The fixing unit 2180 may have a structure including a plurality of ribs, such as a headgear, and an element including a soft material such as a fiber material or a cushion material may be disposed on at least a portion of an inner surface that is in direct contact with the user's head.

The camera unit 2110 may be mounted on the outside of the main body 2101, and may include at least one camera obtaining a welding image frame of a welding operation. The camera unit 2110 may receive a control command from the processor 2140, and change settings of shutter speed, ISO sensitivity and gain in response to the control command to photograph the welding operation.

In an embodiment, the camera unit 2110 may be located on the front portion of the main body 2101 corresponding to the user's field of view. The camera unit 2110 may include one camera to obtain the welding image frame for the welding operation, but the present disclosure is not limited thereto.

In another embodiment, the camera unit 2110 may include two cameras arranged at positions corresponding respectively to the left and right eyes of the user. In another embodiment, the camera unit 2110 may further include a camera obtaining the welding image frame by photographing at a location other than the front portion of the main body 2101 corresponding to the user's field of view.

The camera unit 2110 may be protected by the outer cover unit 2160. The outer cover unit 2160 may include an outer cover frame 2161, an outer cover plate 2162 and a light blocking cartridge 2163.

The outer cover frame 2161 may couple the outer cover unit 2160 to the main body 2101.

The outer cover plate 2162 may be placed in front of the light blocking cartridge 2163 to protect the light blocking cartridge 2163. The outer cover plate 2162 may include a material through which light may pass, for example, a transparent material. The outer cover plate 2162 may include a resin material such as polycarbonate or acryl, and may be formed through an injection molding.

The light blocking cartridge 2163 may block the welding light generated during welding. That is, the light blocking cartridge 2163 may increase the light blocking degree of the cartridge based on welding light information detected by the sensor unit 2150, for example, a photo sensor. In this case, the light blocking cartridge 2163 may include, for example, a liquid crystal panel (LCD panel), of which a degree of darkening may be adjusted according to the alignment direction of the liquid crystal. For example, the light blocking cartridge 2163 may be implemented with a variety of panels, such as a VA type LCD, TN type LCD, IPS type LCD, etc.

The darkening degree of the light blocking cartridge 2163 may be adjusted automatically according to the brightness of the welding light. As described above, when automatically adjusted according to the brightness of the welding light, the sensor unit 2150 may be used. When the sensor unit 2150 senses the intensity of the welding light to obtain the welding light information and transmits to the processor 2140 that will be described later the information on the intensity of the welding light included in the welding light information as a predetermined electrical signal, the processor 2140 may control the darkening degree based on the intensity of the welding light.

That is, the light blocking cartridge 2163 may change the light blocking degree of the panel in real-time so as to correspond to the intensity of light generated from the welding surface at the welding operation site, and the camera unit 2110 may capture the welding image in which a certain amount of welding light is shielded by the light blocking cartridge 2163 installed in the front portion.

According to another embodiment of the present disclosure, the welding information providing apparatus 2100 may not include the light blocking cartridge 2163. In this case, the user may perform the welding operation only with the welding image obtained through the camera unit 2110.

The camera unit 2110 according to an embodiment of the present disclosure may include a thermal imaging camera. The welding information providing apparatus 2100 may obtain a temperature image by synthesizing a thermal image obtained by thermal imaging camera with an image of a welding site.

According to an embodiment of the present disclosure, a lighting unit (not shown) electrically connected to the processor 2140 may be further provided. The lighting unit (not shown) is located outside the welding information providing apparatus 2100 and is configured to irradiate light toward at least a welding operation area. The lighting unit (not shown) may include a plurality of LED modules, and the output degree of light irradiated through the lighting unit (not shown) may be adjusted by the control of the processor 2140. According to an embodiment, the lighting unit (not shown) may operate in linkage with the operation of the camera unit 2110 under the control of the processor 2140.

The display unit 2120 is arranged in the main body 2101 and may provide the welding image. The display unit 2120 may provide the welding image obtained from the camera unit 2110 as it is, or may provide a high-definition composite image including the welding information.

The display unit 2120 may display the high-definition composite image so that the user may visually confirm the surrounding environment (e.g., pre-worked welding bead, etc.) other than the portion adjacent to the welding light. In addition, the display unit 2120 may guide the user with visual feedback (e.g., welding processing direction) on a welding progress state.

The display unit 2120 may be implemented with various display technologies such as LCD, OLED, LED, LcoS, or DLP.

The display unit 2120 may be arranged in the main body 2101, and may be at a position where the welding image may be indirectly provided by the path change unit 2130 that will be described later, not at a position of directly providing the welding image to the field of view of the user.

In an embodiment, the display unit 2120 may be positioned so that a direction in which the welding image is provided is parallel to an optical axis AX1 of the camera unit 2110. In other words, as illustrated in FIG. 10, the display unit 2120 may be positioned near the user's forehead to provide the welding image toward the path change unit 2130.

The path change unit 2130 may change the path of the welding image provided from the display unit 2120 and guide the path toward the eyes of the user. For example, the path change unit 2130 may be formed of a mirror that reflects the welding image. The path change unit 2130 according to the embodiment of FIG. 10 may include a first mirror 2131 changing the path of the welding image provided from the display unit 2120 (A→B), and a second mirror 2132 changing and guiding the path of the welding image changed from the first mirror 2131 (B→C) to the eyes of the user. Although an example in which the path of the welding image is changed by using two mirrors is shown in the drawings, the present disclosure is not limited thereto, and the path of the welding image may be changed by further including more mirrors or a member capable of changing the path.

Here, the first mirror 2131 and the second mirror 2132 may be made of or coated with a material that reflects the welding image, for example, any one of poly methyl methacrylate (PMMA), poly carbonate (PC), polyester, silver (Ag), and aluminum (Al).

The first mirror 2131 is tilted at an angle of 45° to 50° with respect to the path of the welding image, so that the path of the welding image may be changed vertically. Likewise, the second mirror 2132 is inclined at an angle of 45° to 50° with respect to the welding image path changed by the first mirror 2131, so that the welding image path may be changed vertically. For example, the first mirror 2131 and the second mirror 2132 may be arranged in a line symmetrical relationship based on a center line passing through the path change unit 3130, but the present disclosure is not limited thereto.

The welding image provided from the display unit 2120 may be reversed by being reflected by the first mirror 2131, and then reversed again by the second mirror 2132 and provided to the user. Here, in order to provide the user with the same image as the actual work site, the display unit 2120 has to provide the welding image while upper and lower sides are inverted, and thus, the welding image provided by the display unit 2120 may be an image in which the image obtained through the camera unit 2110 is inverted vertically and horizontally. In another embodiment, when the path change unit 2130 includes more mirrors, in order to provide the user with the same image as the work site, the processor 2140 may change the direction of the image acquired from the camera unit 2110 and transmit the image to the display unit 2120.

Because it is difficult for the human eye to focus on an object that is too close, a clear image may be obtained only by placing the display unit 2120 at the focal length of the field of view. If the display unit 2120 is disposed in front of the user, the size of the welding information providing apparatus 2100 is inevitably increased to ensure such above distance. The welding information providing apparatus 2100 according to an embodiment of the present disclosure may ensure the focal length of the welding image provided from the display unit 2120 through the path change unit 2130 and arrange the display unit 2120 at an appropriate position, thereby configuring compactly the size of the main body 2101.

A distance of a path through which the welding image passes from the display unit 2120 to the eyes of the user through the path change unit 2130 having the above structure may be 200 mm or more. In addition, the user may work at a distance of about 500 mm to 700 mm from the field of view to the site, and when the distance of the path of the welding image provided from the display unit 2120 exceeds 700 mm, a sense of incongruity between the environment in which the user works and the image may occur. Accordingly, the path of the welding image changed through the path change unit 2130 may be determined in a range of 700 mm or less. In other words, the sum of all the paths A, B and C of FIG. 10 may be 200 mm or more and 700 mm or less.

The welding information providing apparatus 2100 may further include an inner cover unit 2170 between the path change unit 2130 and the eyes of the user, that is, on the path through which the welding image passes.

The inner cover unit 2170 may perform a function of preventing foreign substances from infiltrating into the path change unit 2130. Although not shown in the drawings, the inner cover unit 2170 may include an inner cover plate (not shown) and a fixing frame (not shown) for fixing the inner cover plate to the inside of the main body 2101. In addition, the inner cover unit 2170 may have a structure that may further include a lens member such as a magnifying glass according to a user's selection.

The processor 2140 may generate a high-definition composite image by synthesizing the welding image frames received through the camera unit 2110. The processor 2140 may obtain a composite image by setting different photographing conditions for each frame of the camera unit 2110 and synthesizing frames acquired in time-serial order in parallel. In detail, the processor 2140 may control the camera unit 2110 to capture images by changing the shutter speed, ISO sensitivity, and gain of the camera of the camera unit 2110.

Here, the processor 2140 may set different photographing conditions according to conditions such as the welding light sensed from the welding site, ambient light, and the degree of movement of the welding torch 2200. Specifically, the processor 2140 may set the photographing condition to decrease ISO sensitivity and gain as the intensity of the welding light and/or ambient light of the welding site increases. Also, when it is sensed that the movement and/or the working speed of the welding torch 2200 are fast, the photographing condition may be set to increase the shutter speed.

The processor 2140 may synthesize images of a preset number of frames in parallel. According to an embodiment of the present disclosure, each image in the preset frame may be captured under different photographing conditions.

When there are two or more cameras in the camera unit 2110, the processor 2140 according to an embodiment of the present disclosure may control each camera to capture images under different photographing conditions. Even in this case, the processor 2140 may synthesize images of the preset number of frames in parallel.

The processor 2140 may control the overall operation of the welding information providing apparatus 2100 by using various programs stored in a memory (not shown). For example, the processor 2140 may include a CPU, a RAM, a ROM and a system bus. Here, the ROM is an element in which a set of instructions for system booting are stored, and the CPU copies an O/S stored in the memory of the welding information providing apparatus 2100 to the RAM according to the instructions stored in the ROM and executes the O/S to boot the system. When booting is finished, the CPU may copy various applications stored in the memory to the RAM and execute the applications to perform various operations. In the above description, the processor 2140 includes only one CPU, but may be implemented with a plurality of CPUs (or DSPs, SoCs, etc.).

According to an embodiment of the present disclosure, the processor 2140 may be implemented as a DSP, a microprocessor, and/or a TCON for processing a digital signal. However, one or more embodiments are not limited thereto, and the processor may include one or more from a CPU, an MCU, an MPU, a controller, an AP, a CP, and an ARM processor, or may be defined by a corresponding term. In addition, the processor 2140 may be implemented as an SoC or LSI having a processing algorithm built therein, or in the form of an FPGA.

The sensor unit 2150 may include a plurality of sensor modules configured to detect various information on the welding site and obtain welding information. Here, the welding information may include a welding temperature, a welding direction, a welding inclination, a welding speed, a distance between the base material and the welding torch from the real-time welding operation, etc. Furthermore, the sensor unit 2150 may include an optical sensor module configured to detect a light intensity at least within the welding operation area.

According to an embodiment of the present disclosure, the sensor unit 2150 may include an illuminance sensor, and in this case, the sensor unit 2150 may obtain information on the welding light intensity of the welding site. In addition to the illuminance sensor, the sensor unit 2150 may further include various types of sensors such as a proximity sensor, a noise sensor, a video sensor, an ultrasonic sensor and an RF sensor, and may sense various changes related to a welding operation environment.

The communication unit 2190 is an element for receiving welding information from the welding torch 2200 and transmitting a command for controlling the welding torch 2200. According to an embodiment of the present disclosure, the communication unit 2190 may transmit the composite image to an external device other than the welding torch 2200. Here, the external device may include various devices including a communication module, such as a smart phone of an operator/third party, a computer, etc.

The communication unit 2190 may be an element communicating with various types of external devices according to various types of communication methods. The communication unit 2190 may include at least one of a Wi-Fi™ chip, a Bluetooth™ chip, a wireless communication chip, and an NFC chip. In particular, when a Wi-Fi™ chip or a Bluetooth™ chip is used, various connection information such as an SSID, a session key, etc. is transmitted/received first, and then, communication is connected using the above connection information and various information may be transmitted/received. The wireless communication chip refers to a chip that performs communication according to various communication standards such as IEEE (standard-based communication), Zigbee™, 3rd Generation (3G), 3GPP, LTE, etc. The NFC chip refers to a chip operating in a NFC type using a frequency band of 13.56 MHz from among various RF-ID frequency bands such as 135 kHz, 13.56 MHz, 433 MHz, 860 to 960 MHz, 2.45 GHZ, etc.

Although not shown in the drawings, the welding torch 2200 may include a communication unit, a sensor unit, and a second processor.

The communication unit transmits and receives data to/from the welding information providing apparatus 2100. The communication unit includes a module capable of short-range wireless communication (e.g., Bluetooth™, Wi-Fi, Wi-Fi-Direct) or long-distance wireless communication (3G, HSDPA, or LTE).

The sensor unit or the second sensor is an element included in the welding torch for sensing welding conditions such as welding temperature, welding speed, welding slope, welding direction, a distance between the base material and the welding torch, etc.

The sensor unit detects at least one of various changes such as a change in posture of a user holding the welding torch 2200, a change in illuminance of the welding surface, a change in an acceleration of the welding torch 2200, etc., and may transmit an electrical signal corresponding to the change to the second processor. That is, the sensor unit may detect a state change made based on the welding torch, generate a detection signal corresponding thereto, and transmit the sensing signal to the second processor.

In the present disclosure, the sensor unit may include various sensors, and when the welding torch 2200 is driven (or based on a user setting), power is supplied to at least one preset sensor according to control to detect a change in the status of the welding torch 2200.

In this case, the sensor unit may be configured to include at least one of all types of sensing devices capable of detecting a change in the status of the welding torch 2200. For example, the sensor unit may include at least one of various sensing devices such as an acceleration sensor, a gyro sensor, an illuminance sensor, a proximity sensor, a pressure sensor, a noise sensor, a video sensor, a gravity sensor, etc. The degree of light within the welding operation area sensed by the illuminance sensor of the welding torch 2200 may be transferred to the processor 2140 via the communication unit, and the processor 2140 may control the lighting unit (not shown) and/or the camera unit 2110 based on the degree of light transferred through the illuminance sensor of the welding torch 2200, without passing through the sensor unit 2150 of the welding information providing apparatus 2100.

In addition, the acceleration sensor is an element for sensing the movement of the welding torch 2200. In detail, the acceleration sensor may measure a dynamic force such as an acceleration, vibration, or impact of the welding torch 2200, and may measure the movement of the welding torch 2200.

The gravity sensor is an element for sensing a direction of gravity. That is, the detection result of the gravity sensor may be used to determine the movement of the welding torch 2200 along with the acceleration sensor. In addition, the direction in which the welding torch 2200 is gripped may be determined via the gravity sensor.

In addition to the above-described types of sensors, the welding torch 2200 may further include various types of sensors such as a gyroscope sensor, a geomagnetic sensor, an ultrasonic sensor, and an RF sensor, and may detect various changes regarding the welding work environment.

Figure 11:
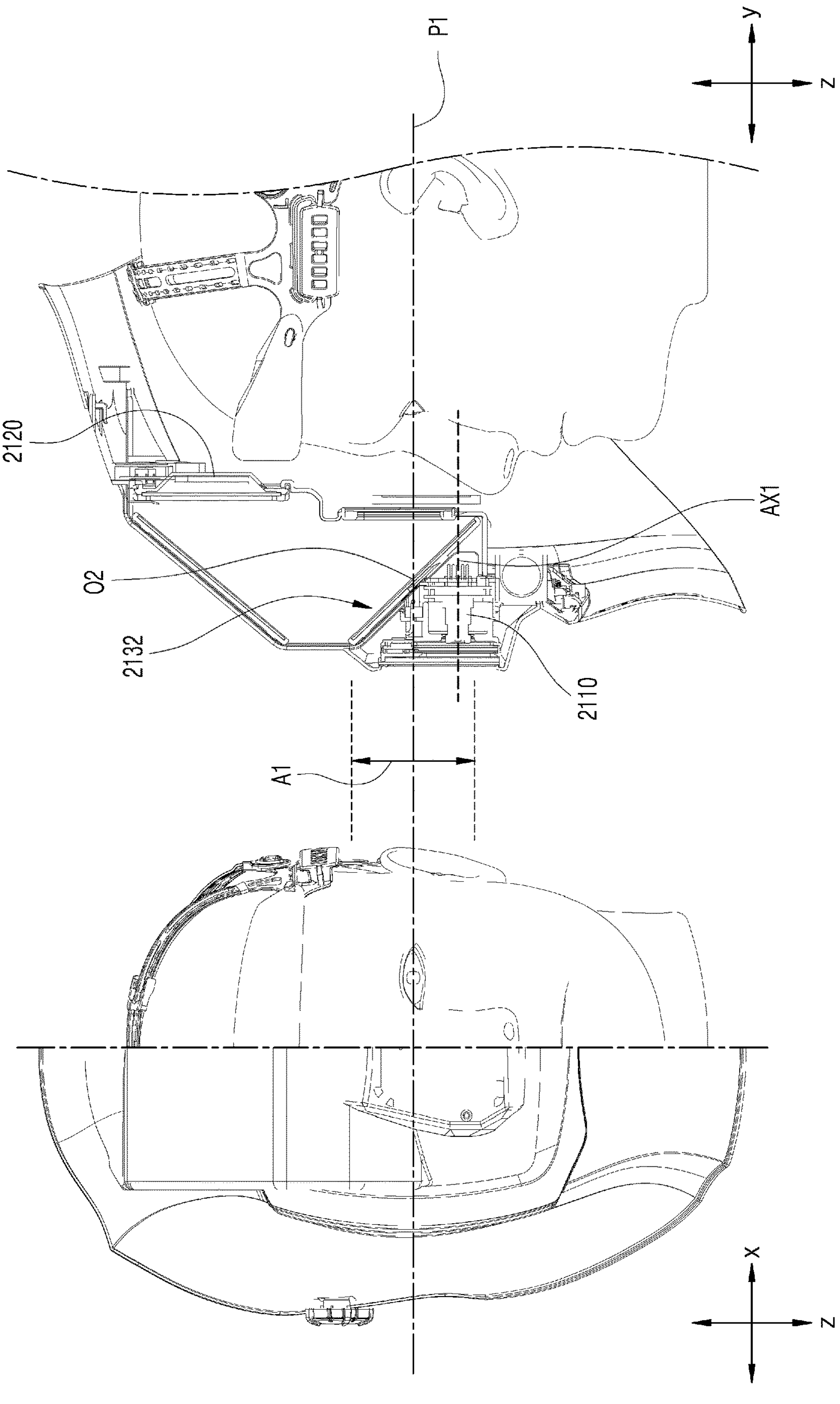
FIGS. 11 and 12 are diagrams for describing a position of a camera unit according to an embodiment of the present disclosure.
Figure 12:
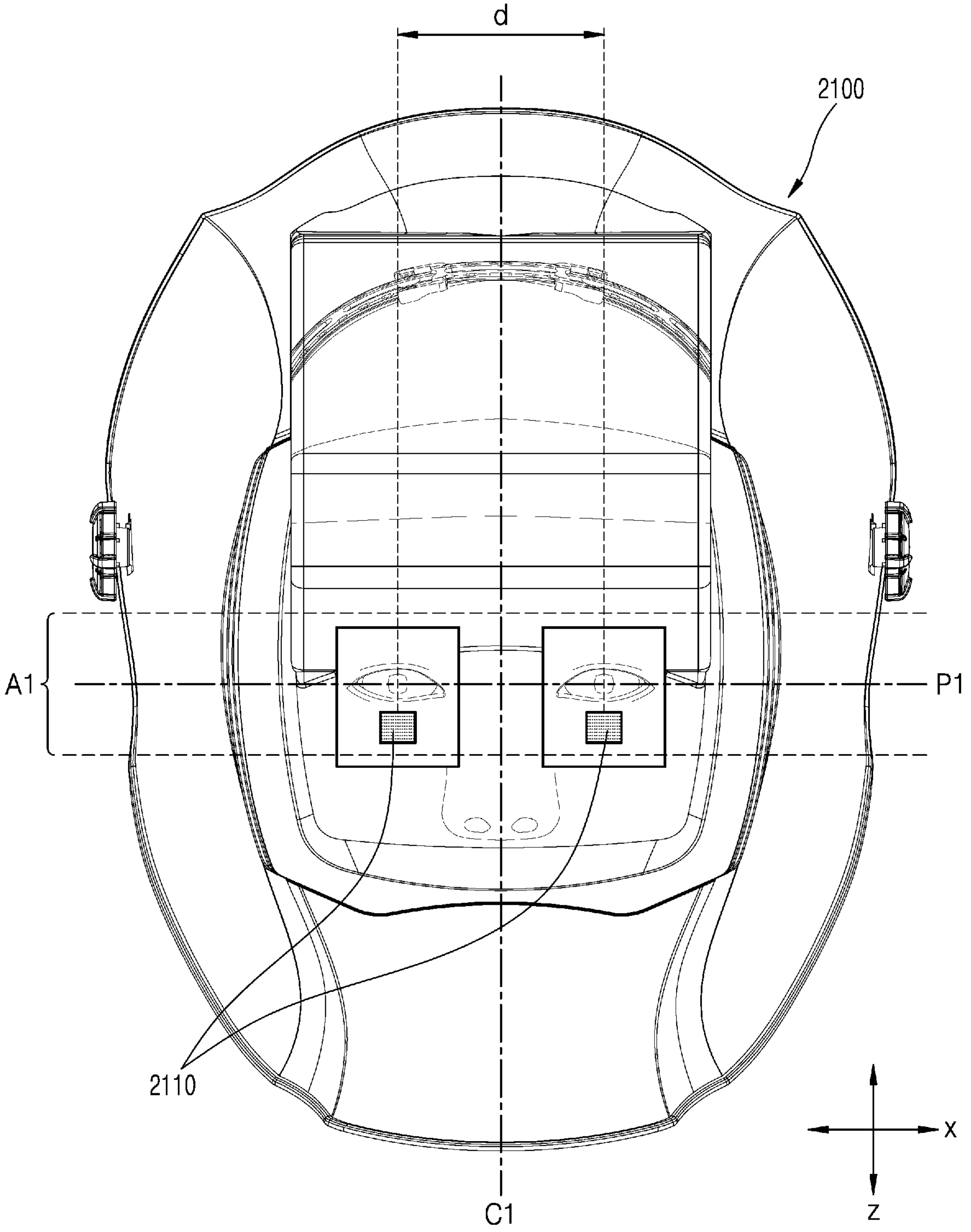

FIGS. 11 and 12 are diagrams for explaining a position of a camera unit according to an embodiment of the present disclosure.

Referring to FIG. 11, a camera unit 2110 according to an embodiment of the present disclosure may be disposed at a position where a virtual extension line extending from an optical axis AX1 of a camera passes through a path change unit 2130.

As an embodiment, the virtual extension line extending from the optical axis AX1 of the camera unit 2110 may pass through a second mirror 2132 of the path change unit 2130. Specifically, the camera unit 2110 may be located within a range A1 of ±30 mm in a vertical direction with respect to an imaginary first surface P1 that is parallel to a path of a welding image from the second mirror 2132 and passes through a center O2 of the second mirror 2132.

In other words, the camera unit 2110 may be disposed on a front portion of a main body 2101 to be positioned at a height similar to a user's field of view, and through this, may obtain the same image as at the user's eye level.

Referring to FIG. 12, as another embodiment, the camera unit 2110 may include two cameras corresponding to each of the user's left and right eyes. The two cameras may be symmetrically disposed with respect to a center line C1 of the main body 2101, and a distance d between the optical axes of each camera may have a value in a range of 60 mm to 70 mm.

As described above, the camera unit may be located within the range A1 of ±30 mm in the vertical direction with respect to the imaginary first surface P1 passing through the center O2 of the second mirror 2132.

Figure 13:
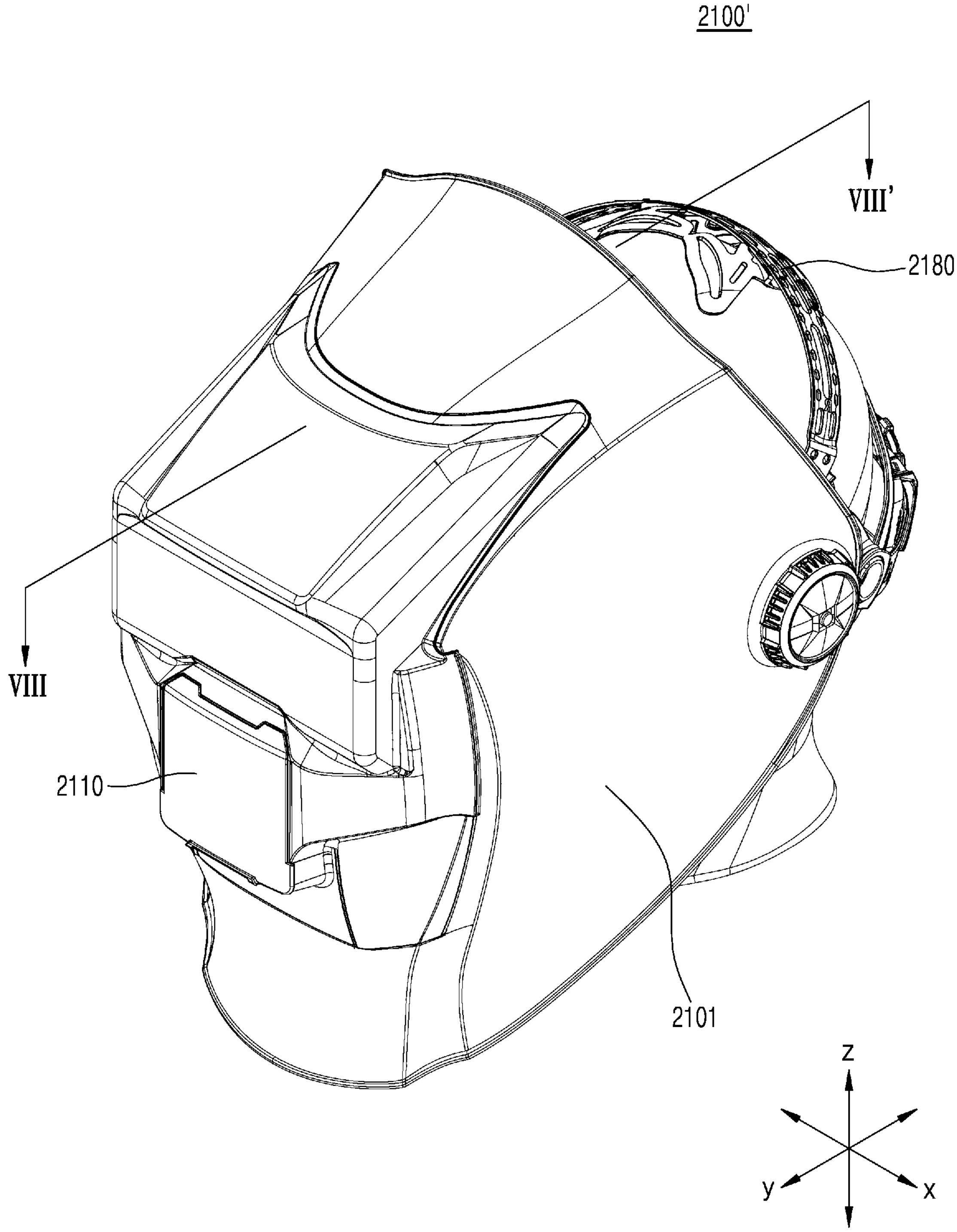
FIG. 13 is a perspective view of a welding information providing apparatus according to another embodiment of the present disclosure.
Figure 14:
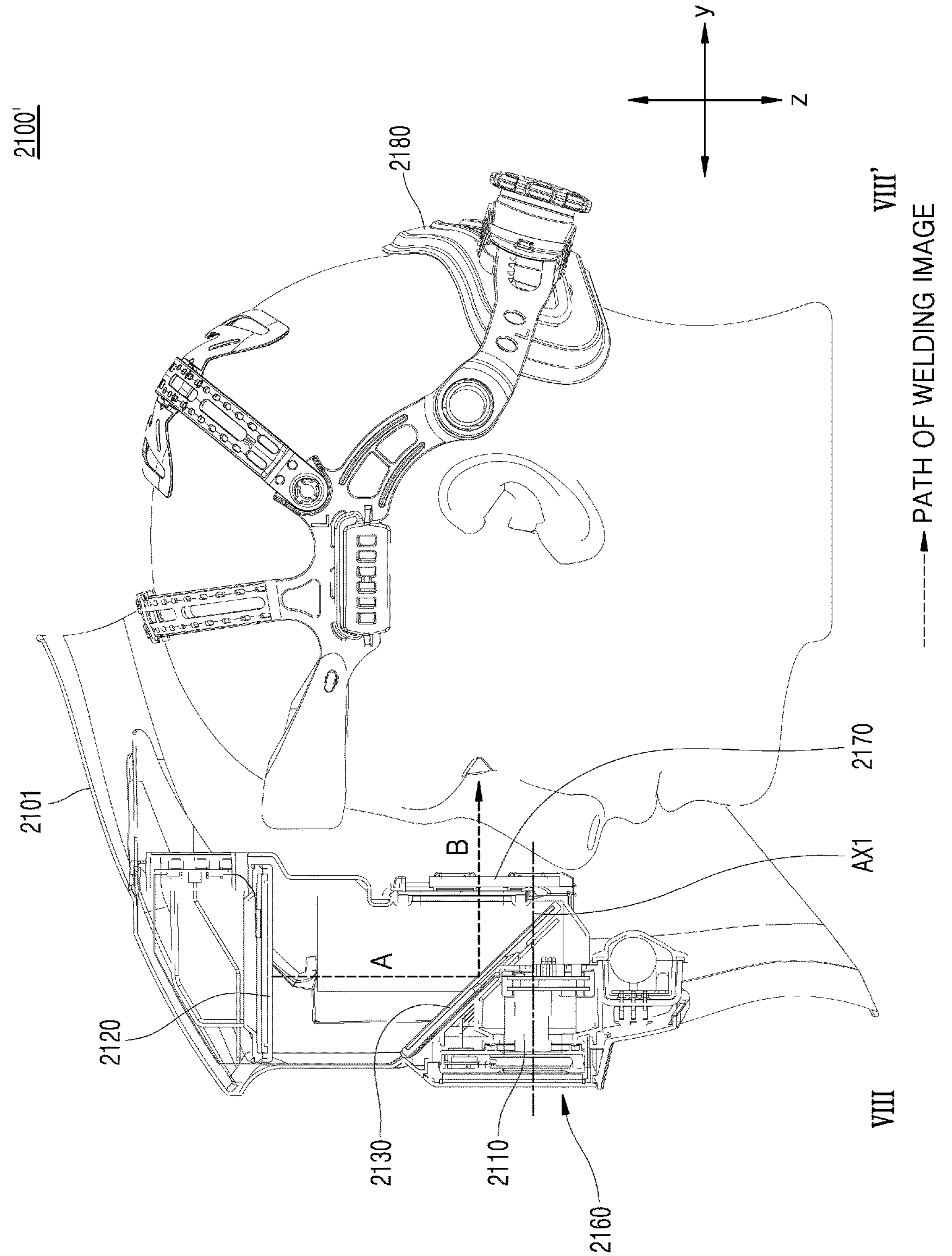
FIG. 14 is a cross-sectional view taken along a line VIII-VIII' of FIG. 13.
Figure 15:
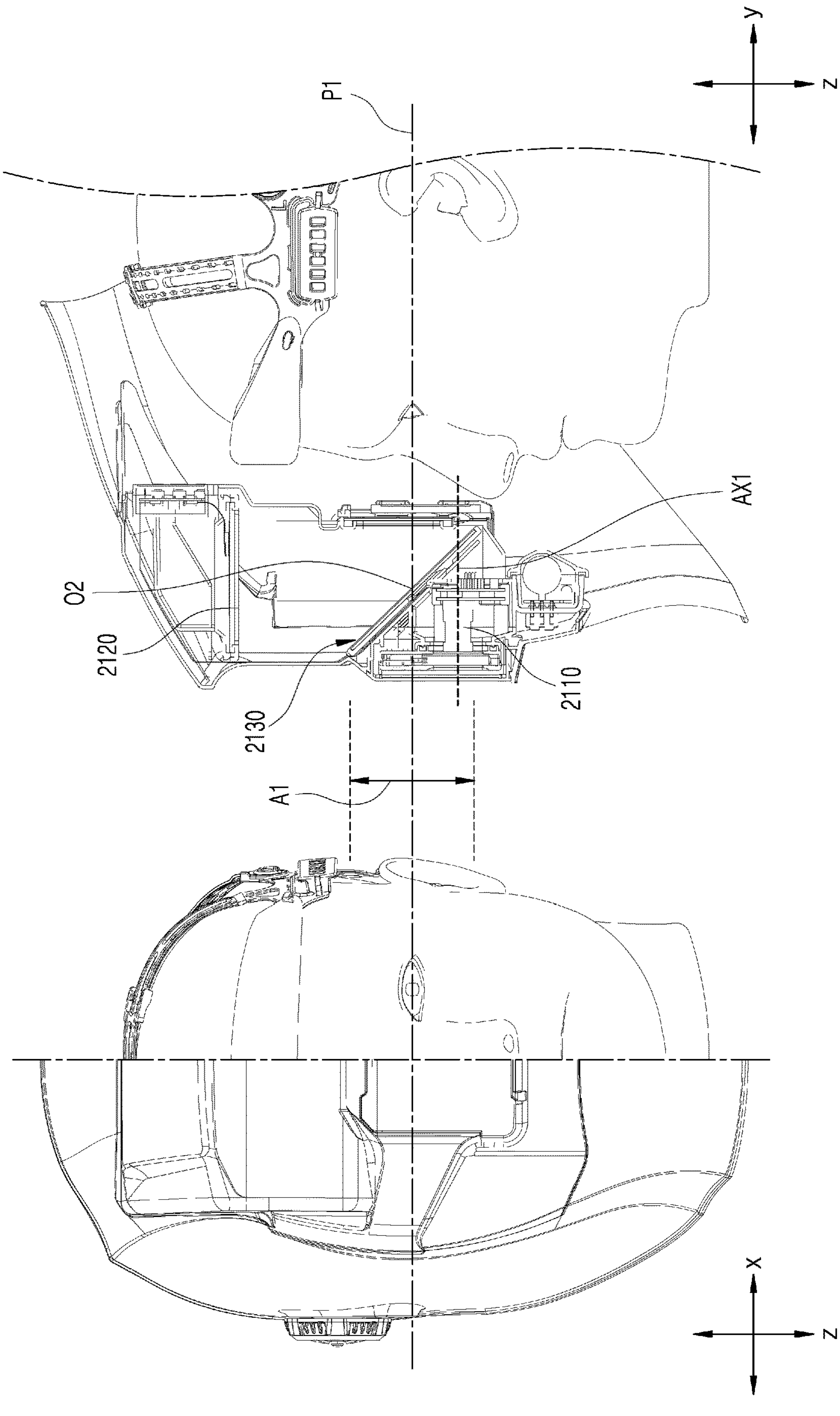
FIG. 15 is a diagram for describing a position of a camera unit according to an embodiment of the present disclosure.

FIG. 13 is a perspective view of a welding information providing apparatus according to another embodiment of the present disclosure, FIG. 14 is a cross-sectional view taken along a line VIII-VIII' of FIG. 13, and FIG. 15 is a diagram for explaining a location of a camera unit according to another embodiment of the present disclosure.

Referring to FIGS. 13 to 15, a welding information providing apparatus 2100' according to another embodiment of the present disclosure may include a main body 2101, a camera unit 2110, a display unit 2120, a path change unit 2130, a processor 2140 (see FIG. 8), a sensor unit 2150 (see FIG. 8) and a communication unit 2190 (see FIG. 8). Another embodiment has the same configuration as the above-described embodiment except that the path change unit 2130 includes one mirror, and thus a redundant description will be omitted.

The main body 2101 is for protecting the user's face and may be provided to be worn by the user. The main body 2101 may be fixed to the user's head through a fixing unit 2180 provided inside the main body 2101.

The camera unit 2110 may be mounted on the outside of the main body 2101, and may include at least one camera acquiring a welding image frame for a welding operation. The camera unit 2110 may receive a control command from the processor 2140, and change settings of shutter speed, ISO sensitivity and gain in response to the control command to photograph the welding operation.

The camera unit 2110 may be disposed at a position where a virtual extension line extending from an optical axis AX1 of a camera passes through the path change unit 2130. The virtual extension line extending from the optical axis AX1 of the camera unit 2110 may pass through the path change unit 2130. Specifically, the camera unit 2110 may be located within a range A1 of ±30 mm in a vertical direction with respect to an imaginary first surface P1 that is parallel to the path of the welding image from the path change unit 2130 and passes through a center O2 of a mirror.

In other words, the camera unit 2110 may be disposed on a front portion of a main body 2101 to be positioned at a height similar to a user's field of view, and through this, may obtain the same image as at the user's eye level.

The camera unit 2110 may be protected by an outer cover unit 2160. The outer cover unit 2160 may include a light blocking cartridge. The light blocking cartridge may block a welding light generated during welding. That is, the light blocking cartridge may increase a light blocking degree of the cartridge based on a welding light information detected through the sensor unit 2150, for example, a photo sensor. In this case, the light blocking cartridge may include, for example, a liquid crystal panel (LCD panel) in which a degree of darkening may be adjusted according to the alignment direction of the liquid crystal. For example, the light blocking cartridge 2163 may be implemented with a variety of panels, such as a vertical align (VA) type LCD, twist nematic (TN) type LCD, in plane switching (IPS) type LCD.

The display unit 2120 is disposed inside the main body 2101 and may provide the welding image. The display unit 2120 may provide the welding image obtained from the camera unit 2110 as it is, or may provide a high-definition composite image including the welding information.

The display unit 2120 may be disposed inside the main body 2101, but may be disposed at a location capable of providing the welding image indirectly by the path change unit 2130 to be described later other than a location capable of providing the welding image directly to the user's field of view.

The display unit 2120 may be positioned so that a direction in which the welding image is provided is perpendicular to the optical axis AX1 of the camera unit 2110. In other words, as illustrated in FIG. 14, the display unit 2120 may be located near the user's forehead to provide the welding image toward the path change unit 2130 located below.

Since the welding image provided from the display unit 2120 is reflected through the one mirror and reversed, the processor 2140 may change the direction of the image obtained from the camera unit 2110 to correspond thereto and provide it to the display unit 2120.

The path change unit 2130 may change the path of the welding image provided from the display unit 2120 and guide the user's eyes. For example, the path change unit 2130 may be formed of the mirror that reflects the welding image. The path change unit 2130 according to the embodiment of FIG. 13 may include the one mirror, and change the path of the welding image provided from the display unit 2120 (A→B) to directly guide the user's eyes.

Here, the path change unit 2130 may be made of or coated with a material that reflects the welding image, for example, any one of poly methyl methacrylate (PMMA), poly carbonate (PC), polyester, silver (Ag), aluminum (Al). The path change unit 2130 is inclined at an angle of 45° to 50° with respect to the path of the welding image to change the path of the welding image vertically.

A distance of a path through which the welding image passes from the display unit 2120 to the user's eye through the path change unit 2130 having the above structure may be 200 mm or more. In addition, the user may work at a distance of about 500 mm to 700 mm from the field of view to the field, and when the distance of the path of the welding image provided from the display unit 2120 exceeds 700 mm, a sense of incongruity between the environment in which the user work and the image may occur. Accordingly, the path of the welding image changed through the path change unit 2130 may be determined in a range of 700 mm or less. In other words, the sum of all the paths A, B and C of FIG. 10 may be 200 mm or more and 700 mm or less.

The welding information providing apparatus 2100' may further include an inner cover unit 2170 between the path change unit 2130 and the user's eyes, that is, on the path through which the welding image passes.

As described above, the welding information providing apparatus according to embodiments of the present disclosure may provide a clear welding image and compact size of the main body by changing the path of the welding image through the path change unit and providing it to the user. In addition, the welding information providing apparatus according to embodiments of the present disclosure acquires the image through the camera unit disposed at the height similar to the user's field of view, thereby providing the welding image with minimal sense of incongruity or foreignness with an actual work site to the user.

Figure 16:
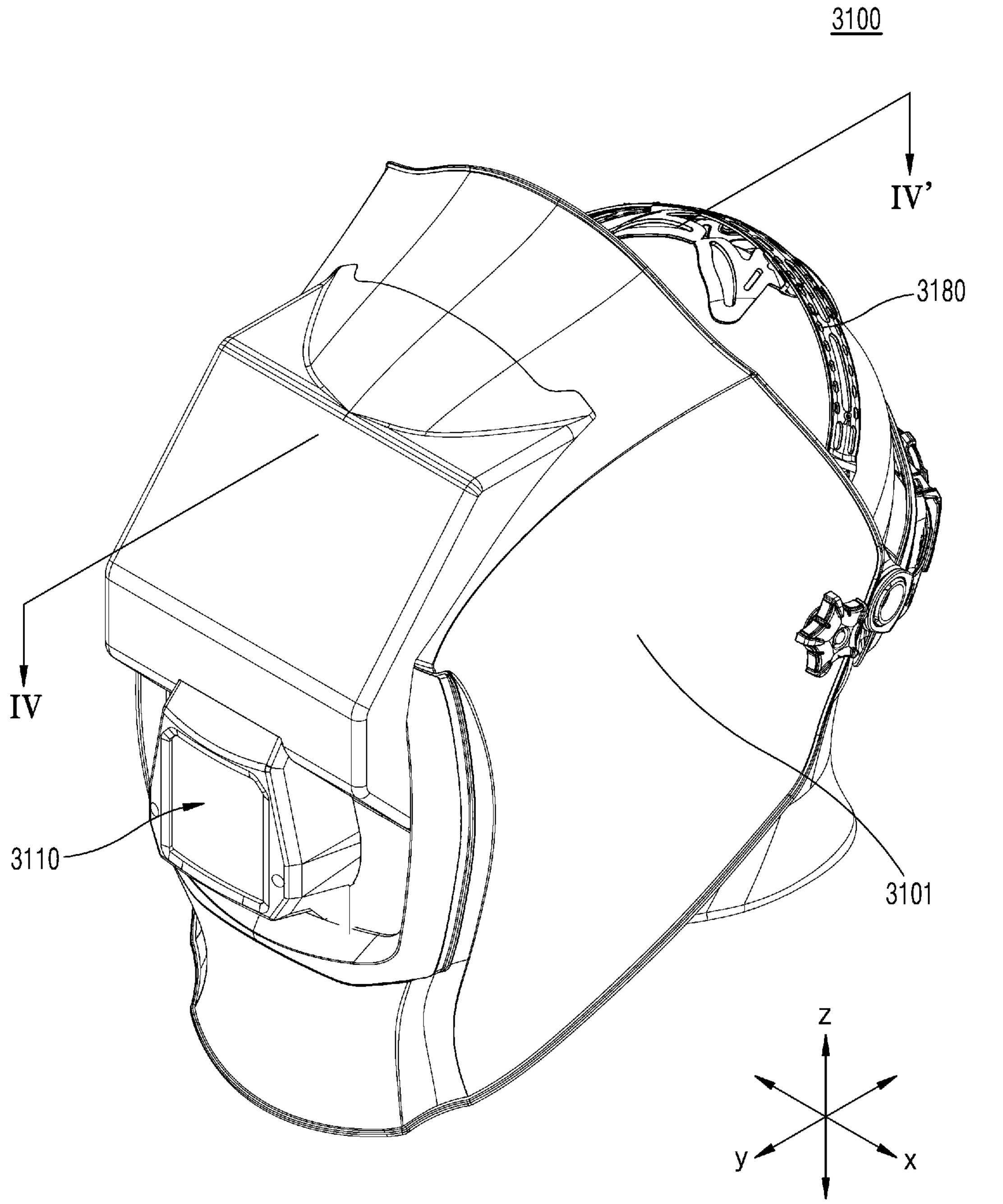
FIG. 16 is a perspective view of a welding information providing apparatus according to another embodiment of the present disclosure.
Figure 17:
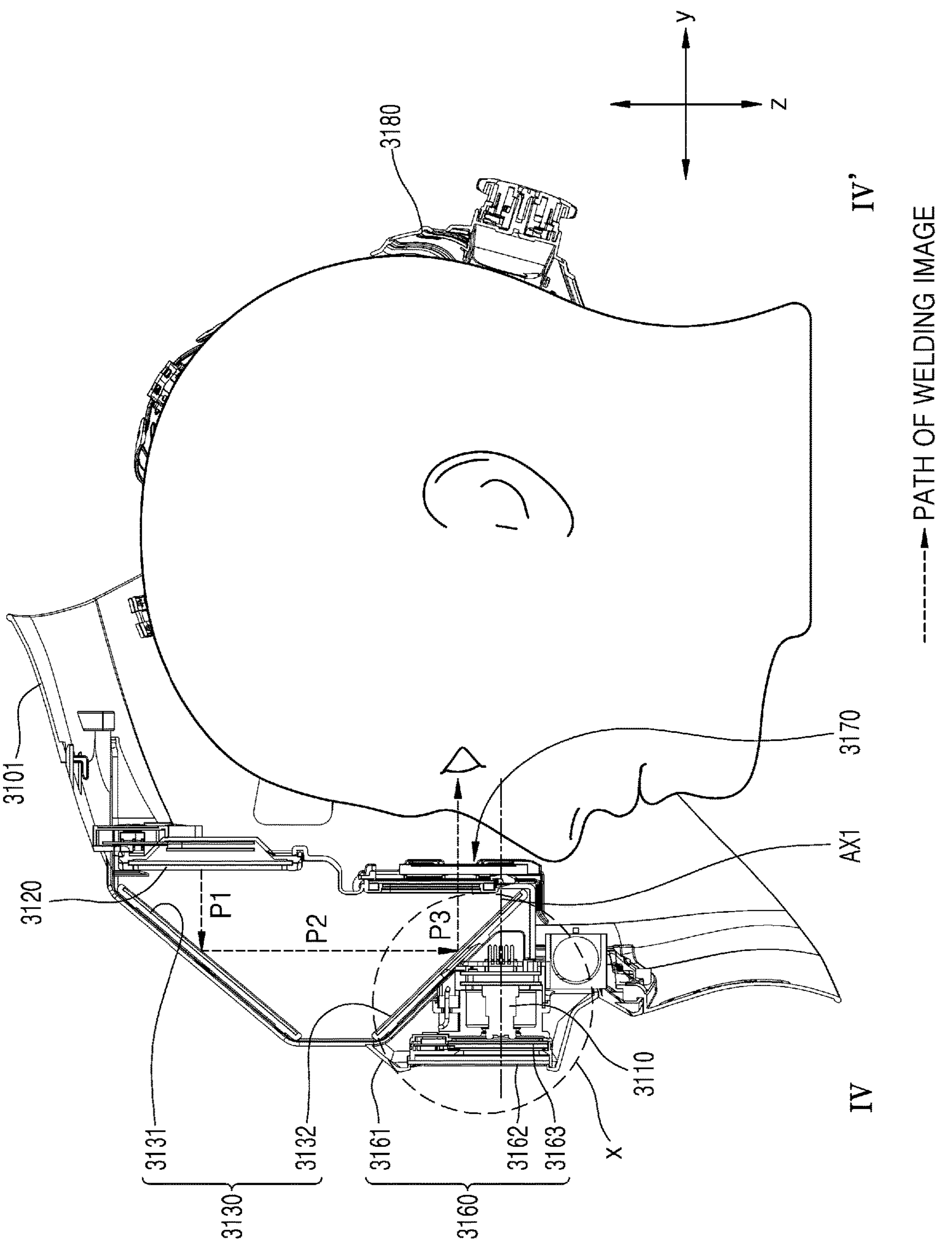
FIG. 17 is a cross-sectional view taken along a line IV-IV' of FIG. 16.

FIG. 16 is a perspective view of a welding information providing apparatus according to another embodiment of the present disclosure. FIG. 17 is a cross-sectional view taken along line IV-IV' of FIG. 16, and FIG. 18 is an enlarged view of X of FIG. 17.

Figure 18:
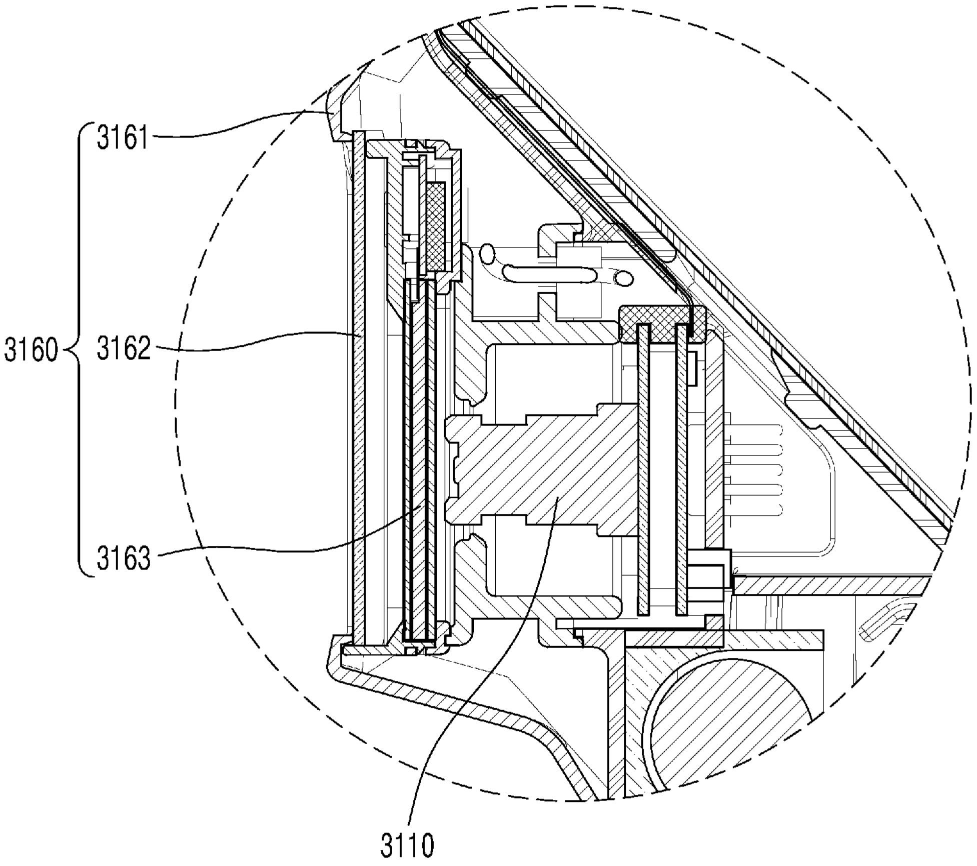
FIG. 18 is an enlarged view of X of FIG. 17.

Referring to FIGS. 16 to 18, a welding system 310 may include a welding information providing apparatus 3100 and a welding torch 3200. The welding information providing apparatus 3100 may include a main body 3101, a camera unit 3110, a display unit 3120, a path change unit 3130, a processor 3140, a sensor unit 3150 and a communication unit 3190.

For example, the welding information providing apparatus 3100 may include the main body 3101 provided to be worn by a user, the camera unit 3110 including at least one camera mounted on an outside of the main body 3101 and obtaining a welding image frame for a welding operation, an outer cover unit 3160 including an outer cover frame 3161 coupled to the main body and an outer cover plate 3162 provided in the outer cover frame 3161 and disposed in front of the camera to protect the camera, the display unit 3120 disposed inside the main body 3101 and providing a welding image generated based on the welding image frame, and the path change unit 3130 for changing the path of the welding image provided from the display unit and guiding it to the user's eyes. In addition, the welding information providing apparatus 3100 may include an inner cover unit 3170 disposed between the display unit 3120 and the user, and a fixing unit 3180 disposed on the rear surface of the main body 3101 to fix the welding information providing apparatus 3100 to the user's head.

The main body 3101 may be fixed to the user's head through the fixing unit 3180 provided inside the main body 3101. The fixing unit 3180 may have a structure including a plurality of ribs, such as a headgear, and an element including a soft material such as a fiber material or a cushion material may be disposed on at least a portion of an inner surface in direct contact with the user's head.

The camera unit 3110 is mounted on the outside of the main body 3101 and may include the at least one camera acquiring the welding image frame for the welding operation. The camera unit 3110 may receive a control command from the processor 3140 and change settings of shutter speed, ISO sensitivity, and gain in response to the control command to photograph the welding operation.

As an embodiment, the camera unit 3110 may be located on the front portion of the main body 3101 corresponding to the user's field of view. The camera unit 3110 may include one camera to obtain the welding image frame for the welding operation, but the present disclosure is not limited thereto.

As another embodiment, the camera unit 3110 may arrange two cameras at positions corresponding to each of the user's left and right eyes. As another embodiment, the camera unit 3110 may further include a camera acquiring the welding image frame by photographing at a location other than the front portion of the main body 3101 corresponding to the user's field of view.

The camera unit 3110 may be protected by the outer cover unit 3160. The outer cover unit 3160 may include the outer cover frame 3161, the outer cover plate 3162 and a light blocking cartridge 3163.

The outer cover frame 3161 may couple the outer cover unit 3160 to the main body 3101. For example, the outer cover plate 3162 may be coupled to the outer cover frame 3161, the outer cover frame 3161 may be coupled to the main body 3101, and eventually the outer cover unit 3160 including the outer cover plate 3162 may be coupled to the main body 3101.

The outer cover plate 3162 may be placed in front of the camera to protect the camera. That is, since the camera that captures a welding operation image is disposed on the outside of the main body 3101, the outer cover plate 3162 is disposed in front of the camera to prevent the camera from being damaged by an external environment.

As an optional embodiment, the outer cover plate 3162 may be attachable to and detachable from the outer cover frame 3161. Since the outer cover plate 3162 is placed in front of the camera, a surface may be damaged by the external environment. In this case, the outer cover plate 3162 is configured to be attachable to and detachable from the outer cover frame 3161, so that a damaged outer cover plate 3162 may be replaced. However, the present invention is not limited thereto, and of course, the outer cover plate 3162 may be formed integrally with the outer cover frame 3161.

The outer cover plate 3162 may be placed in front of the light blocking cartridge 3163 to protect the light blocking cartridge 3163. The outer cover plate 3162 may include a material through which light may pass, for example, a transparent material. The outer cover plate 3162 may include a resin material such as polycarbonate or acrylic, and may be molded by injection molding. In this case, the welding operation image may be moved in the order of the outer cover plate 3162, the light blocking cartridge 3163 and the camera.

The light blocking cartridge 3163 may block the welding light generated during welding. That is, the light blocking cartridge 3163 may increase the light blocking degree of the cartridge based on a welding light information detected by the sensor unit 3150, for example, a photo sensor. In this case, the light blocking cartridge 3163 may include, for example, a liquid crystal panel (LCD panel) whose degree of darkening may be adjusted according to the alignment direction of the liquid crystal. For example, the light blocking cartridge 3163 may be implemented with various panels such as vertical align (VA) type LCD, twist nematic (TN) type LCD and in plane switching (IPS) type LCD.

The degree of darkening of the light blocking cartridge 3163 may be adjusted automatically according to the brightness of the welding light. As described above, when automatically adjusted according to the brightness of the welding light, the sensor unit 3150 may be used. The sensor unit 3150 detects the intensity of the welding light to obtain welding light information, and transmits the information on the intensity of the welding light included in the welding light information as a predetermined electrical signal to the processor 3140 to be described later, the processor 3140 may control the degree of darkening based on the intensity of the welding light.

That is, the light blocking cartridge 3163 may change the light blocking degree of the panel in real time to correspond to the intensity of light generated from the welding surface at the welding operation site, and the camera unit 3110 may capture the welding image in which a certain amount of welding light is shielded by the light blocking cartridge 3163 installed in the front portion.

According to another embodiment of the present disclosure, the welding information providing apparatus 3100 may not include the light blocking cartridge 3163. In this case, the user may perform the welding operation only with the welding image acquired through the camera unit 3110.

The camera unit 3110 according to an embodiment of the present disclosure may include a thermal image camera. The welding information providing apparatus 3100 may acquire a temperature image by synthesizing a thermal image acquired through the thermal image camera with an image about a welding site.

An embodiment of the present disclosure may further include a lighting unit (not illustrated) electrically connected to the processor 3140. The lighting unit (not illustrated) is located outside the welding information providing apparatus 3100 and is configured to irradiate light toward at least a welding operation area. The lighting unit (not illustrated) may include a plurality of LED modules, and the output of light irradiated through the lighting unit (not illustrated) may be adjusted by the processor 3140. According to an embodiment, the lighting unit (not illustrated) may operate in conjunction with the operation of the camera unit 3110 under the control of the processor 3140.

The display unit 3120 is disposed inside the main body 3101 and may provide a welding image. The display unit 3120 may provide the welding image obtained from the camera unit 3110 as it is, or may provide a high-definition composite image including welding information.

The display unit 3120 may display the high-definition composite image so that the user may visually confirm the surrounding environment (e.g., pre-worked welding bead, etc.) other than the portion adjacent to the welding light. In addition, the display unit 3120 may guide the user with a visual feedback (e.g., welding progress direction) on a welding progress state.

The display unit 3120 may be implemented with various display technologies such as liquid crystal display (LCD), organic light emitting diodes (OLED), light-emitting diode (LED), liquid crystal on silicon (LcoS) or digital light processing (DLP).

The display unit 3120 may be disposed inside the main body 3101, but may be disposed at a location capable of providing the welding image indirectly by the path change unit 3130 to be described later other than a location capable of providing the welding image directly to the user's field of view.

As an embodiment, the display unit 3120 may be positioned so that a direction in which the welding image is provided is parallel to an optical axis AX1 of the camera unit 3110. In other words, as illustrated in FIG. 17, the display unit 3120 may be positioned near the user's forehead to provide the welding image toward the path change unit 3130.

The path change unit 3130 may change the path of the welding image provided from the display unit 3120 and guide the user's eyes. For example, the path change unit 3130 may be formed of a mirror that reflects the welding image. The path change unit 3130 according to the embodiment of FIG. 17 may include a first mirror 3131 changing the path of the welding image provided from the display unit 3120 (P1→P2), and a second mirror 3132 guiding the user's eyes by changing the path of the welding image changed from the first mirror 3131 (P2→P3). Although the drawing illustrates a case in which the path of the welding image is changed by two mirrors, the technical spirit of the present disclosure is not limited thereto, and the path of the welding image may be changed by further including more mirrors or a member capable of changing the path.

Here, the first mirror 3131 and the second mirror 3132 may be made of or coated with a material that reflects the welding image, for example, any one of poly methyl methacrylate (PMMA), poly carbonate (PC), polyester, silver (Ag), aluminum (Al).

The first mirror 3131 is tilted at an angle of 45° to 50° with respect to the path of the welding image, so that the path of the welding image may be changed vertically. Similarly, the second mirror 3132 is inclined at an angle of 45° to 50° with respect to the welding image path changed by the first mirror 3131, so that the welding image path may be changed vertically. For example, the first mirror 3131 and the second mirror 3132 may be disposed in a line symmetrical relationship with respect to a center line passing through the path change unit 3130, but the present disclosure is not limited thereto.

The welding image provided from the display unit 3120 may be reversed by being reflected by the first mirror 3131, and then reversed by the second mirror 3132 and provided to the user. At this time, in order to provide the user with the same image as the actual work site, the display unit 3120 has to provide the welding image in a state in which the upper and lower images inverted, so the welding image provided by the display unit 3120 may be an in which the image obtained through the camera unit 3110 is inverted vertically and horizontally. As another embodiment, when the path change unit 3130 includes more mirrors, in order to provide the user with the same image as the work site, the processor 3140 may change the direction of the image acquired from the camera unit 3110 and transmit it to the display unit 3120.

Since it is difficult for the human eye to focus on an object that is too close, a clear image may be obtained only by placing the display unit 3120 at the focal length of the field of view. If the display unit 3120 is disposed in front of the user, the size of the welding information providing apparatus 3100 is inevitably increased to ensure such the distance. The welding information providing apparatus 3100 according to an embodiment of the present disclosure may ensure the focal length of the welding image provided from the display unit 3120 through the path change unit 3130 and arrange the display unit 3120 at an appropriate position, thereby configuring compactly the size of the main body 3101.

A distance of a path through which the welding image passes from the display unit 3120 to the user's eye through the path change unit 3130 having the above structure may be 200 mm or more. In addition, the user may work at a distance of about 500 mm to 700 mm from the field of view to the field, and when the distance of the path of the welding image provided from the display unit 3120 exceeds 700 mm, a sense of incongruity between the environment in which the user work and the image may occur. Accordingly, the path of the welding image changed through the path change unit 3130 may be determined in a range of 700 mm or less. In other words, the sum of all paths P1, P2 and P3 of FIG. 17 may be 200 mm or more and 700 mm or less.

The welding information providing apparatus 3100 may further include an inner cover unit 3170 between the path change unit 3130 and the user's eyes, that is, on the path through which the welding image passes.

The inner cover unit 3170 may prevent foreign substances from penetrating into the path change unit 3130. Although not illustrated, the inner cover unit 3170 may include an inner cover plate (not illustrated) and a fixing frame (not illustrated) for fixing the inner cover plate to the inside of the main body 3101. In addition, the inner cover unit 3170 may have a structure that may further include a lens member such as a magnifying glass according to a user's selection.

The processor 3140 may generate a high-definition composite image by synthesizing the welding image frame received through the camera unit 3110. The processor 3140 may obtain a composite image by setting different shooting conditions for each frame of the camera unit 3110 and synthesizing frames acquired in time order in parallel. Specifically, the processor 3140 may control the camera unit 3110 to take pictures by changing the shutter speed, ISO sensitivity, and gain of the camera of the camera unit 3110.

In this case, the processor 3140 may set different shooting conditions according to conditions such as the sensed welding site's welding light, ambient light and the degree of movement of the welding torch 3200. Specifically, the processor 3140 may set the shooting condition to decrease ISO sensitivity and gain as the welding light and/or ambient light of the welding site increases. In addition, when the movement and/or operation speed of the welding torch 3200 is detected to be fast, the shooting condition may be set to increase the shutter speed.

The processor 3140 may synthesize images of a preset number of frames in parallel. According to an embodiment of the present disclosure, each image in the preset frames may be photographed under different shooting conditions.

When there are two or more cameras of the camera unit 3110, the processor 3140 according to an embodiment of the present disclosure may control to shoot by differently setting the shooting setting conditions for each camera. Even in this case, the processor 3140 may synthesize images of the preset number of frames in parallel.

The processor 3140 may control the overall operation of the welding information providing apparatus 3100 by using various programs stored in a memory (not illustrated). For example, the processor 3140 may include a CPU, a RAM, a ROM and a system bus. Here, the ROM stores a command set for booting a system, and the CPU copies an operating system stored in the memory of the welding information providing apparatus 3100 to the RAM according to the commands stored in the ROM and executes the operating system to boot the system. When booting is complete, the CPU may perform various operations by copying various applications stored in memory to the RAM and executing them. In the above description, the processor 3140 includes only one CPU, but may include a plurality of CPUs (or DSPs, SoCs, etc.).

According to an embodiment of the present disclosure, the processor 3140 may be implemented as a digital signal processor (DSP), a microprocessor, and/or a time controller (TCON) for processing a digital signal. However, it is not limited thereto, and the processor includes one or more of a central processing unit (CPU), a micro controller unit (MCU), a micro processing unit (MPU), a controller, an application processor (AP), a communication processor (CP) or an ARM processor, or may be defined by a corresponding term. In addition, the processor 3140 may be implemented as a system on chip (SoC) having a built-in processing algorithm, large scale integration (LSI), or a field programmable gate array (FPGA).

The sensor unit 3150 may include a plurality of sensor modules configured to detect various information on the welding site and obtain welding information. In this case, the welding information may include a welding temperature, a welding direction, a welding slope, a welding speed, and an interval between a base material and a welding torch for a real-time welding operation. Furthermore, the sensor unit 3150 may include an optical sensor module configured to detect a light intensity at least within the welding operation area.

According to an embodiment of the present disclosure, the sensor unit 3150 may include an illuminance sensor, and in this case, the sensor unit 3150 may obtain information on the welding light intensity of the welding site. In addition to the illuminance sensor, the sensor unit 3150 may further include various types of sensors such as a proximity sensor, a noise sensor, a video sensor, an ultrasonic sensor and an RF sensor, and may detect various changes related to a welding operation environment.

The communication unit 3190 is configured to receive welding information from the welding torch 3200 and transmit a command for controlling the welding torch 3200. According to an embodiment of the present disclosure, the communication unit 3190 may transmit the composite image to an external device other than the welding torch 3200. In this case, the external device may include various devices including a communication module, such as a user/third party's smart phone or computer.

The communication unit 3190 may be configured to communicate with various types of external devices according to various types of communication methods. The communication unit 3190 may include at least one of a Wi-Fi™ chip, a Bluetooth™ chip, a wireless communication chip, and an NFC chip. In particular, in the case of using a Wi-Fi™ chip or a Bluetooth™ chip, various types of connection information such as an SSID and a session key are first transmitted and received, and then various types of information may be transmitted and received after communication connection by using the same. The wireless communication chip refers to a chip that performs communication according to various communication standards such as IEEE (standard-based communication), Zigbee™, 3rd generation (3G), 3rd generation partnership project (3GPP), and long term evolution (LTE). The NFC chip refers to a chip operating in near field communication (NFC) method using the 13.56 MHz band among various RF-ID frequency bands such as 135 kHz, 13.56 MHz, 433 MHz, 860~960 MHz, 2.45 GHZ, etc.

Figure 19:
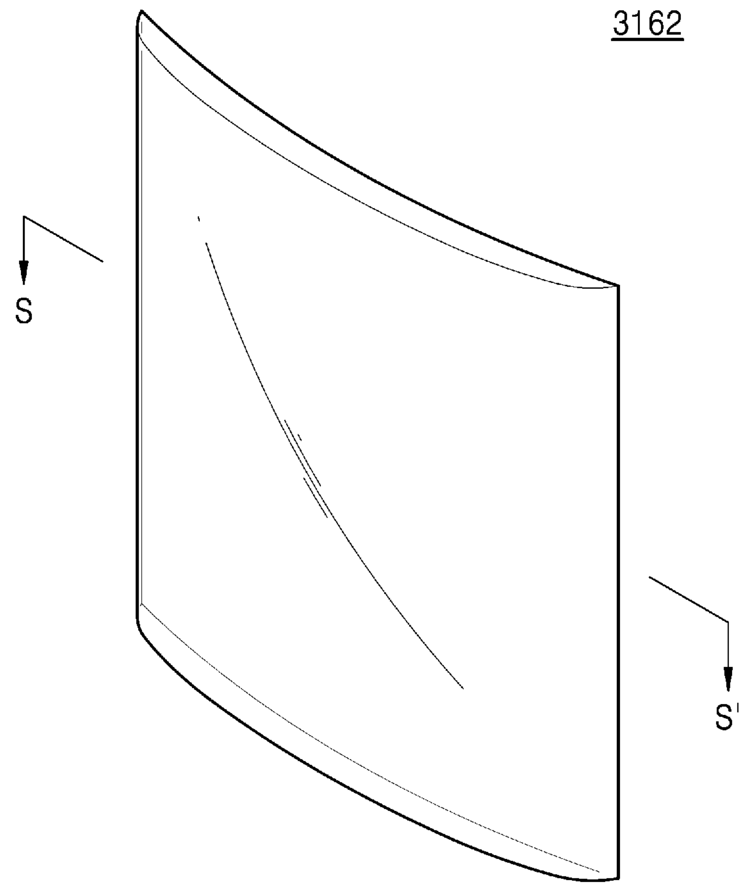
FIG. 19 is a schematic diagram of an outer cover plate of FIG. 17.
Figure 20:
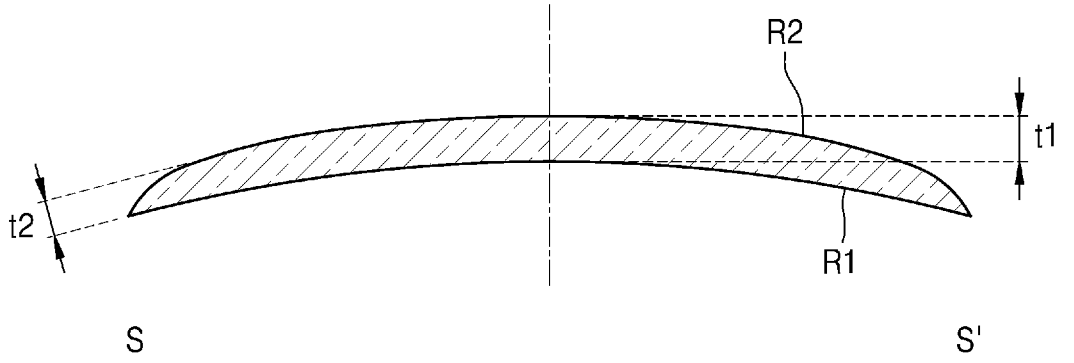
FIG. 20 is a cross-sectional view taken along a line S-S' of FIG. 19.

FIG. 19 is a view schematically illustrating the outer cover plate 3162 of FIG. 17, and FIG. 20 is a cross-sectional view taken along line S-S' of FIG. 19.

Referring to FIGS. 19 and 20, the outer cover plate 3162 may include an inner surface facing the user's face and an outer surface positioned opposite to the inner surface. For example, the outer cover plate 3162 may include the inner surface and the outer surface, and the inner surface and the outer surface may be curved surfaces having curvature. Accordingly, the outer cover plate 3162 may be formed to have the curved surface.

Meanwhile, a welding scene first passes through the outer cover plate 3162. That is, the welding scene passes through the outer cover plate 3162 and the light blocking cartridge 3163 and is captured by the camera. Therefore, as described above, the outer cover plate 3162 is formed of the material through which the light generated in the welding operation is transmitted. However, since the outer cover plate 3162 formed of this material has a different refractive index than that of air, the welding scene may be distorted while passing through the outer cover plate 3162. Therefore, in order to solve this problem, the outer cover plate 3162 may include a design structure to minimize distortion of the welding scene, as will be described later.

As an embodiment, a first radius of curvature R1 of the inner surface and a second radius of curvature R2 of the outer surface may be different from each other. For example, the first radius of curvature R1 of the inner surface may be smaller than the second radius of curvature R2 of the outer surface. Also, a center of first radius of curvature R1 of the inner surface and a center of second radius of curvature R2 of the outer surface may be different.

Therefore, the welding light or welding scene incident on the outer cover plate 3162 may be incident parallel to the camera, whereby the welding image generated by the processor and incident to the user's eye through the display unit 3120 may be an undistorted image. That is, the image projected on the user's eyes may be an image similar to that perceived with the naked eye, may be a high-quality image, and may not cause fatigue to the user's eyes despite long-time work.

As an embodiment, the outer cover plate 3162 may be formed in a shape having an overall curved surface, and specifically, may be formed in a curved surface shape having different thicknesses of a center portion and an outer portion.

For example, the outer cover plate 3162 may include the center portion and the outer portion spaced apart from the center portion and formed along the periphery of the outer cover plate 3162, a first thickness t1 of the center portion and a second thickness t2 of the outer portion may be different.

In a specific embodiment, the first thickness t1 of the center portion may be greater than the second thickness t2 of the outer portion. For example, the outer cover plate 3162 may be formed in a shape in which the center portion is relatively thick, and the thickness becomes thinner toward the outer portion.

Accordingly, for the outer cover plate 3162, the welding light or welding scene may be incident parallel to the camera as described above, and the welding image generated by the processor and incident to the user's eye through the display unit 3120 may be an undistorted image. That is, the image projected on the user's eyes may be an image similar to that perceived with the naked eye, may be a high-quality image, and may not cause fatigue to the user's eyes despite long-time work.

As an optional embodiment, the first thickness t1 of the center portion of the outer cover plate 3162 may be 1 mm<t1<2.6 mm, 1.5 mm<t1<2.6 mm, 2.0 mm<t1<2.6 mm, 2.1 mm≤t1≤2.5 mm, or 2.1 mm≤t1≤2.4 mm. In addition, the second thickness t2 of the outer portion of the outer cover plate 3162 may be at least 1.0 mm. For example, the second thickness t2 may be 1.0 mm≤t2≤1.5 mm. It is difficult to form the outer cover plate 3162 and the defect rate may increase when the first thickness t1 is out of the above-mentioned lower limit, and the weight of the outer cover plate 3162 increases when the first thickness is out of the above-mentioned upper limit, so it may be difficult to lightly implement the welding information providing apparatus 3100.

As another optional embodiment, the first radius of curvature R1 (unit: mm), the second radius of curvature R2 (unit: mm) and the second thickness t2 (unit: mm) may satisfy equation 1 below.

$$(R2-t2+t2/n)-1<R1<R2 \qquad \text{Equation 1}$$

Here, n represents the refractive index of the center portion of the outer cover plate 3162.

When the first radius of curvature R1, the second radius of curvature R2 and the second thickness t2 satisfy the above equation, a light passing through the center of the outer cover plate 3162 and a light passing through a part offset from the center are incident parallel to the outer cover plate 3162, so that the welding image may be more similar to the actual welding scene, and may be provided to the user in high quality.

Figure 21:
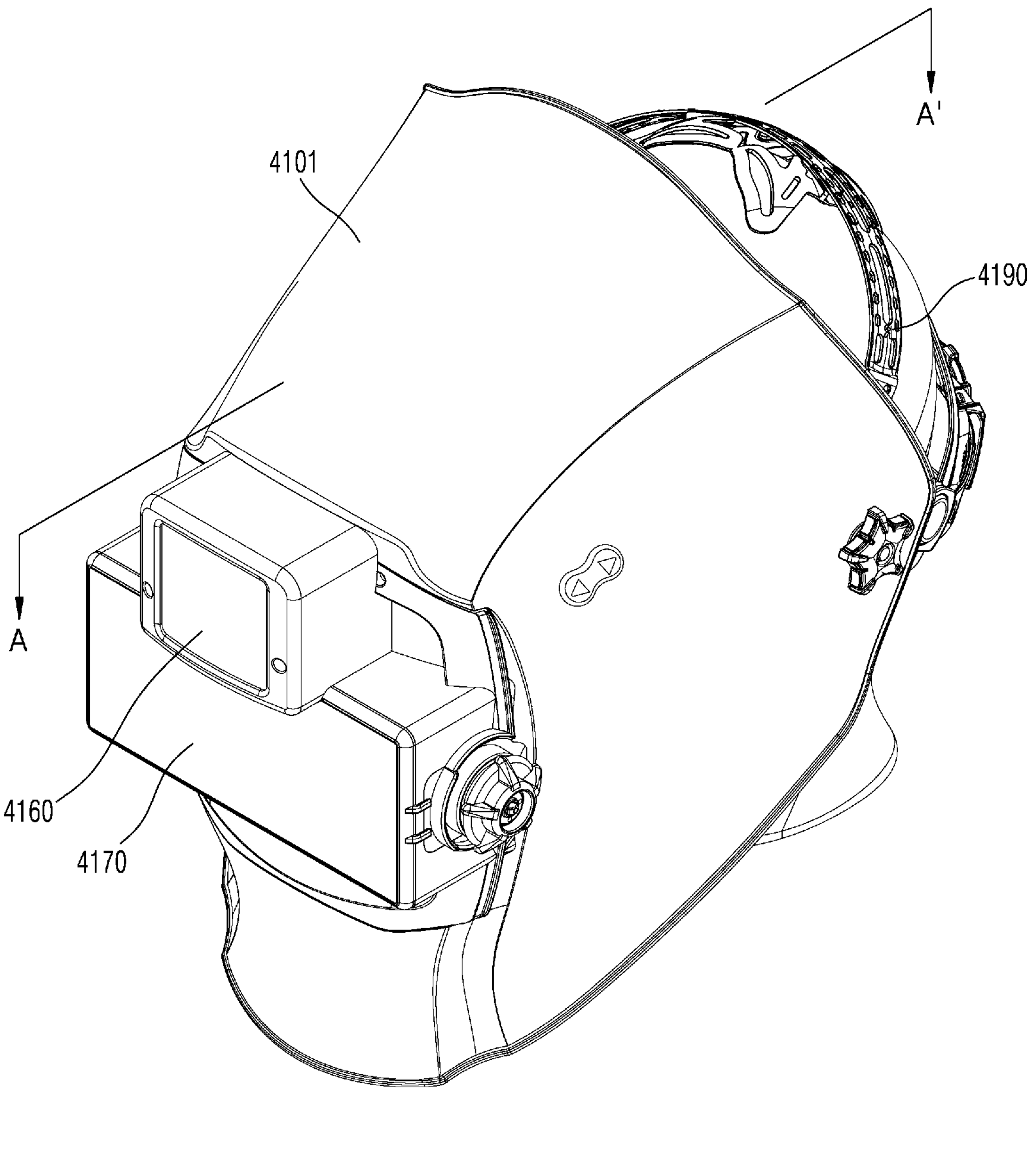
FIG. 21 is a perspective view of a welding information providing apparatus according to another embodiment of the present disclosure.
Figure 22:
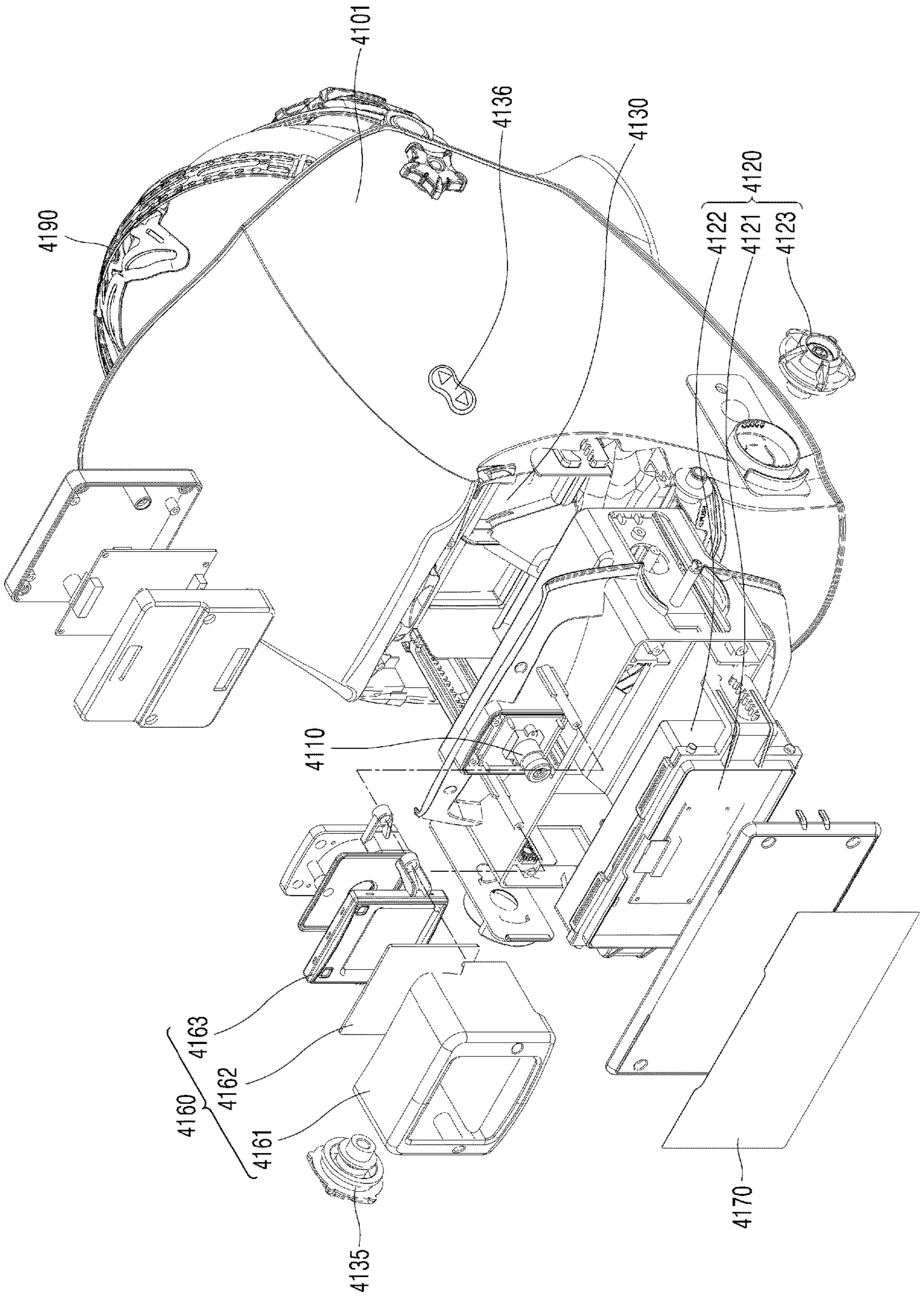
FIG. 22 is an exploded perspective view of FIG. 21.

FIG. 21 is a perspective view of a welding information providing apparatus according to another embodiment of the present disclosure, and FIG. 22 is an exploded perspective view of FIG. 21.

Referring to FIGS. 21 to 22, a welding system 410 may include a welding information providing apparatus 4100 and a welding torch 4200. The welding information providing apparatus 4100 may include a main body 4101, a camera unit 4110, a display unit 4120, a lens unit 4130, a processor 4140, a sensor unit 4150 and a communication unit 4190.

In addition, the welding information providing apparatus 4100 may include an outer cover unit 4160 protecting the camera unit 4110 and a fixing unit 4180 disposed on the rear surface of the main body 4101 to fix the welding information providing apparatus 4100 to the user's head.

Meanwhile, the main body 4101, the fixing unit 4180, the camera unit 4110, the display unit 4120, the processor 4140, the sensor unit 4150 and the communication unit 4190 of this embodiment may be the same as those included in the above-described embodiments or be similarly modified within a possible range. Accordingly, hereinafter, differences from the above-described embodiments will be mainly described.

The main body 4101 is for protecting the user's face and may be provided so as to be worn by the user.

The main body 4101 may be fixed to the user's head through the fixing unit 4180 provided inside the main body 4101.

The welding information providing apparatus 4100 may further include a light blocking plate 4170 disposed outside the main body 4101. For example, the light blocking plate 4170 may be provided on the outside of the main body 4101, and may be arranged to face a direction in which the welding takes place. The light blocking plate 4170 may be a means for reflecting a welding heat generated during a welding process. Therefore, the user may not be exposed to excessive heat during the welding process. In this case, the light blocking plate 4170 may be formed of a material capable of reflecting the welding heat, for example, a material containing aluminum.

The camera unit 4110 may include at least one camera mounted on the outside of the main body 4101 and obtaining a welding image frame for the welding operation.

The camera unit 4110 may be protected by the outer cover unit 4160. The outer cover unit 4160 may include an outer cover frame 4161, an outer cover plate 4162 and a light blocking cartridge 4163.

The outer cover frame 4161 may couple the outer cover unit 4160 to the main body 4101.

The outer cover plate 4162 may be placed in front of the light blocking cartridge 4163 to protect the light blocking cartridge 4163, and the light blocking cartridge 4163 may block the welding light generated during welding.

According to another embodiment of the present disclosure, the welding information providing apparatus 4100 may not include the light blocking cartridge 4163. In this case, the user may perform the welding operation only with the welding image acquired through the camera unit 4110.

The display unit 4120 may include a display panel 4121 displaying a high-definition composite image including the welding image or welding information obtained from the camera unit 4110, and a display frame 4122 disposed outside the display panel 4121 to fix the display panel 4121.

As an embodiment, a rack may be formed on the display frame 4122. In this case, the rack formed on the display frame 4122 may be a means for enabling the front and rear movement of the display panel 4121 as will be described later. That is, the welding information providing apparatus 4100 according to an embodiment of the present disclosure may include a display adjustment module, and a pinion is formed in the display adjustment module to be engaged with the rack formed in the display frame 4122. Therefore, the user may adjust the front and rear positions of the display panel 4121 by using the display adjustment module.

Figure 23:
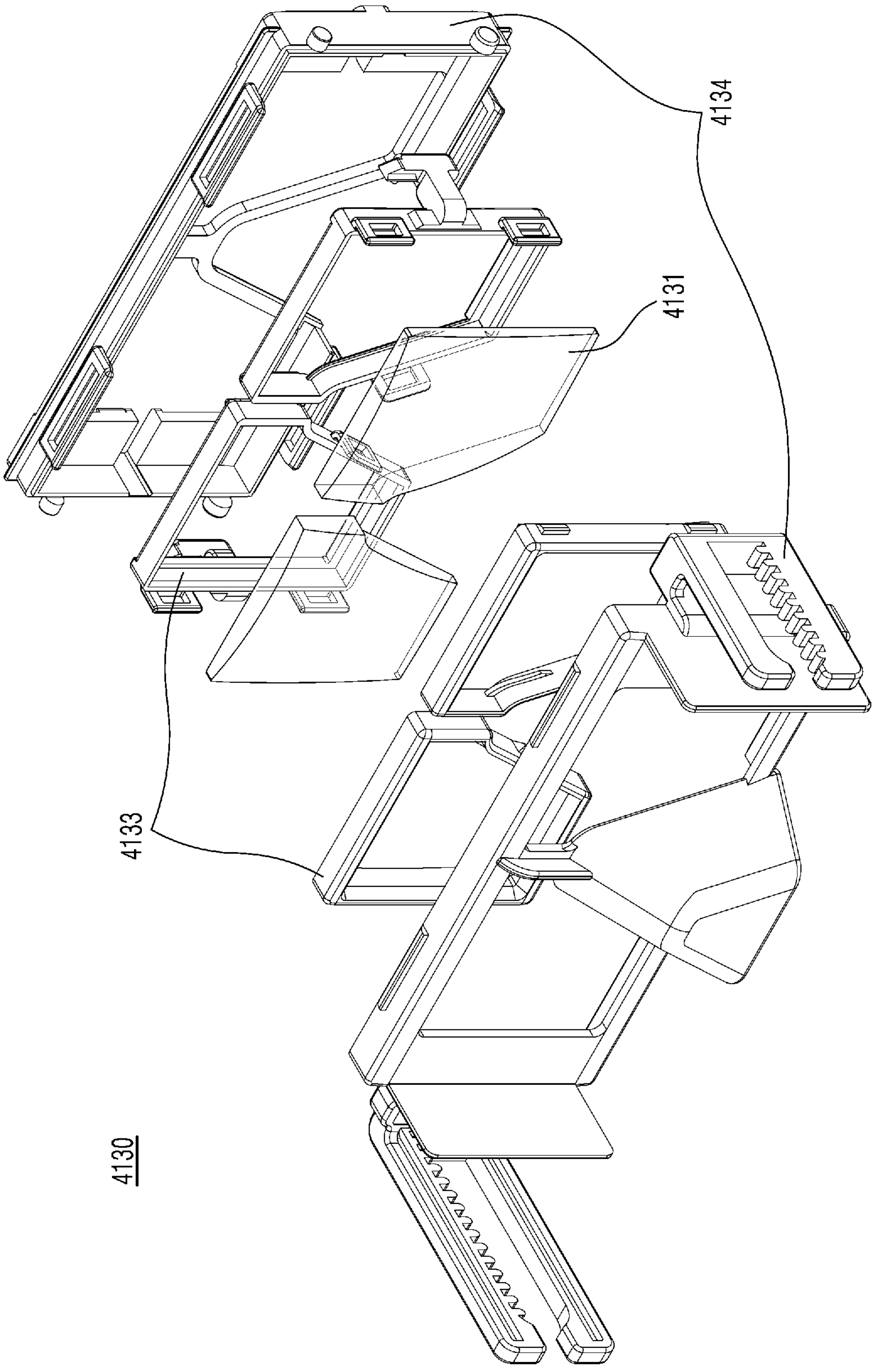
FIG. 23 is an exploded perspective view of a lens unit of FIG. 22.

FIG. 23 is an exploded perspective view of the lens unit of FIG. 22.

Referring to FIG. 23, the lens unit 4130 may be a means for guiding the image displayed from the display unit 4120 to the user's eyes. For example, the lens unit 4130 includes a pair of first lenses 4131 to correspond to the user's left and right eyes, and may guide the image displayed from the display unit 4120 to the user's eyes through the first lens 4131.

In one embodiment, the lens unit 4130 may include the first lens 4131, a first lens frame 4133 disposed to surround at least one area of the first lens 4131 to protect the first lens 4131, and a second lens frame 4134 disposed on the outside of the first lens frame 4133.

For example, the first lens frame 4133 may be formed to correspond to the outer shape of the first lens 4131 so that the first lens 4131 is interpolated. In an optional embodiment, the first lens frame 4133 may include a first-1 lens frame that surrounds the first lens 4131 so as to be in direct contact with the first lens 4131 and protects the first lens 4131, and a first-2 lens frame disposed outside the first-1 lens frame so that the first-1 lens frame is stably inserted and fixed. However, it is not limited thereto, and the first lens frame 4133 may consist of one configuration.

The first lens 4131 may be formed as a pair to correspond to the user's left and right eyes. Accordingly, as will be described later, the distance between the centers of the left and right lenses of the first lens 4131 may be adjusted to correspond to PD, which is the interval between the user's eyes.

As an embodiment, the first lens 4131 may be a convex lens. Accordingly, the user may enlarge the welding image displayed from the display unit 4120 and see it in detail. As an alternative embodiment, the first lens 4131 may be a Fresnel lens. Accordingly, since the thickness of the first lens 4131 may be reduced, the lens unit 4130 may be compactly configured, and furthermore, the welding information providing apparatus 4100 may be configured compactly.

The second lens frame 4134 may be configured to be disposed outside the first lens frame 4133. For example, the second lens frame may be configured to be coupled to the first lens frame 4133 so that the first lens frame 4133 is fixed.

In one embodiment, a rack may be formed on the second lens frame 4134. In this case, the rack formed on the second lens frame 4134 may be a means for enabling the front and rear movement of the lens unit 4130, as will be described later. That is, the welding information providing apparatus 4100 according to an embodiment of the present disclosure may include a lens position adjustment module, and a pinion is formed in the lens position adjustment module to be engaged with the rack formed in the second lens frame 4134. Accordingly, the user may adjust the front and rear positions of the lens unit 4130 by using the lens position adjustment module.

Figure 24:
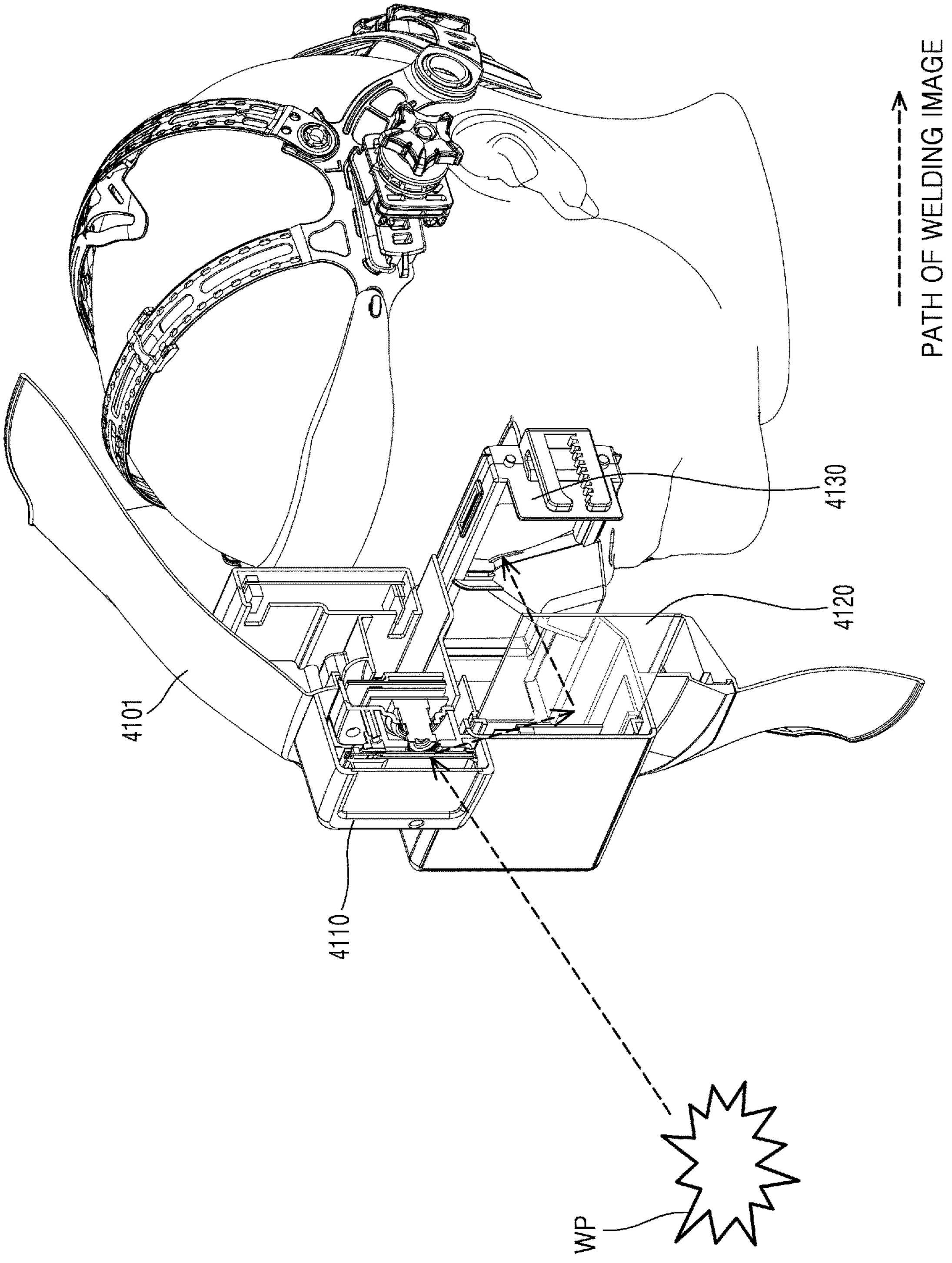
FIG. 24 is a diagram for describing a path of a welding image.

FIG. 24 is a diagram for explaining the path of the welding image.

Referring to FIG. 24, the welding image may be moved in the order of a welding occurrence point WP, the camera unit 4110, the display unit 4120, the lens unit 4130 and the user's eye. That is, the welding scene at the welding occurrence point WP may be acquired as the welding image frame through a camera 4111 included in the camera unit 4110. The welding image generated based on the welding image frame acquired through the camera 4111 may be displayed by the display unit 4120. In this case, the processor 4140 may control the display unit 4120 to display the welding image generated based on the welding image frame. The welding image displayed by the display unit 4120 may be viewed by the user's eyes through the lens unit 4130.

Meanwhile, the distance from the welding occurrence point to the user's field of view may be 500 to 700 mm.

When the distance from the welding occurrence point to the user's field of view is less than 500 mm, the welding information providing apparatus 4100 may not be formed to include the camera unit 4110, the display unit 4120 and the lens unit 4130. That is, in order for the welding information providing apparatus 4100 to be formed to include the above-described configuration, the distance from the welding occurrence point WP to the user's field of view needs to be secured at least 500 mm.

In addition, if the distance from the welding occurrence point WP to the user's field of view exceeds 700 mm, a sense of incongruity between the user's working environment and the welding image reflected on the user's eyes may occur. That is, if the distance from the welding occurrence point WP to the user's field of view exceeds 700 mm, the user may not be able to efficiently and precisely perform the welding operation because the actual welding operation and the welding image reflected on the eyes are different.

Figure 25:
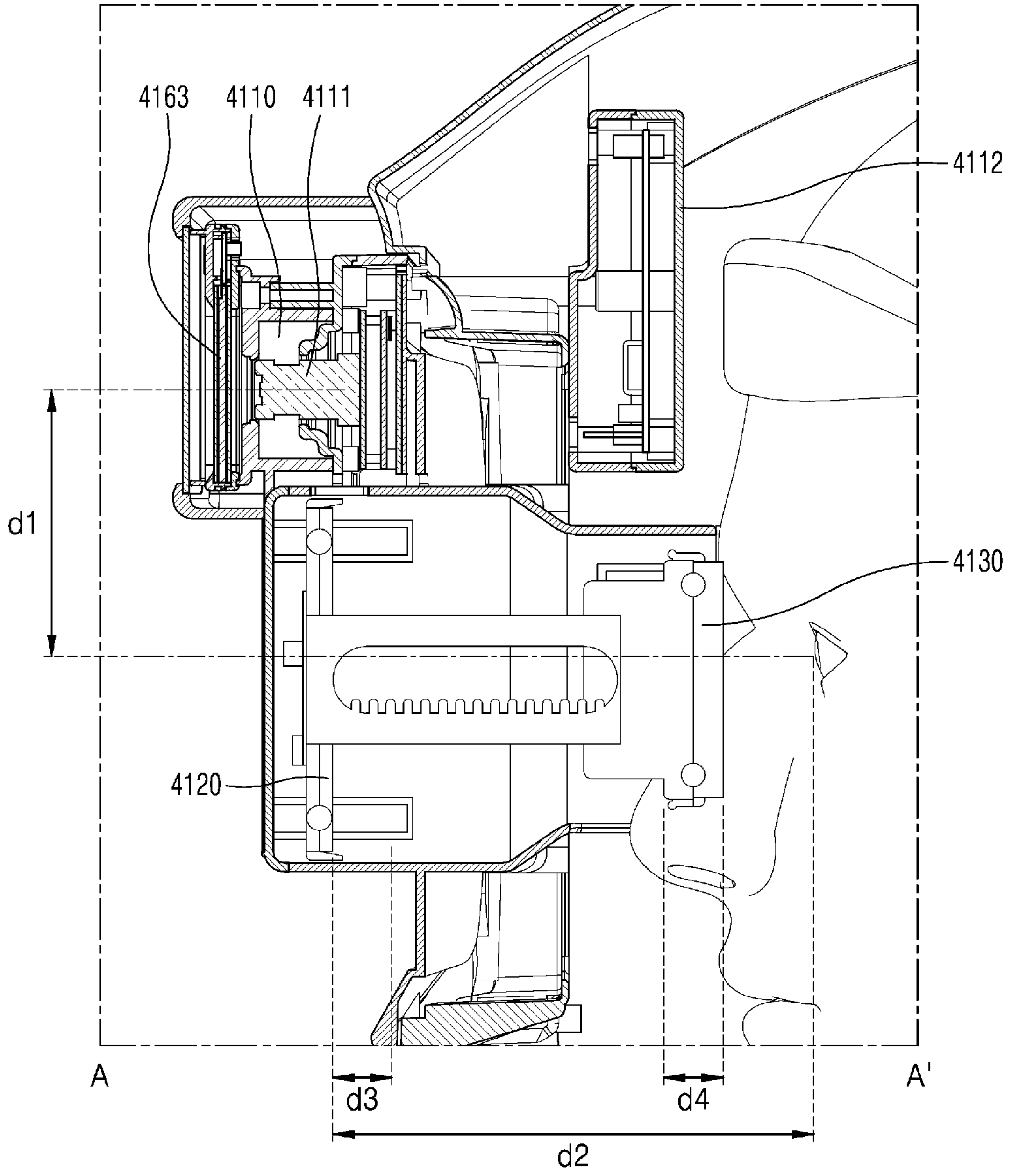
FIG. 25 is a cross-sectional view taken along a line A-A' of FIG. 21.

FIG. 25 is a cross-sectional view taken along line A-A' of FIG. 21.

Referring to FIG. 25, the camera unit 4110 may include the camera 4111. The camera 4111 may be a means of capturing the welding scene to obtain the welding image frame for the welding operation. The welding information providing apparatus 4100 may synthesize the welding image frame obtained through the camera 4111 into the welding image and display it to the user.

The camera 4111 may include a lens of the camera 4111 through which an optical image generated at the welding occurrence point WP passes. In this case, a vertical distance d1 from the center of the lens of the camera 4111 to the center of the user's field of view may be 50 mm or less.

The user may proceed with the welding operation while wearing the welding information providing apparatus 4100, and the user may not feel the sense of incongruity when performing the welding operation while looking at a welding point, so that the welding operation may be performed accurately and easily. Therefore, it is preferable that the direction that the lens of the camera 4111 faces and the direction of the user's field of view are not spaced apart more than a certain distance. That is, if the vertical distance d1 from the center of the lens of the camera 4111 to the center of the user's field of view exceeds 50 mm, the difference between a position expected to be projected on the user's field of view and a position where the camera 4111 actually captures the image increases, and a visual sense of incongruity may occur.

As an embodiment, the camera unit 4110 may include a camera adjustment module 4112 for adjusting the position of the camera 4111. The camera adjustment module 4112 may be a means for adjusting the vertical position of the camera 4111. Therefore, the user may adjust the position of the camera 4111 during the welding operation to proceed with the welding operation without feeling the sense of incongruity.

During the welding operation, a viewing distance d2, which is a distance from the user's field of view to the display unit 4120, may be formed in a range of 60 to 100 mm. For example, the viewing distance d2 may be a distance from the user's field of view to the surface of the display panel 4121 included in the display unit 4120. In this case, the display panel 4121 may be a screen on which the welding image is displayed. If the viewing distance d2 is less than 60 mm, a sufficient distance for the welding image displayed on the display unit 4120 to be transmitted to the user's field of view may not be secured, so that the welding image may be distorted or not clearly transmitted. In addition, when the viewing distance d2 is more than 100 mm, the user may feel the sense of incongruity because the welding point and the user's field of view are too far away.

As an embodiment, the display unit 4120 may be moved in a front-rear direction. To this end, the welding information providing apparatus 4100 may include the display adjustment module for moving the display panel 4121 back and forth.

For example, the display adjustment module may move the display panel 4121 back and forth so that the user may perform the welding operation in a state where an optimal welding screen is provided.

As an optional embodiment, the display adjustment module may move the display panel 4121 within a predetermined display movement section d3. For example, the display movement section d3 may be less than 20 mm. If the display movement section d3 exceeds 20 mm, the distance from the display panel 4121 to the user's field of view is too close, and a distorted or unclear welding image may be transmitted to the user's field of view.

In this case, the display movement section d3 may be included in the viewing distance d2. That is, the viewing distance d2 may be a distance including the display movement section d3 and a lens movement section d4 to be described later.

Meanwhile, the welding information providing apparatus 4100 may further include a display adjustment apparatus 4123 for controlling the display adjustment module. For example, the display adjustment apparatus 4123 may be a means for controlling the front and rear movement distance d3 of the display panel 4121 by controlling the display adjustment module. The display adjustment apparatus 4123 may be configured as a button or a rotary switch. However, the present invention is not limited thereto.

The lens unit 4130 may include the pair of first lenses 4131 to correspond to the user's left and right eyes. The first lens 4131 may be a means for guiding the image displayed from the display unit 4120 to the user's eyes.

As an embodiment, the lens unit 4130 may be moved in the front-rear direction. For example, for this purpose, the welding information providing apparatus 4100 may include the lens position adjustment module for moving the lens unit 4130 back and forth.

For example, the lens position adjustment module may move the lens unit 4130 back and forth so that the optimal welding screen is illuminated in the user's field of view. That is, a size or resolution of the welding screen that feels optimal for each user may be different, and each user's eyesight may be different. Accordingly, the lens position adjustment module may provide a welding screen optimized for each user by moving the position of the lens unit 4130 back and forth.

As an alternative embodiment, the lens position adjustment module may move the lens unit 4130 within a predetermined lens movement section d4. For example, the lens movement section d4 may be less than or equal to 20 mm. If the lens movement section d4 exceeds 20 mm, the distance from the lens unit 4130 to the user's field of view is too far, and a distorted or unclear welding image may be transmitted to the user's field of view.

In this case, the lens movement section d4 may be included in the viewing distance d2. That is, the viewing distance d2 may be the distance including the display movement section d3 and the lens movement section d4.

Meanwhile, the welding information providing apparatus 4100 may further include a lens position adjustment apparatus 4135 for controlling the lens position adjustment module. For example, the lens position adjustment apparatus 4135 may be a means for adjusting the front and rear movement distance d4 of the lens unit 4130 by controlling the lens position adjustment module. The lens position adjustment apparatus 4135 may be configured as a button or as a rotary switch. However, the present invention is not limited thereto.

Figure 26:
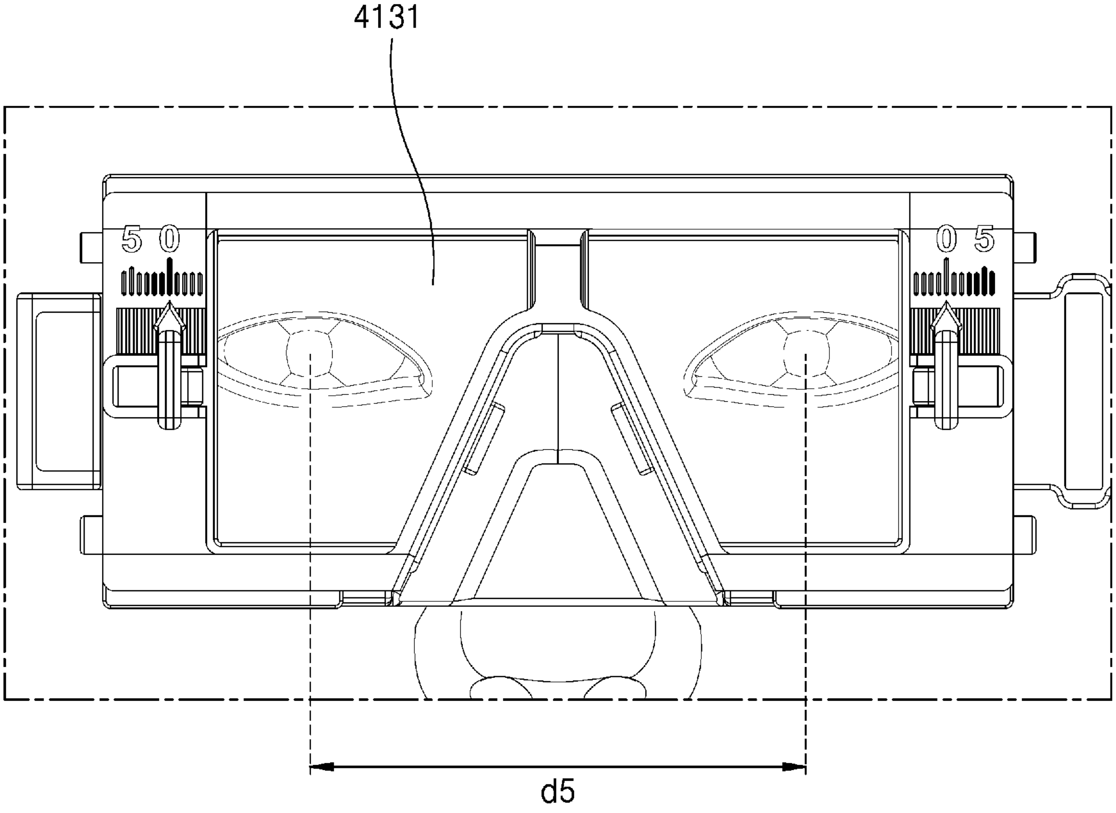
FIG. 26 is a diagram for describing left and right movement of a lens.

FIG. 26 is a view for explaining the left and right movement of the lens.

Referring to FIG. 26, a distance d5 between the pair of first lenses 4131 disposed to correspond to both eyes of the user may be adjusted.

The first lens 4131 may be the convex lens or the Fresnel lens as described above, since the outer surface of this lens is formed to be curved, the clearest and sharpest image may be obtained only when the center of the lens is placed at the center of the user's pupil. However, since the distance PD between the eyes is different for each person, the distance d5 between the first lenses 4131 needs to be adjusted accordingly.

To this end, the welding information providing apparatus 4100 may include a lens PD adjustment module for adjusting the distance d5 between the centers of the first lenses 4131. For example, the lens PD adjustment module may be a means for adjusting the PD d5 of the pair of first lenses 4131.

Accordingly, the user may automatically or manually adjust the distance d5 between the centers of the first lenses 4131 to correspond to the distance between his or her eyes.

In an optional embodiment, the welding information providing apparatus 4100 may further include a lens PD adjustment apparatus 4136 for controlling the lens PD adjustment module. For example, the lens PD adjustment apparatus may be a means for controlling the lens PD adjustment module to adjust the distance d5 between the first lenses 4131. The lens PD adjustment apparatus 4136 may be configured as a button or as a rotary switch.

In this case, the distance d5 between the first lenses 4131 may be 60 to 70 mm. That is, the distance d5 between the first lenses 4131 may be adjusted to correspond to the distance between the pupils of a person, so that it may not be necessary to provide an unnecessary space for the welding information providing apparatus 4100.

On the other hand, when the first lens 4131 is disposed at a distance of 20 mm or less from the user's eye, the lens is too close to the eye, which may provide an unclear image to the user or form an inverted image. Accordingly, the lens unit 4130 may be disposed to be spaced apart from the user's eyes by 20 mm or more. For example, the first lens 4131 may be disposed to be spaced apart from the user's eyes by 20 mm or more.

Figure 27:
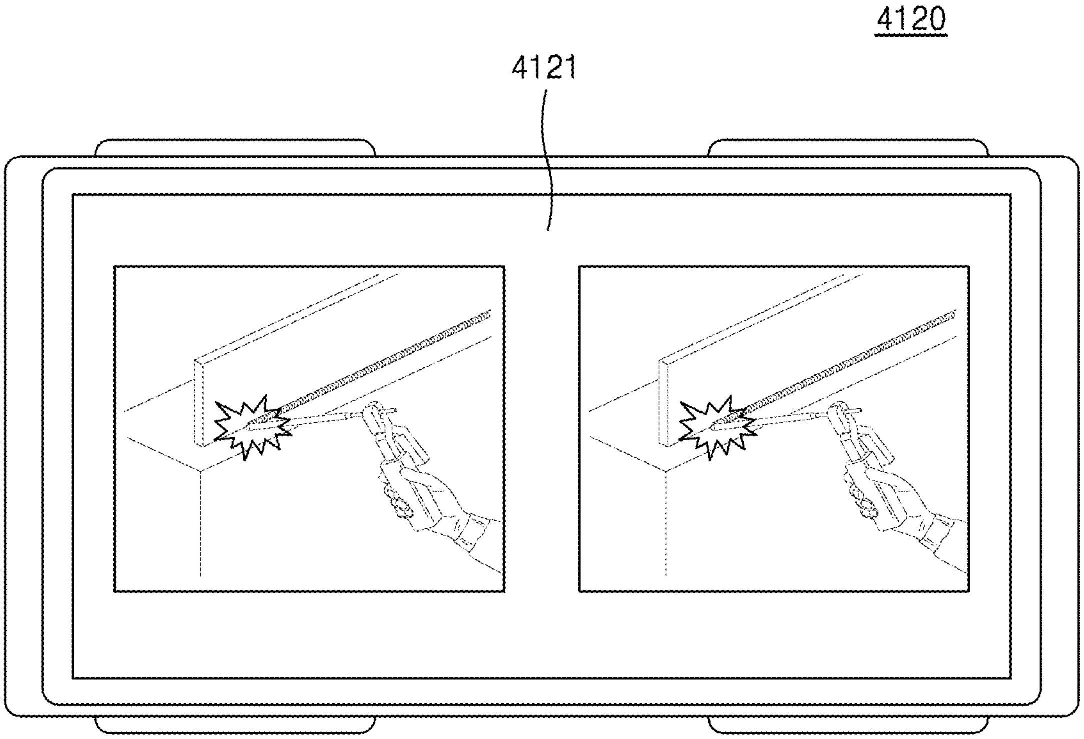
FIG. 27 is a diagram for describing a screen division of a display.
Figure 28A:
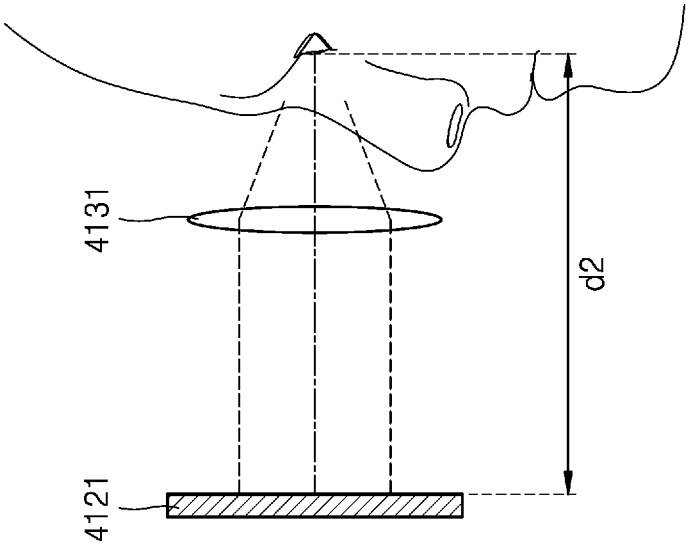
FIG. 28A is a diagram for describing a moving path of a welding image when a first lens is only included.
Figure 28B:
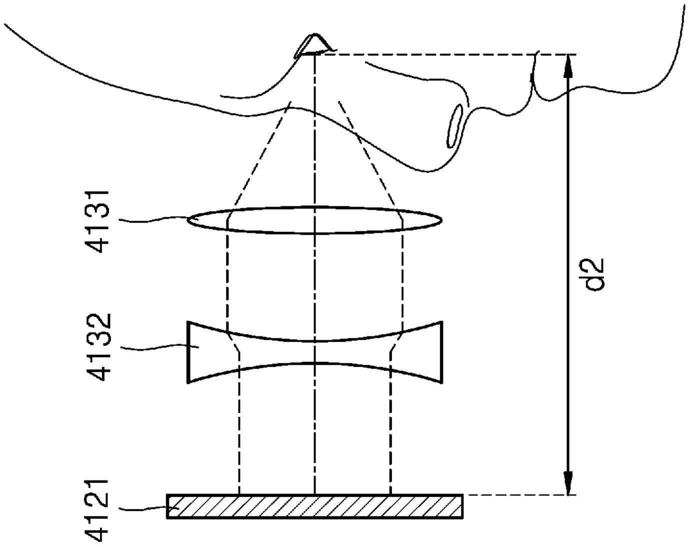
FIG. 28B is a diagram for describing a moving path of a welding image when a first lens and a second lens are included.

FIG. 27 is a view for explaining screen division of a display, FIG. 28 (*a*) is a view for explaining the movement path of the welding image when only the first lens 4131 is included, and FIG. 28 (*b*) is a view for explaining the movement path of the welding image when the first lens 4131 and a second lens 4132 is included.

Referring to FIGS. 27 and 28 (*a*) and (*b*), the display unit 4120 may selectively display the welding operation image on one screen or two screens divided to correspond to the user's eyes.

For example, when the viewing distance d2 is greater than a predetermined value, the path through which the image displayed on the display panel 4121 enters the user's field of view is sufficiently secured, so that a clear welding image may be obtained only through the first lens 4131. On the other hand, if the viewing distance d2 is smaller than the predetermined value, the path through which the image displayed on the display panel 4121 enters the user's field of view is not sufficiently secured, so that a clear welding image may not be obtained with only the first lens 4131.

To solve this, when the viewing distance d2 is 60 to 80 mm, a pair of second lenses 4132 may be disposed between the first lens 4131 and the display panel 4121 to correspond to the first lens 4131.

As an embodiment, in the welding information providing apparatus 4100, when the viewing distance d2 is 60 to 80 mm, the pair of second lenses 4132 may be inserted between the first lens 4131 and the display panel 4121 to correspond to the first lens 4131. To this end, the welding information providing apparatus 4100 may include a second lens moving module for moving the second lens 4132.

As an optional embodiment, when recognizing that the viewing distance d2 is 60 to 80 mm, the processor 4140 may control the second lens moving module to insert the second lens 4132 between the first lens 4131 and the display panel 4121. In addition, when recognizing that the viewing distance d2 is 80 to 100 mm, the processor 4140 may control the second lens 4132 moving module to move the second lens 4132 away from between the first lens 4131 and the display panel 4121.

For example, when the user moves the display panel 4121 back and forth, the display movement section d3 may change, and when the user moves the lens unit 4130 back and forth, the lens movement section d4 may change. In this case, since the viewing distance d2 changes when the display movement section d3 and the lens movement section d4 change, the processor 4140 calculates the movement amount of the display panel 4121 and the movement amount of the lens unit 4130, and may control the second lens moving module to insert the second lens 4132 between the first lens 4131 and the display panel 4121 when the viewing distance d2 is 60 to 80 mm.

In one embodiment, the second lens 4132 may be a concave lens. That is, when the viewing distance d2 is 60 to 80 mm, the concave lens refracts the optical image displayed on the display panel 4121 to offset an insufficiently secured optical path. That is, the concave lens refracts the light emitted from the display panel 4121 and makes it incident on the first lens 4131, so that the user may obtain a clear and sharp image.

As an embodiment, when the second lens 4132 is inserted, that is, when the viewing distance d2 is 60 to 80 mm, the display unit 4120 may display the welding operation image by dividing it into two screens to correspond to the user's eyes. For example, the display unit may display two welding operation images to correspond to the left and right eyes of the user, and may illuminate the divided images respectively on the left and right eyes of the user.

This may be to prevent image distortion when one image is projected too close to both eyes of the user. Therefore, when the viewing distance d2 is 60 to 80 mm, the display unit 4120 provides the divided images to both eyes of the user and controls the distance of the divided images, so that the user may recognize it as one undistorted image.

Meanwhile, when the second lens 4132 is inserted, the second lens 4132 may be disposed to correspond to the first lens 4131. For example, the second lens 4132 may be arranged to be coupled to the first lens 4131. Accordingly, when the distance d5 between the first lenses 4131 changes, the second lens 4132 may move to correspond to it.

Also, if the first lens 4131 moves within the lens movement section d4, the second lens 4132 may also move.

The distance between the centers of the two screens displayed on the display unit 4120 may be adjusted manually or automatically.

For example, the welding information providing apparatus 4100 may include an image PD adjustment module for adjusting the distance between the centers of two divided screens when the divided screens are displayed on the display unit 4120.

As another example, the processor 4140 may adjust the distance between the centers of the two screens displayed on the display unit 4120 based on the distance d5 between the centers of the first lenses 4131. That is, the processor 4140 may adjust the distance between the centers of the two screens to provide a clear image to the user's field of view based on the distance d5 between the centers of the first lenses 4131. That is, when the distance d5 between the lenses is changed, the distance between the centers of the divided screens is directly reflected, and the relative positions of the divided screens may be changed at the same time.

Figure 29:
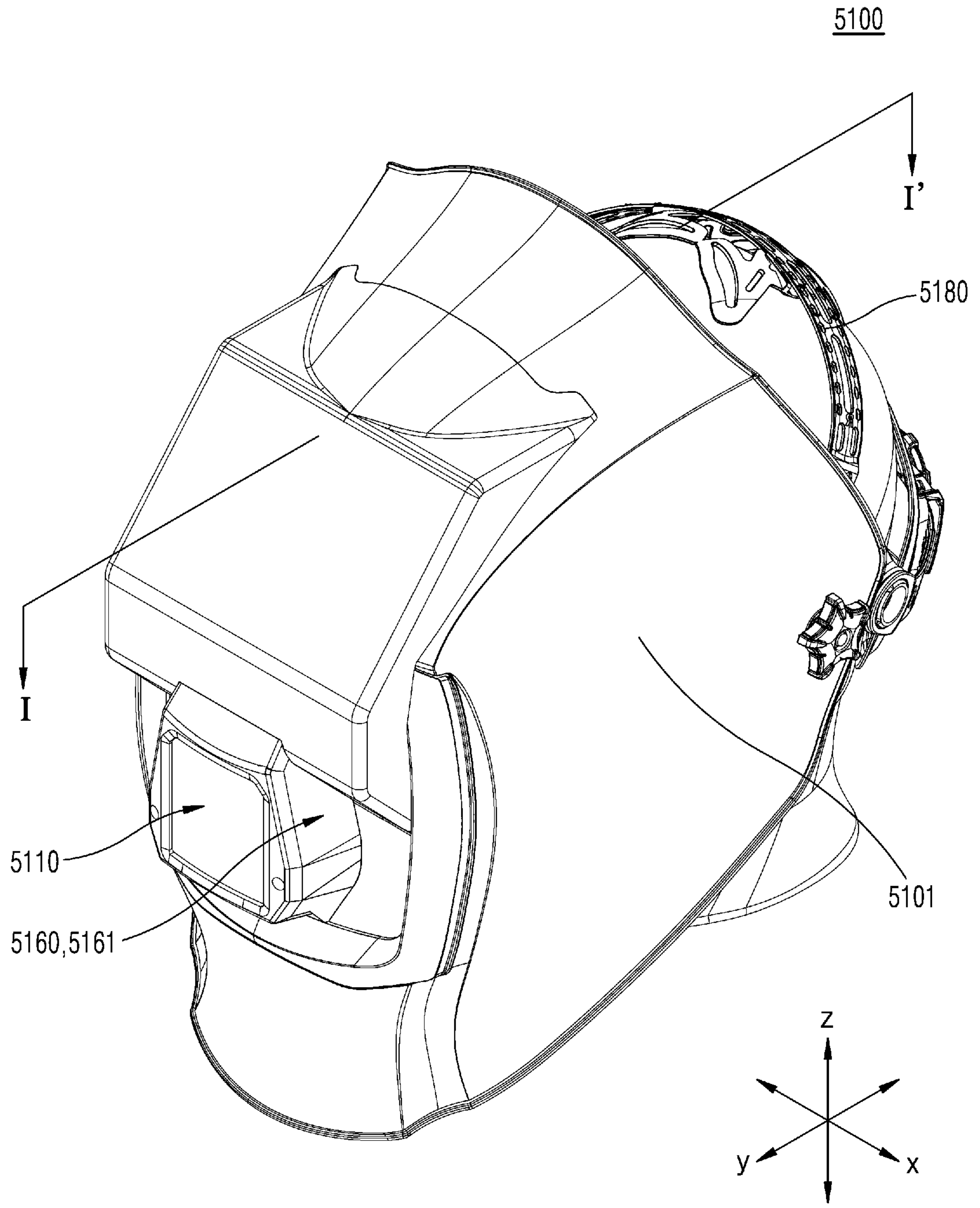
FIG. 29 is a perspective view of a welding information providing apparatus according to an embodiment of the present disclosure.
Figure 30:
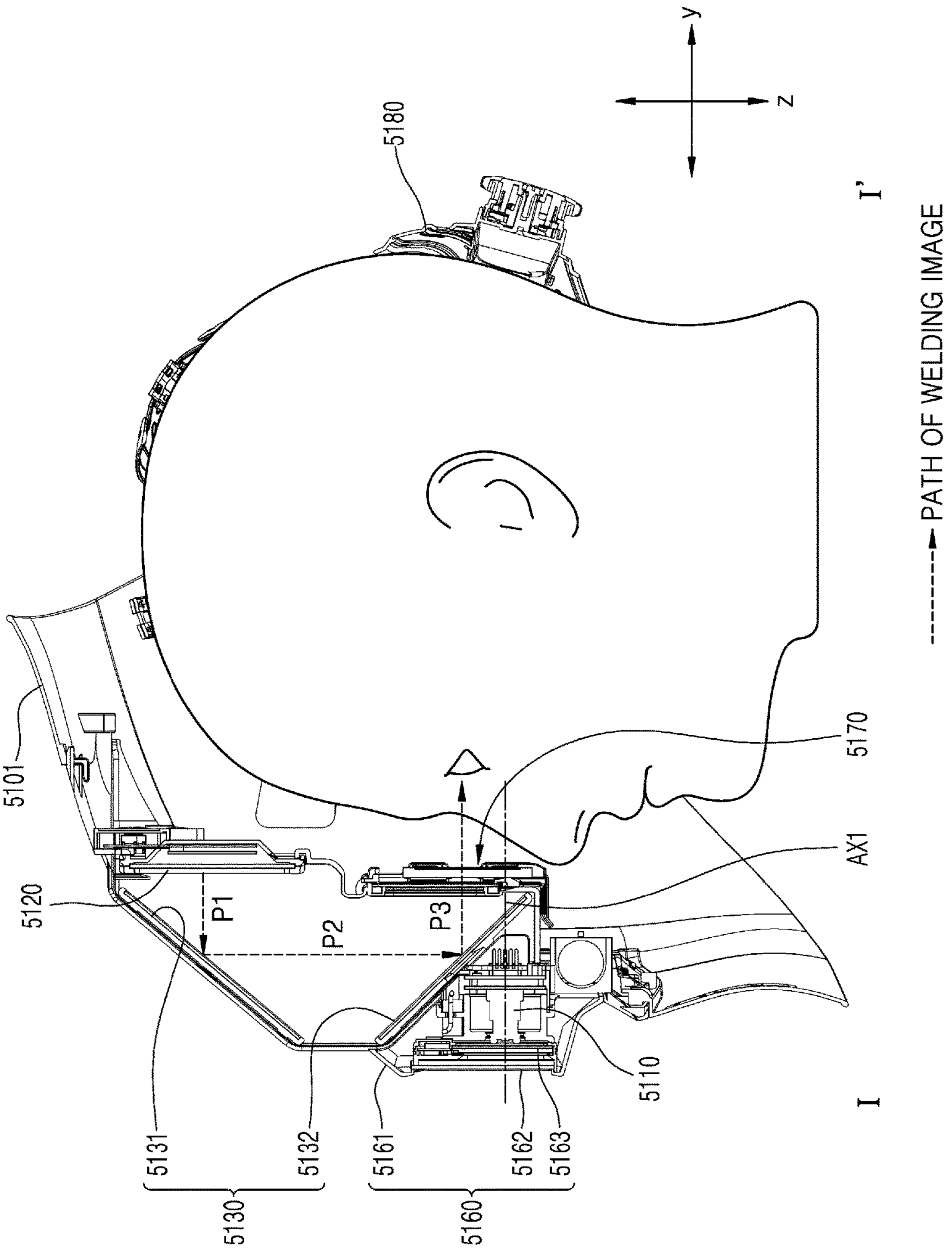
FIG. 30 is a cross-sectional view taken along a line I-I' of FIG. 29.
Figure 31:
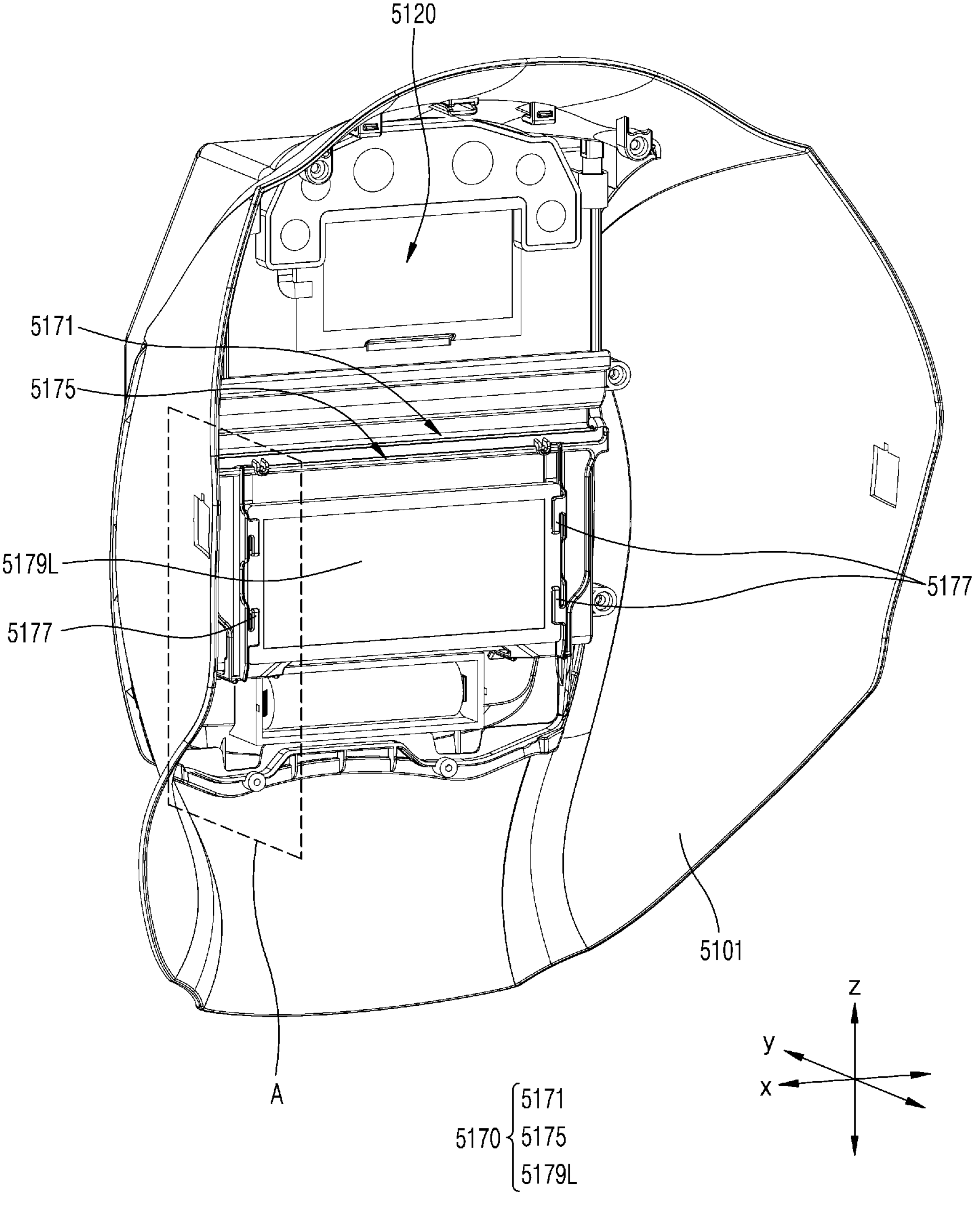
FIG. 31 is a perspective view showing a rear surface of a main body according to an embodiment of the present disclosure.
Figure 32:
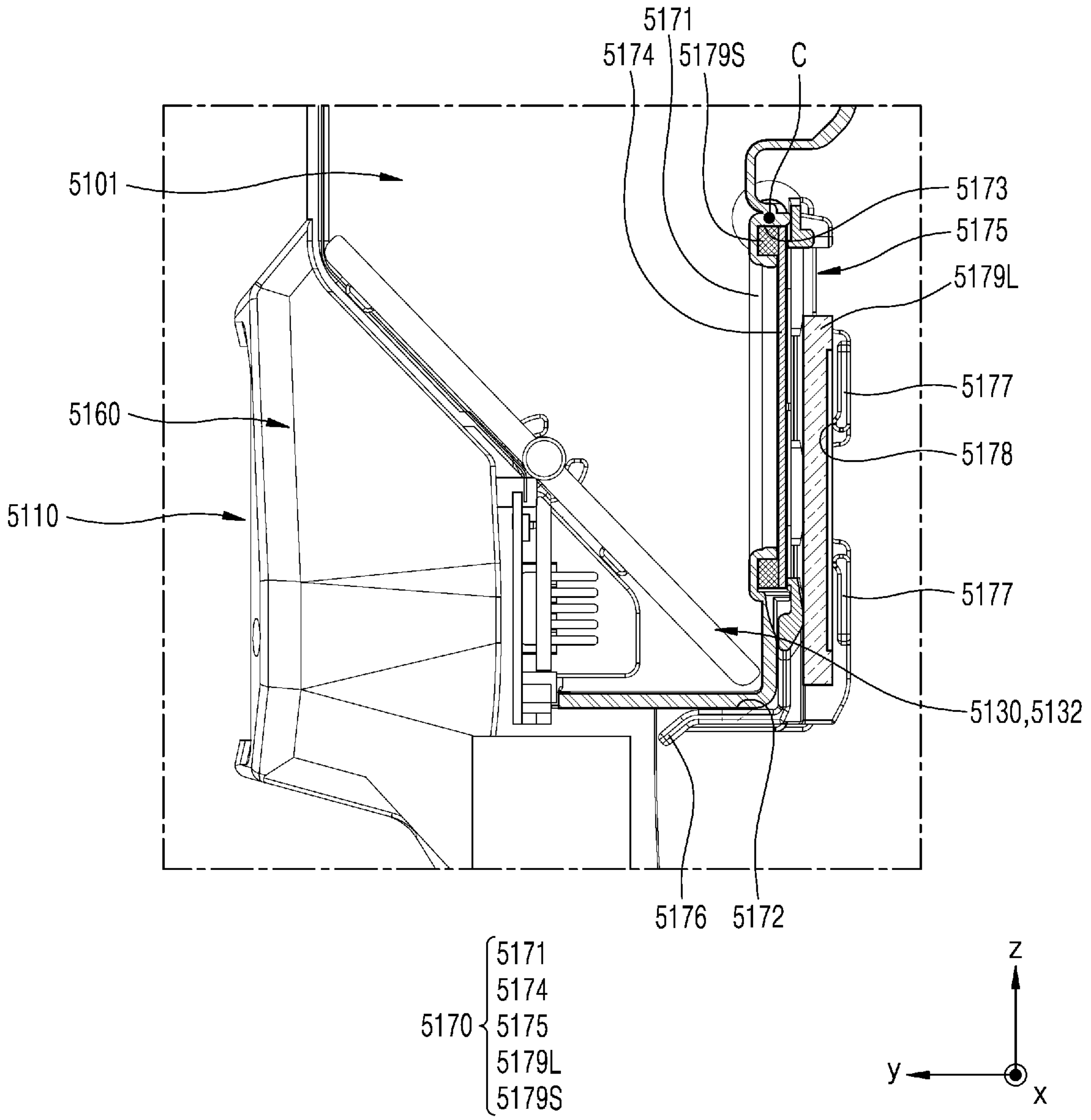
FIG. 32 is a cross-sectional view of part A of FIG. 31 in a yz plane.
Figure 33:
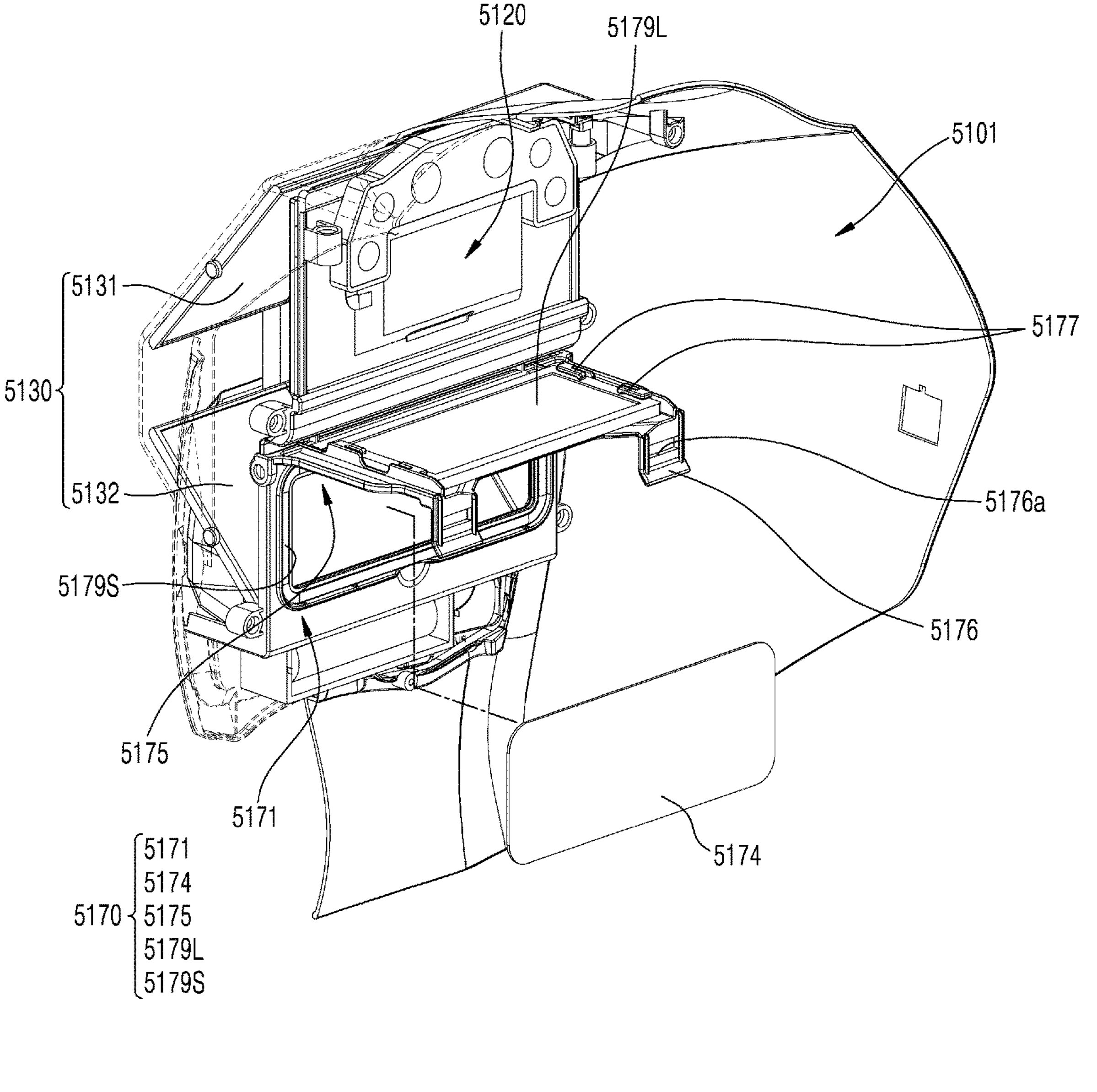
FIG. 33 is a diagram showing a state in which a cover holder unit according to an embodiment of the present disclosure is opened.
Figure 34:
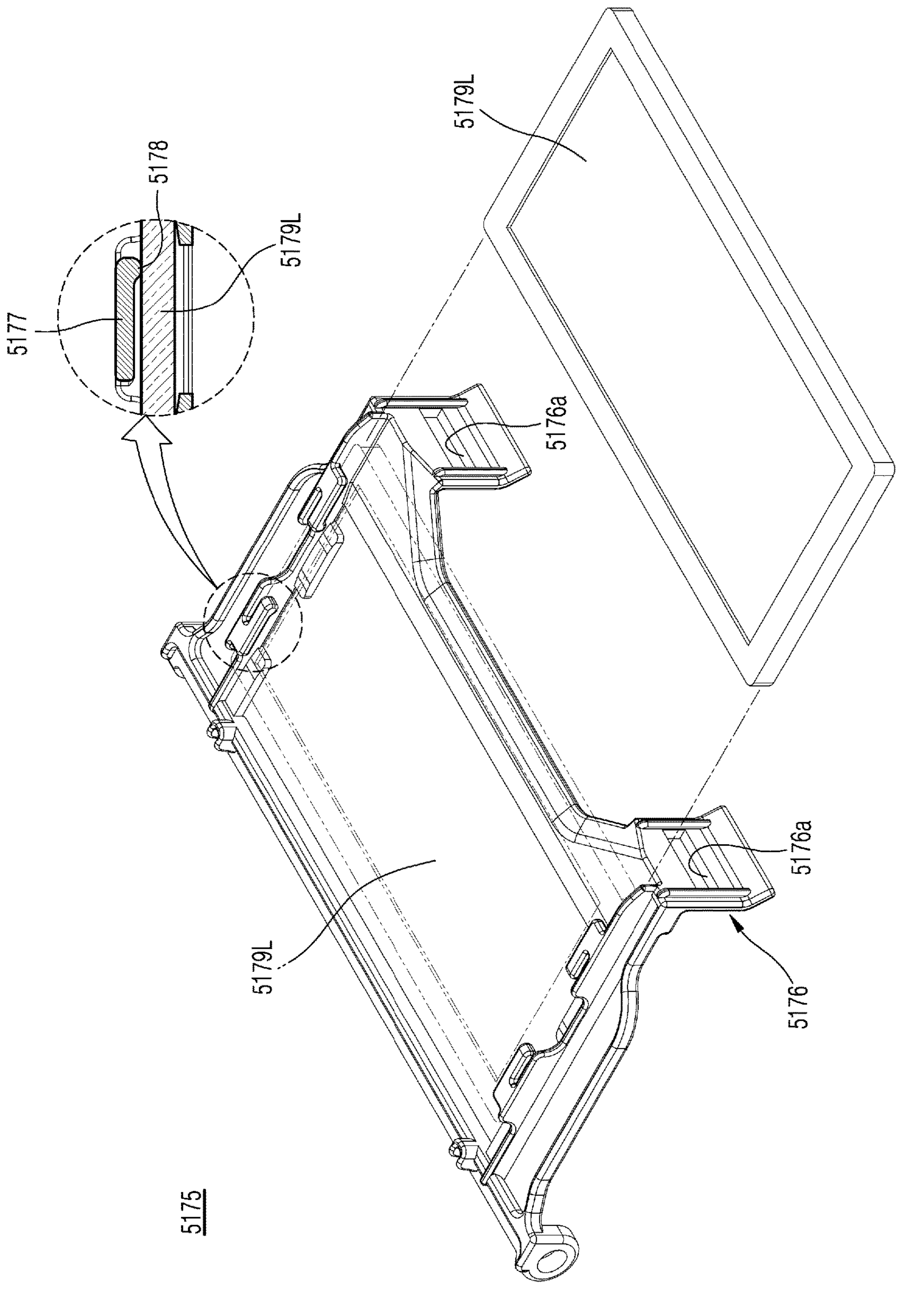
FIG. 34 is a perspective view of a cover holder unit and a lens unit according to an embodiment of the present disclosure.
Figure 35:
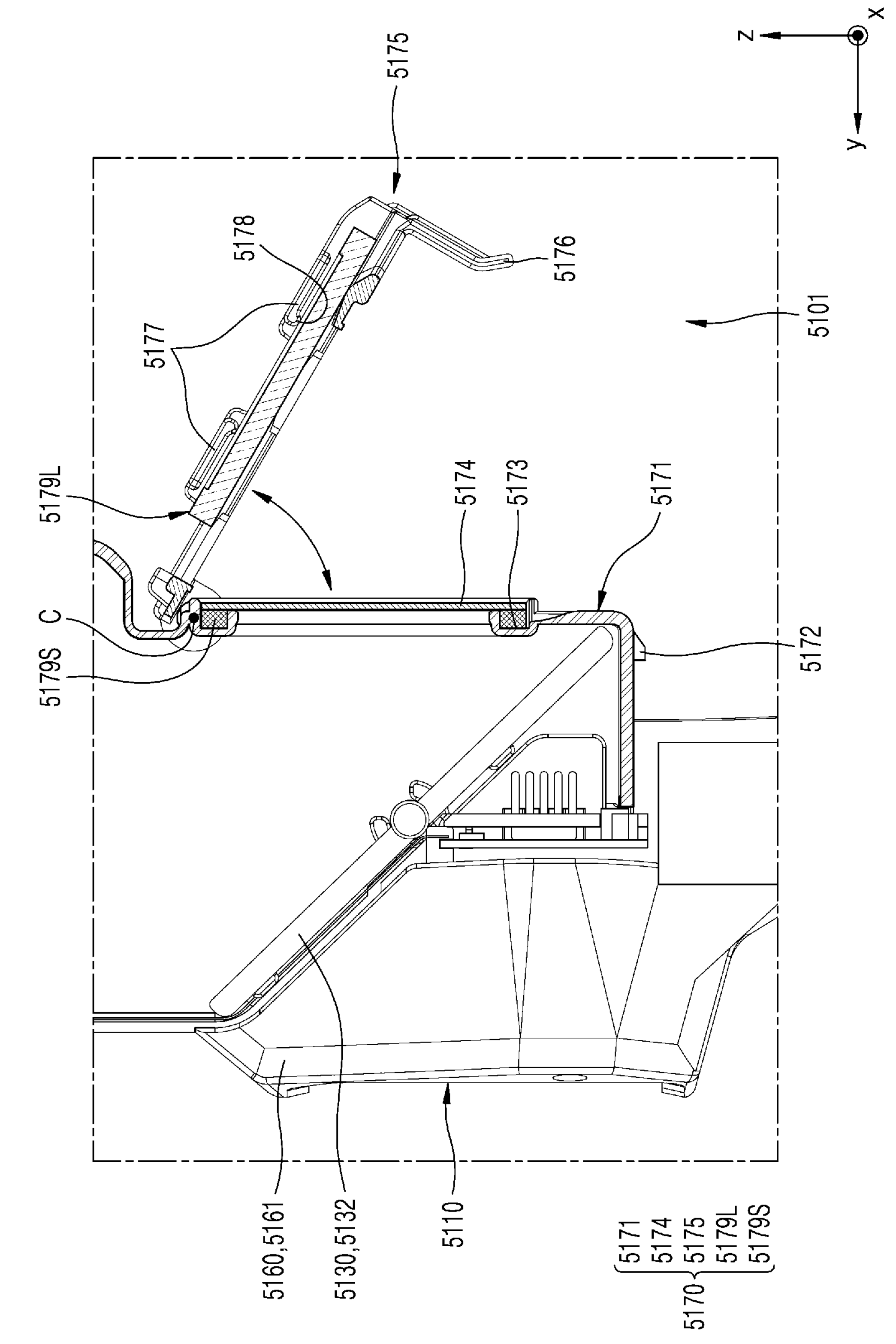
FIG. 35 is a diagram showing a state when the cover holder unit of FIG. 32 is opened.
Figure 36:
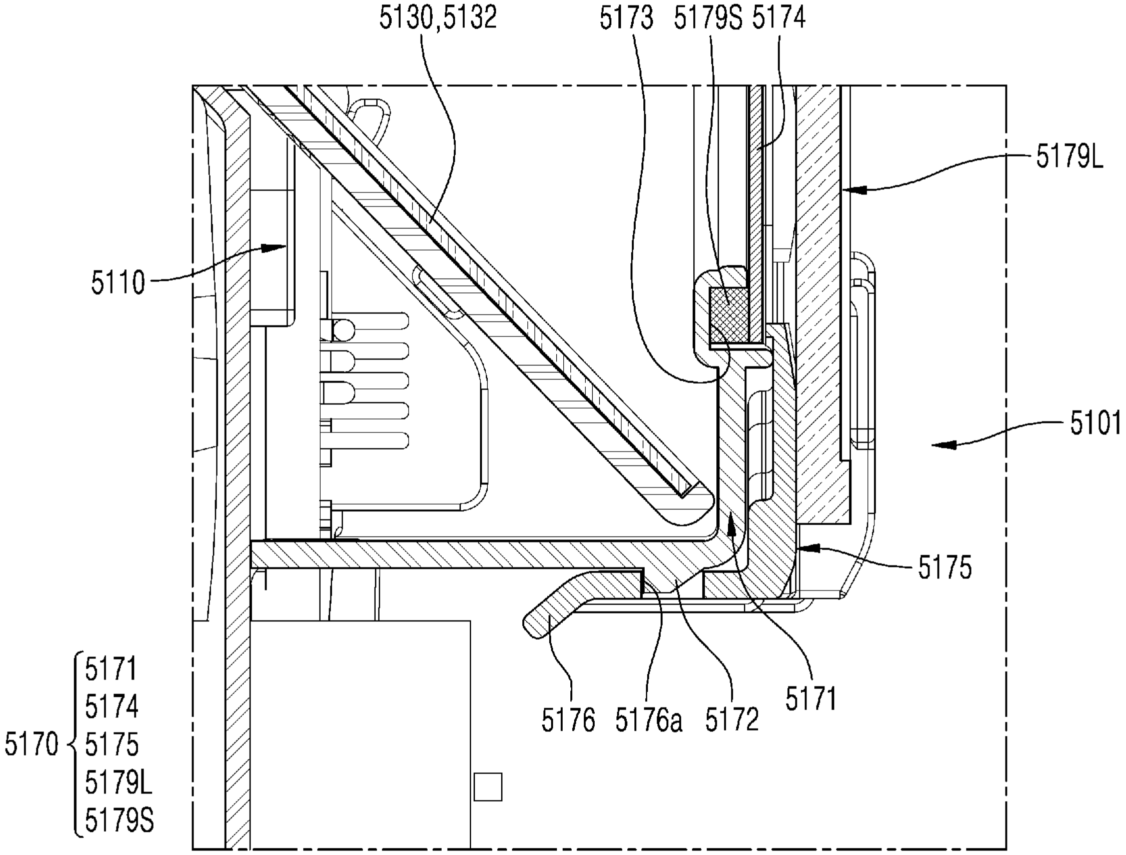
FIG. 36 is a cross-sectional view of part B of FIG. 31 in a yz plane.

FIG. 29 is a perspective view of a welding information providing apparatus according to another embodiment of the present disclosure. FIG. 30 is a cross-sectional view taken along line I-I' of FIG. 29. FIG. 31 is a perspective view illustrating a rear surface of a main body according to an embodiment of the present disclosure. FIG. 32 is a cross-sectional view of part A of FIG. 31 in the yz plane. FIG. 33 is a view illustrating an open state of a cover holder unit according to an embodiment of the present disclosure. FIG. 34 is a perspective view illustrating the cover holder unit and a lens unit according to an embodiment of the present disclosure. FIG. 35 is a view illustrating an open state of the cover holder unit in FIG. 32. FIG. 36 is a cross-sectional view of part B of FIG. 31 in the yz plane.

A welding information providing apparatus 5100 according to an embodiment of the present disclosure may include a main body 5101, a camera unit 5110, a display unit 5120, a path change unit 5130, a processor 5140, a sensor unit 5150, an outer cover unit 5160, an inner cover unit 5170, a fixing unit 5180 and a communication unit. For example, in the main body 5101 according to an embodiment of the present disclosure, to be described later, the camera unit 5110, the display unit 5120, the path change unit 5130, the processor 5140, the sensor unit 5150, the outer cover unit 5160, the inner cover unit 5170, the fixing unit 5180 and the communication unit 5190 may be disposed, and the user may be protected from sparks and heat generated during a welding operation.

On the other hand, the main body 5101, the fixing unit 5180, the camera unit 5110, the display unit 5120, the processor 5140, the sensor unit 5150, the outer cover unit 5160, the inner cover unit 5170 and the communication unit 5190 of this embodiment may be the same as included in the above-described embodiments or may be similarly modified within a possible range. Accordingly, hereinafter, differences from the above-described embodiments will be mainly described.

The camera unit 5110 according to an embodiment of the present disclosure is mounted on the main body 5101, and may obtain a welding image frame for a welding operation.

The camera unit 5110 according to an embodiment of the present disclosure may be protected by the outer cover unit 5160.

The outer cover unit 5160 according to an embodiment of the present disclosure may include an outer cover frame 5161, an outer cover plate 5162 and a light blocking cartridge 5163.

Referring to FIGS. 30, 31, and 33, the display unit 5120 according to an embodiment of the present disclosure is disposed inside the main body 5101, and may provide a welding image generated through the welding image frame.

The display unit 5120 according to an embodiment of the present disclosure may be disposed inside the main body 5101, but may be disposed at a location capable of providing the welding image indirectly by the path change unit 5130 to be described later other than a location capable of providing the welding image directly to the user's field of view.

Referring to FIG. 30, the display unit 5120 according to an embodiment of the present disclosure may be positioned so that a direction in which the welding image is provided is perpendicular to an optical axis AX1 of the camera unit 5110.

Referring to FIG. 30, the display unit 5120 according to an embodiment of the present disclosure may be located near the user's forehead to provide the welding image toward the path change unit 5130.

Referring to FIG. 30, the display unit 5120 according to an embodiment of the present disclosure may be disposed to face the path change unit 5130. Accordingly, the welding image generated by the display unit 5120 may be transmitted to the user's eyes through the path change unit 5130.

Referring to FIGS. 30, 32, 33, 35 and 36, the path change unit 5130 according to an embodiment of the present disclosure is installed on the main body 5101, and is installed on an inner surface of the main body 5101 viewed by the user.

The path change unit 5130 according to an embodiment of the present disclosure may be disposed to face the display unit 5120, and may change the welding image provided from the display unit 5120 to guide the user's eyes.

Referring to FIGS. 30, 32, 33 and 34, the path change unit 5130 according to an embodiment of the present disclosure may be formed of a mirror reflecting the welding image.

Referring to FIG. 30, the path change unit 5130 according to an embodiment of the present disclosure may include a first mirror 5131 changing the path of the welding image provided from the display unit 5120 (P1→P2), and a second mirror 5132 changing the path of the welding image changed by the first mirror 5131 (P2→P3) to guide the user's eyes.

Referring to FIG. 30, although the path of the welding image is changed by two mirrors, but it is not limited thereto, and various modifications are possible, such as changing the path of the welding image by further including three or more mirrors or a member capable of changing the path.

The first mirror 5131 and the second mirror 5132 according to an embodiment of the present disclosure may be made of or coated with a material reflecting the welding image, for example, any one of poly methyl methacrylate (PMMA), poly carbonate (PC), polyester, silver (Ag) or aluminum (Al).

The first mirror 5131 according to an embodiment of the present disclosure is inclined at an angle of 45° to 50° with respect to the path of the welding image, so that the path of the welding image may be changed vertically.

Similarly, the second mirror 5132 is inclined at an angle of 45° to 50° with respect to the path of the welding image changed by the first mirror 5131, so that the path of the welding image may be changed vertically. For example, the first mirror 5131 and the second mirror 5132 may be arranged in a line symmetrical relationship with respect to a center line passing through the path change unit 5130, but the present disclosure is not limited thereto.

Referring to FIG. 30, the welding image provided from the display unit 5120 according to an embodiment of the present disclosure may be reversed by being reflected by the first mirror 5131, and then reversed by the second mirror 5132 and provided to the user.

At this time, in order to provide the user with the same image as the actual work site, the display unit 5120 has to provide the welding image in a state in which the upper and lower images inverted, so the welding image provided by the display unit 5120 may be an in which the image obtained through the camera unit 5110 is inverted vertically and horizontally.

As an optional embodiment, when the path change unit 5130 includes more mirrors, in order to provide the user with the same image as the work site, the processor 5140 may change the direction of the image acquired from the camera unit 5110 and transmit it to the display unit 5120.

Since it is difficult for the human eye to focus on an object that is too close, a clear image may be obtained only by placing the display unit 5120 at the focal length of the field of view. If the display unit 5120 is disposed in front of the user, the size of the welding information providing apparatus 5100 is inevitably increased to ensure such the distance.

The welding information providing apparatus 5100 according to an embodiment of the present disclosure may ensure the focal length of the welding image provided from the display unit 5120 through the path change unit 5130 and arrange the display unit 5120 at an appropriate position, thereby configuring compactly the size of the main body 5101.

A distance of a path through which the welding image passes from the display unit 5120 to the user's eye through the path change unit 5130 according to an embodiment of the present disclosure may be 200 mm or more.

In addition, the user may work at a distance of about 500 mm to 700 mm from the field of view to the field, and when the distance of the path of the welding image provided from the display unit 5120 exceeds 700 mm, a sense of incongruity between the environment in which the user work and the image may occur.

Accordingly, the path of the welding image changed through the path change unit 5130 may be determined in a range of 700 mm or less. In other words, the sum of the P1 path, P2 path and P3 path of FIG. 30 may be 200 mm or more and 700 mm or less.

Referring to FIG. 30, the welding information providing apparatus 5100 may further include the inner cover unit 5170, which will be described later, between the path change unit 5130 and the user's eyes, that is, on the path through which the welding image passes.

Due to the inner cover unit 5170 according to an embodiment of the present disclosure, it is possible to prevent foreign substances from penetrating into a space formed by the path change unit 5130, the camera unit 5110 and the display unit 5120.

The inner cover unit 5170 according to an embodiment of the present disclosure will be described in detail later.

The processor 5140 according to an embodiment of the present disclosure may control the display unit 5120 to display the welding image generated based on the welding image frame.

The processor 5140 according to an embodiment of the present disclosure may generate a high-quality composite image by synthesizing the welding image frame received through the camera unit 5110.

Referring to FIG. 30, the camera unit 5110 according to an embodiment of the present disclosure may be disposed at a position where a virtual extension line extending from the optical axis AX1 of the camera passes through the path change unit 5130.

Specifically, the virtual extension line extending from the optical axis AX1 of the camera unit 5110 may pass through the second mirror 5132 of the path change unit 5130. The camera unit 5110 according to an embodiment of the present disclosure may be located within a range of ±30 mm in a vertical direction with respect to an imaginary surface that is parallel to the path of the welding image from the second mirror 5132 and passes through a center of the second mirror 5132.

In other words, the camera unit 5110 may be disposed on a front portion of the main body 5101 to be positioned at a height similar to the user's field of view.

Due to this, the same image as the user's eye level may be obtained.

As an optional embodiment, the camera unit 5110 may include two cameras corresponding to each of the user's left and right eyes. The two cameras may be arranged symmetrically with respect to a center line of the main body 5101, and a distance between the optical axes of each camera may have a value in the range of 60 mm to 70 mm.

As described above, the two cameras may be located within the range of ±30 mm in the vertical direction with respect to the imaginary surface passing through the center of the second mirror 5132.

Referring to FIGS. 30 to 36, the inner cover unit 5170 according to an embodiment of the present disclosure is disposed on the path of the welding image, and may open and close a space formed by the display unit 5120 and the path change unit 5130.

Referring to FIGS. 30 to 36, the inner cover unit 5170 according to an embodiment of the present disclosure may include a cover frame unit 5171, a cover holder unit 5175, a sealing unit 5179S and a lens unit 5179L.

Referring to FIG. 30, the cover frame unit 5171 according to an embodiment of the present disclosure is installed on the main body 5101, and a central portion thereof may be opened. Referring to FIGS. 30 and 33, the cover frame unit 5171 according to an embodiment of the present disclosure may be installed on one side of the main body 5101 facing the user.

Referring to FIGS. 32, 33 and 35, the cover frame unit 5171 according to an embodiment of the present disclosure may be formed of a material having a predetermined rigidity.

Specifically, the cover frame unit 5171 may be formed of a metal or plastic material, but may be formed of various materials within the technical concept that the cover frame unit 5171 is closely connected to the main body 5101 and may maintain a shape.

Referring to FIG. 33, in the cover frame unit 5171 according to an embodiment of the present disclosure, the central portion may be opened, and an inner cover plate 5174 to be described later is in contact with the cover frame unit 5171 and may cover the central portion of the cover frame unit 5171.

Referring to FIGS. 30, 32 and 35, the inner cover plate 5174 according to an embodiment of the present disclosure covers the central portion of the cover frame unit 5171, so that foreign substances such as dust may be prevented from flowing from one side of the inner cover unit 5170 (right side of FIG. 30), where the user is located, to the other side (left side of FIG. 30), that is, into an internal space of the main body 5101.

Referring to FIG. 30, the internal space of the main body 5101 located on the other side (the left side of FIG. 30) opposite to the one side (right side of FIG. 30) of the inner cover unit 5170 facing the user may be formed by the display unit 5120 and the path change unit 5130.

Referring to FIG. 30, the display unit 5120 installed inside the main body 5101 according to an embodiment of the present disclosure receives the welding image frame for the welding operation obtained by the camera unit 5110 as an electrical signal, and may provide the welding image generated through such the welding image frame.

The image provided by the display unit 5120 may be delivered and provided to the user's eyes through the path change unit 5130 installed inside the main body 5101 together with the display unit 5120.

Referring to FIG. 30, the inner cover unit 5170 according to an embodiment of the present disclosure is disposed between the path change unit 5130 and the user, and the inner cover unit 5170 may be placed on the path through which the welding image generated from the display unit 5120 is transmitted through the path change unit 5130.

Referring to FIG. 30, when foreign substances such as dust are introduced into the internal space of the main body 5101 in which the path change unit 5130 and the display unit 5120 are disposed according to an embodiment of the present disclosure, the foreign substances may be in contact with or attached to the path change unit 5130 including the first mirror 5131 and the second mirror 5132.

Due to this, the field of view of the user who sees the welding image provided from the display unit 5120 and delivered to the user through the path change unit 5130 may be disturbed, and the welding operation may not be performed efficiently due to this sense of foreignness.

Since the inner cover unit 5170 according to an embodiment of the present disclosure covers the space and is fixedly installed on the main body 5101, it is possible to prevent foreign substances such as dust from penetrating into the space from the outside.

Referring to FIGS. 30, 31, 32 and 33, the cover frame unit 5171 according to an embodiment of the present disclosure may be fixedly positioned and connected to the main body 5101 along a circumference with respect to the central portion.

Referring to FIGS. 33, 35 and 36, the cover frame unit 5171 according to an embodiment of the present disclosure may be connected to the main body 5101 along the circumference with respect to the opened central portion, and a locking portion 5172 protruding in one direction (downward direction of FIG. 35) may be formed in the cover frame unit 5171.

Referring to FIGS. 35 and 36, the locking portion 5172 may be formed of the same material as the cover frame unit 5171, and the locking portion 5172 may be inserted into the cover holder unit 5175 to be described later, specifically, a seating portion 5176*a* formed in a gripping portion 5176.

Referring to FIGS. 35 and 36, the locking portion 5172 according to an embodiment of the present disclosure may be provided in plurality and protrude from one side (lower side of FIG. 35) of the cover frame unit 5171. Because the locking portion 5172 is inserted into the seating portion 5176*a* formed in the cover holder unit 5175, the cover holder unit 5175 covers the cover frame unit 5171 and may be stably positioned.

Referring to FIGS. 35 and 36, one surface of the locking portion 5172 according to an embodiment of the present disclosure, which faces a direction in which the cover holder unit 5175, specifically, the gripping portion 5176 is adjacent, may be formed as an inclined surface.

Specifically, the one surface may be formed to be inclined upward in a direction toward the camera unit 5110. Here, the 'formed to be inclined upward' means that the height of the locking portion 5172 protruding from the cover frame unit 5171 is formed to become relatively higher in the direction toward the camera unit 5110 (from the right to the left in FIG. 35).

Due to this, when the cover holder unit 5175 rotates in a clockwise direction (based on FIG. 35) with respect to a rotation center C and covers the cover frame unit 5171, the gripping portion 5176 formed in the cover holder unit 5175 may move stably while in contact with the one surface (bottom of FIG. 35) of the locking portion 5172 formed to be inclined.

In addition, because the other surface of the locking portion 5172 (left surface in FIG. 35) is draped inside the seating portion 5176*a* formed in the gripping portion 5176, the cover holder unit 5175 may be fixed while stably covering the cover frame unit 5171.

Referring to FIGS. 32, 33, 35 and 36, in the cover frame unit 5171 according to an embodiment of the present disclosure, a groove portion 5173 may be formed along the circumference based on the central portion formed in the shape of an opening.

The groove portion 5173 according to an embodiment of the present disclosure may be formed in a groove shape having a predetermined depth, and the sealing unit 5179S may be installed in the groove portion 5173.

The sealing unit 5179S according to an embodiment of the present disclosure may be formed of an elastically deformable material, specifically, a rubber material, and the sealing unit 5179S may be installed in close contact with the groove portion 5173 formed in the cover frame unit 5171.

Referring to FIGS. 32, 33, 35 and 36, the sealing unit 5179S according to an embodiment of the present disclosure may be fixed in close contact with the groove portion 5173 formed in the cover frame unit 5171, and one side (right surface of FIG. 32) may be in close contact with the inner cover plate 5174.

As the sealing unit 5179S according to an embodiment of the present disclosure is formed of the elastically deformable material, the cover holder unit 5175 is rotated on the cover frame unit 5171 and covers the cover frame unit 5171, so that the sealing unit 5179S may be deformed, specifically compressed.

Due to this, it is possible to block foreign substances such as dust from moving into a space formed between the cover frame unit 5171 and the inner cover plate 5174.

In addition, it is possible to prevent foreign substances such as dust from penetrating into the internal space of the main body 5101, specifically, the space in which the path formed by the display unit 5120 and the path change unit 5130 and through which the welding image provided from the display unit 5120 is transmitted through the path change unit 5130 is formed, from the outside due to the sealing unit 5179S and the inner cover plate 5174 being in close contact with each other.

The groove portion 5173 formed in the cover frame unit 5171 according to an embodiment of the present disclosure is formed to extend along the circumference, but it is not limited thereto, and various modifications are possible, such as the groove portion 5173 is independently set in a plurality of sections preset along the circumference of the cover frame unit 5171, and the sealing unit 5179S is installed in the plurality of groove portions 5173.

Referring to FIGS. 30 to 32, the inner cover plate 5174 according to an embodiment of the present disclosure may cover the central portion formed in the opening shape in the cover frame unit 5171.

Due to this, it is possible to block foreign substances from being introduced into the internal space of the main body 5101, in which a transmission path through which the welding image is transmitted to the user through the path change unit 5130 is formed, from the outside.

Referring to FIGS. 32 and 33, the inner cover plate 5174 according to an embodiment of the present disclosure may be formed in a plate shape and made of a transparent material. Due to this, the user may ensure the field of view for the welding image provided from the display unit 5120 and transmitted through the path change unit 5130.

However, the present invention is not limited thereto, and various modifications, such as being formed by varying transparency, are possible.

Referring to FIGS. 32, 33, 35 and 36, in the inner cover plate 5174 according to an embodiment of the present disclosure, a preset area on one side (left side of FIG. 32) is in contact with the sealing unit 5179S, and the opposite side (right side of FIG. 32) may be in contact with the cover holder unit 5175.

While the cover holder unit 5175 is connected to the inner cover plate 5174, it is rotated clockwise (in FIG. 35) with respect to the rotation center C and may cover the cover frame unit 5171. At this time, the inner cover plate 5174 is placed between the sealing unit 5179S extends along the circumference and the cover holder unit 5175, and both sides are in close contact with the sealing unit 5179S and the cover holder unit 5175, respectively, and the position may be fixed.

Accordingly, it is possible to block foreign substances such as dust from penetrating into the internal space of the main body 5101, specifically, the space formed by the display unit 5120 and the path change unit 5130 and where the transmission path of the welding image is formed, from the outside.

The inner cover plate 5174 according to an embodiment of the present disclosure is replaceable, the cover holder unit 5175 is spaced apart from the inner cover plate 5174, the inner cover plate 5174 is removed from the sealing unit 5179S arranged in the groove portion 5173 formed in the cover frame unit 5171 and may be placed back after being washed or replaced.

Referring to FIGS. 30 to 36, the cover holder unit 5175 according to an embodiment of the present disclosure has one end connected to the cover frame unit 5171, and may cover the inner cover plate 5174 connected to the cover frame unit 5171.

Referring to FIGS. 32 and 35, the cover holder unit 5175 according to an embodiment of the present disclosure has one end (upper end of FIG. 35) connected to the cover frame unit 5171, and may be rotated in a clockwise or counterclockwise direction with predetermined point formed in the area where the cover frame unit 5171 and the cover holder unit 5175 are connected as the rotation center C.

Specifically, the cover holder unit 5175 may cover the inner cover plate 5174 connected to the cover frame unit 5171 and the cover frame unit 5171 by rotating clockwise with respect to the rotation center C.

On the contrary, the cover holder unit 5175 is spaced apart from the inner cover plate 5174 connected to the cover frame unit 5171 and the cover frame unit 5171 to remove the inner cover plate 5174 from the cover frame unit 5171 by rotating counterclockwise with respect to the rotation center C.

Referring to FIGS. 31 and 34, in the cover holder unit 5175 according to an embodiment of the present disclosure, the central portion formed of an opening shape in the cover frame unit 5171 and an area overlapping the inner cover plate 5174 connected to the cover frame unit 5171 may be formed in an opening shape.

Referring to FIGS. 30 to 36, the lens unit 5179L may be installed in the area formed in the cover holder unit 5175 according to an embodiment of the present disclosure. The lens unit 5179L may be formed of a transparent material, and may be formed by varying degrees of refraction.

Due to this, the lens unit 5179L having various degrees of refraction according to the eyesight of the user using the welding information providing apparatus 5100 may be installed in the cover holder unit 5175, and the user may be provided with an accurate welding image.

Referring to FIGS. 31, 33, 34 and 35, in the cover holder unit 5175 according to an embodiment of the present disclosure, the lens fixing unit 5177 may be formed to protrude outward and extend, so that one end is contactable to the lens unit 5179L installed in the cover holder unit 5175 along the circumference.

Referring to FIGS. 31, 33 and 34, the lens fixing unit 5177 according to an embodiment of the present disclosure may be provided in plural, and may contact a plurality of points formed on the lens unit 5179L disposed at the cover holder unit 5175 to fix the lens unit 5179L.

Referring to FIG. 34, the lens fixing unit 5177 according to an embodiment of the present disclosure may have a curved surface 5178 at one end contactable with the lens unit 5179L disposed on the cover holder unit 5175.

For this reason, as illustrated in FIG. 34, when the lens unit 5179L is placed on the cover holder unit 5175, it may be installed by sliding it in a preset direction, and it allows the lens unit 5179L to be easily installed in a preset position while in contact with the curved surface 5178 formed on the lens fixing unit 5177.

Referring to FIG. 34, a plurality of lens fixing units 5177 formed in the cover holder unit 5175 according to an embodiment of the present disclosure may be arranged to be symmetrical to each other on both sides with respect to the center of the cover holder unit 5175.

Due to this, the plurality of lens fixing units 5177 contact and press the plurality of points symmetrical to each other with respect to the center on the lens unit 5179L disposed in the cover holder unit 5175, and may stably fix the lens unit 5179L on the cover holder unit 5175.

Referring to FIGS. 32 to 36, the gripping portion 5176 may protrude from the other end opposite to one end of the cover holder unit 5175 that is rotatably connected to the cover frame unit 5171 according to an embodiment of the present disclosure. The gripping portion 5176 according to an embodiment of the present disclosure may be in contact with one side of the cover frame unit 5171 (lower side of FIG. 32) when it contacts, pressurizes and covers the cover frame unit 5171 and the inner cover plate 5174 disposed on the cover frame unit 5171 by rotating clockwise with the point at which the cover holder unit 5175 is connected to the cover frame unit 5171 as the rotation center C.

Referring to FIGS. 32 to 36, the gripping portion 5176 according to an embodiment of the present disclosure may be provided in plural on the cover holder unit 5175.

The seating portion 5176*a* may be formed in the gripping portion 5176 according to an embodiment of the present disclosure. In the present disclosure, the seating portion 5176*a* is formed in a hole shape, but is not limited thereto, and various modifications such as being formed in a shape of groove having a predetermined depth are possible within the technical idea that the locking portion 5172 protruding outward from one side (lower side of FIG. 35) of the cover frame unit 5171 may be inserted and spanned.

Referring to FIGS. 32 and 35, as the cover holder unit 5175 is rotated clockwise with respect to the rotation center C, the gripping portion 5176 according to an embodiment of the present disclosure is contactable with the locking portion 5172 formed in the cover frame unit 5171.

Specifically, as the gripping portion 5176 is movable along the one surface (lower surface of FIG. 35) formed to be inclined on the locking portion 5172, and as the seating portion 5176*a* formed on gripping portion 5176 is spanned over the locking portion 5172 formed on cover frame unit 5171, the cover holder unit 5175 contacts and presses the cover frame unit 5171 and the inner cover plate 5174 installed on the cover frame unit 5171 to fix them.

As the cover holder unit 5175 contacts and pressurizes the cover frame unit 5171 and the inner cover plate 5174 installed in the cover frame unit 5171, the adhesion between the inner cover plate 5174 and the sealing unit 5179S installed in cover frame unit 5171 is increased, and foreign substances such as dust may be blocked from introducing into the internal space of the main body 5101, specifically, the space formed by the display unit 5120 and the path change unit 5130, from the outside.

Since foreign substances such as dust are blocked from entering the space, the path change unit 5130 is prevented from being contaminated by the foreign substances, and it may be prevented that the field of view for the welding image provided from the display unit 5120 and transmitted to the user through the path change unit 5130 is obstructed by the foreign substances attached to the path change unit 5130 or the like.

Referring to FIGS. 32, 35 and 36, due to the gripping portion 5176 according to an embodiment of the present disclosure, the cover holder unit 5175 may wrap and cover a plurality of surfaces (right side and bottom side of FIG. 32) formed on the cover frame unit 5171, and may stably cover the cover frame unit 5171 and the inner cover plate 5174 installed on the cover frame unit 5171.

Referring to FIGS. 29 and 30, the fixing unit 5180 according to an embodiment of the present disclosure is disposed on the rear surface of the main body 5101 and may be connected to the main body 5101. The user may place the fixing unit 5180 in contact with the user's head, thereby stably fixing the position of the welding information providing apparatus 5100.

The fixing unit 5180 according to an embodiment of the present disclosure may include an adjustment unit (reference numeral not set) capable of adjusting an inner circumference length of the fixing unit 5180 according to the size of the user's head. The user may adjust the circumference of the fixing unit 5180 by holding the adjustment unit and rotating it clockwise or counterclockwise to stably fix the fixing unit 5180 and the main body 5101 connected to fixing unit 5180 to the outside of the user's head.

Referring to FIGS. 29 and 30, both sides of the fixing unit 5180 according to an embodiment of the present disclosure may be connected to the main body 5101. The both sides of the fixing unit 5180 may be rotatably connected to the main body 5101, and the user may ensure the field of view about the user's external environment by rotating the main body 5101 while the fixing unit 5180 is fixed to the user's head.

Referring to FIG. 30, a fixing unit according to an embodiment of the present disclosure adjusts the circumference length of the fixing unit 5180 in a rotating manner, but is not limited thereto, and various modifications are possible within the technical idea that may be in close contact with the user's head, such as adjusting the circumference length of the fixing unit 5180 by a slide movement method and a button method or the like.

Referring to FIGS. 29 and 30, the fixing unit 5180 according to an embodiment of the present disclosure may have a structure including a plurality of ribs such as a headgear, and elements comprising a soft material such as a fiber material or a cushion material and disposed in at least some regions of the inner surface in direct contact with the head of the user performing the welding operation.

The communication unit 5190 according to an embodiment of the present disclosure is configured to receive welding information from a welding torch 5200 and transmit a command for controlling the welding torch 5200.

The welding information providing apparatus 5100 according to an embodiment of the present disclosure may block foreign substances such as dust from being introducing into the internal space of the main body 5101, specifically, the space formed by the display unit 5120 and the path change unit 5130, from the outside as the inner cover unit 5170 installed on the main body 5101 and disposed on the path of the welding image.

In addition, the cover holder unit 5175 may be rotatably connected in a clockwise or counterclockwise direction with the area connected to the cover frame unit 5171 as the rotation center C, so that the inner cover plate 5174 installed in cover frame unit 5171 is in close contact with the cover frame unit 5171 and may be stably fixed.

In addition, as the sealing unit 5179S is seated in the groove portion 5173 formed in the cover frame unit 5171 and one side of the sealing unit 5179S is in close contact with the inner cover plate 5174, the space may be closed, and foreign substances such as dust may be prevented from flowing through the space formed between the inner cover plate 5174 and the cover frame unit 5171.

In addition, the inner cover plate 5174 may be easily replaced as it is formed in a plate shape and disposed between the cover frame unit 5171 and the cover holder unit 5175.

In addition, the lens unit 5179L covers the area formed in the shape of an opening in the cover holder unit 5175, and the lens fixing unit 5177 protruding from the cover holder unit 5175 contacts and presses the lens unit 5179L, so that the position of the lens unit 5179L may be stably fixed.

In addition, the lens unit 5179L may be disposed on the cover holder unit 5175 to be contactable to the lens fixing unit 5177 formed in the cover holder unit 5175, and the lens unit 5179L may be separated from the cover holder unit 5175 in a method of releasing contact with the lens fixing unit 5177, so that the lens unit 5179L with different degrees of refraction according to the user's eyesight may be easily replaced.

As described above, the present disclosure has been described with reference to one embodiment shown in the drawings, but this is merely exemplary, and those of ordinary skill in the art will understand that various modifications and variations of the embodiments are possible therefrom. Therefore, the true technical protection scope of the present disclosure should be determined by the technical idea of the appended claims.

INDUSTRIAL APPLICABILITY

According to an embodiment of the present disclosure, it is possible to provide an apparatus for providing welding information during welding. In addition, embodiments of the present disclosure may be applied to welding information providing apparatus used in industry.

What is claimed is:

1. A welding information providing apparatus comprising:
- a main body provided to be worn by a user;
- a display unit arranged on the main body and including a display for displaying a welding image to the user;
- at least one camera unit attached to an outer side of the main body and obtaining welding image frames with respect to a welding operation; and
- a processor configured to control the display to display the welding image generated based on the welding image frames; and
- an optical sensor for detecting whether there is welding light and an intensity of the welding light,
- wherein the camera unit includes a darkening filter blocking welding light generated due to the welding operation and a neutral density filter arranged in front of the darkening filter,
- wherein, when the welding light is greater than an intensity set in advance, the processor is configured to generate a first control signal and a second control signal and to control both the darkening filter and the neutral density filter to operate.

2. The welding information providing apparatus of claim 1, wherein the darkening filter is arranged in front of a lens receiving light from a subject.

3. A camera unit comprising:
- a lens assembly including one or more lenses;
- a substrate assembly including an image sensor that recognizes light passing through the lens assembly and a printed circuit board coupled to the image sensor;
- a filter unit arranged on a path through which the light moves and including a darkening filter blocking the light and a neutral density filter arranged in front of the darkening filter; and
- a processor configured to control a darkening density of the darkening filter and a neutral density of the neutral density filter, wherein, when the light is greater than an intensity set in advance, the processor is configured to generate a first control signal and a second control signal and to control both the darkening filter and the neutral density filter to operate.

4. The camera unit of claim 3, wherein the filter unit is arranged in front of the lens assembly receiving light from a subject.

5. The camera unit of claim 3, wherein the filter unit is arranged between the lens assembly and the image sensor.

* * * * *